(12) United States Patent
Taoda et al.

(10) Patent No.: US 12,139,489 B2
(45) Date of Patent: Nov. 12, 2024

(54) POLYCYCLIC CARBAMOYLPYRIDONE DERIVATIVE

(71) Applicant: Shionogi & Co., Ltd., Osaka (JP)

(72) Inventors: Yoshiyuki Taoda, Osaka (JP); Yuto Unoh, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 18/124,827

(22) Filed: Mar. 22, 2023

(65) Prior Publication Data

US 2023/0227454 A1    Jul. 20, 2023

Related U.S. Application Data

(62) Division of application No. 17/058,251, filed as application No. PCT/JP2019/021446 on May 30, 2019, now Pat. No. 11,649,236.

(30) Foreign Application Priority Data

May 31, 2018 (JP) ................................. 2018-104156

(51) Int. Cl.
| | | |
|---|---|---|
| A61K 31/53 | (2006.01) | |
| A61P 31/18 | (2006.01) | |
| C07D 471/14 | (2006.01) | |
| C07D 471/18 | (2006.01) | |
| C07D 487/14 | (2006.01) | |
| C07D 491/22 | (2006.01) | |
| C07D 498/22 | (2006.01) | |

(52) U.S. Cl.
CPC ............ *C07D 471/14* (2013.01); *A61K 31/53* (2013.01); *A61P 31/18* (2018.01); *C07D 471/18* (2013.01); *C07D 487/14* (2013.01); *C07D 491/22* (2013.01); *C07D 498/22* (2013.01)

(58) Field of Classification Search
CPC .............................. A61K 31/53; C07D 487/14
See application file for complete search history.

(56) References Cited

U.S. PATENT DOCUMENTS

| | | |
|---|---|---|
| 7,858,788 B2 | 12/2010 | Yoshida et al. |
| 8,129,385 B2 | 3/2012 | Johns et al. |
| 8,188,271 B2 | 5/2012 | Yoshida et al. |
| 8,410,103 B2 | 4/2013 | Johns et al. |
| 8,778,943 B2 | 7/2014 | Johns et al. |
| 9,273,065 B2 | 3/2016 | Johns et al. |
| 10,927,129 B2 | 2/2021 | Johns et al. |
| 11,267,823 B2 | 3/2022 | Johns et al. |
| 11,453,669 B2 | 9/2022 | Taoda |
| 2008/0161271 A1 | 7/2008 | Yoshida et al. |
| 2009/0143356 A1 | 6/2009 | Yoshida et al. |
| 2009/0318421 A1 | 12/2009 | Johns et al. |
| 2012/0115875 A1 | 5/2012 | Johns et al. |
| 2012/0208998 A1 | 8/2012 | Yoshida et al. |
| 2013/0096109 A1 | 4/2013 | Hattori et al. |
| 2013/0172559 A1 | 7/2013 | Johns et al. |
| 2014/0200209 A1 | 7/2014 | Johns et al. |
| 2015/0232479 A1 | 8/2015 | Johns et al. |
| 2016/0137666 A1 | 5/2016 | Johns et al. |
| 2016/0207939 A1 | 7/2016 | Johns et al. |
| 2016/0304535 A1 | 10/2016 | Johns et al. |
| 2017/0029438 A1 | 2/2017 | Johns et al. |
| 2017/0145033 A1 | 5/2017 | Johns et al. |
| 2017/0209454 A1 | 7/2017 | Johns et al. |
| 2017/0224694 A1 | 8/2017 | Johns et al. |
| 2017/0224695 A1 | 8/2017 | Johns et al. |
| 2017/0253616 A1 | 9/2017 | Johns et al. |
| 2017/0260203 A1 | 9/2017 | Johns et al. |
| 2017/0267693 A1 | 9/2017 | Johns et al. |

(Continued)

FOREIGN PATENT DOCUMENTS

| | | |
|---|---|---|
| EP | 1 544 199 | 6/2005 |
| EP | 1 852 434 | 11/2007 |

(Continued)

OTHER PUBLICATIONS

Extended European Search Report issued Sep. 28, 2023 in corresponding European Patent Application No. 23192706.2, 9 pages.
International Search Report issued Aug. 13, 2019 in International (PCT) Application No. PCT/JP2019/021446 with English-language translation.
Nagase, Hiroshi, "The Practice of Medicinal Chemistry", Latest medicinal chemistry, 1998, pp. 476, 494-495, with English-language translation.
"Resolution of Enantiomers", Separation of optical isomers, 1989, pp. 16-17, with English-language translation.

(Continued)

*Primary Examiner* — Susanna Moore
(74) *Attorney, Agent, or Firm* — Wenderoth, Lind & Ponack, L.L.P.

(57) ABSTRACT

The present invention provides a compound represented by Formula (I):

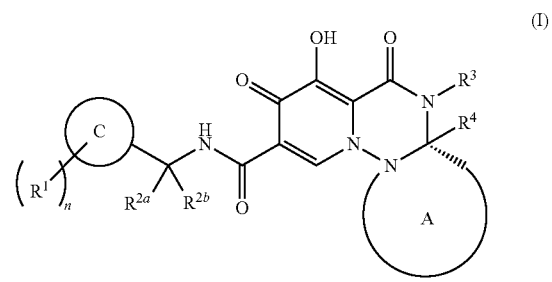

wherein ring A is a substituted or unsubstituted heterocycle; ring C is a benzene ring or the like; $R^1$ is halogen or the like; $R^{2a}$ and $R^{2b}$ are each independently hydrogen or the like; $R^3$ is substituted or unsubstituted alkyl or the like; $R^4$ is hydrogen or the like; and n is an integer of 1 to 3.

10 Claims, No Drawings

(56) References Cited

U.S. PATENT DOCUMENTS

| | | |
|---|---|---|
| 2017/0369509 A1 | 12/2017 | Johns et al. |
| 2019/0152990 A1 | 5/2019 | Johns et al. |
| 2019/0284208 A1 | 9/2019 | Johns et al. |
| 2020/0033598 A1 | 1/2020 | Ma |
| 2022/0213121 A1 | 7/2022 | Johns et al. |

FOREIGN PATENT DOCUMENTS

| | | |
|---|---|---|
| EP | 1 950 212 | 7/2008 |
| EP | 1 578 748 | 9/2010 |
| EP | 2 540 720 | 1/2013 |
| EP | 2 774 928 | 9/2014 |
| EP | 2 940 019 | 11/2015 |
| EP | 3 196 201 | 7/2017 |
| WO | 2004/024078 | 3/2004 |
| WO | 2005/016927 | 2/2005 |
| WO | 2006/088173 | 8/2006 |
| WO | 2006/116764 | 11/2006 |
| WO | 2007/049675 | 5/2007 |
| WO | 2011/105590 | 9/2011 |
| WO | 2011/129095 | 10/2011 |
| WO | 2013/054862 | 4/2013 |
| WO | 2014/099586 | 6/2014 |
| WO | 2014/100323 | 6/2014 |
| WO | 2014/104279 | 7/2014 |
| WO | 2014/183532 | 11/2014 |
| WO | 2014/200880 | 12/2014 |
| WO | 2015/006731 | 1/2015 |
| WO | 2015/006733 | 1/2015 |
| WO | 2015/039348 | 3/2015 |
| WO | 2015/048363 | 4/2015 |
| WO | 2015/089847 | 6/2015 |
| WO | 2015/095258 | 6/2015 |
| WO | 2015/199167 | 12/2015 |
| WO | 2016/027879 | 2/2016 |
| WO | 2016/090545 | 6/2016 |
| WO | 2016/094197 | 6/2016 |
| WO | 2016/094198 | 6/2016 |
| WO | 2016/106237 | 6/2016 |
| WO | 2016/154527 | 9/2016 |
| WO | 2016/161382 | 10/2016 |
| WO | 2016/187788 | 12/2016 |
| WO | 2016/191239 | 12/2016 |
| WO | 2017/087256 | 5/2017 |
| WO | 2017/087257 | 5/2017 |
| WO | 2017/106071 | 6/2017 |
| WO | 2017/113288 | 7/2017 |
| WO | 2017/116928 | 7/2017 |
| WO | 2018/102634 | 6/2018 |
| WO | 2018102485 | 6/2018 |
| WO | 2019/160783 | 8/2019 |
| WO | 2019/209667 | 10/2019 |
| WO | 2019/223408 | 11/2019 |
| WO | 2019/236396 | 12/2019 |
| WO | 2020/197991 | 10/2020 |

OTHER PUBLICATIONS

International Preliminary Report on Patentability issued Dec. 10, 2020 in International (PCT) Patent Application No. PCT/JP2019/021446.
Response to Opposition filed May 17, 2017 in European Patent No. 1950212, pp. 1-10.
Experimental Report filed in Response to Opposition to European Patent No. 1950212 filed May 11, 2017, pp. 1-38.
Further Experimental Report RE: European Patent No. 1950212 filed Oct. 26, 2017, pp. 1-2.
Extended European Search Report issued Dec. 7, 2021 in corresponding European Patent Application No. 19810498.6, 10 pages.
Supplementary European Search Report issued Jan. 3, 2022 in corresponding European Patent Application No. 19810498.6, 11 pages.

POLYCYCLIC CARBAMOYLPYRIDONE DERIVATIVE

TECHNICAL FIELD

The present invention relates to a novel compound having an antiviral effect. More specifically, the present invention relates to a polycyclic carbamoylpyridone derivative having HIV integrase inhibitory activity and a medicament, particularly, an anti-HIV drug including thereof.

BACKGROUND ART

Among viruses, human immunodeficiency virus (hereinafter, abbreviated to HIV), one type of retrovirus, is known to cause acquired immunodeficiency syndrome (hereinafter, abbreviated to AIDS). Various guidelines currently recommend naive patients for a combination of an integrase inhibitor (dolutegravir, etc.) as a principal drug with two nucleic acid reverse transcriptase inhibitors (ABC+3TC, FTC+TAF, etc.) differing in resistance profile, as a therapeutic drug for AIDS. Because of strong efficacy and high safety, these combinations have a high satisfaction level as compared with initial therapeutic drugs. Meanwhile, the start of treatment upon detection of HIV infection is recommended owing to the emergence of such a safe drug and good prognosis. In addition, a medication period becomes long because people infected with IIIV have an average life expectancy closer to that of healthy people. If adverse reactions of the nucleic acid reverse transcriptase inhibitors occur or once a resistant virus appears due to the long-term medication, there is no further convenient treatment method. Thus, there is a move afoot to leave the nucleic acid reverse transcriptase inhibitors unused. Hence, the establishment of two-drug treatment with two principal drugs is desired. Thus, the development of a principal drug that can be combined with the integrase inhibitor is desired. Furthermore, the development of a therapeutic, drug with a longer medication interval, i.e., a long-acting injection with which treatment is completed merely by one injection at 1-month or longer intervals is desired for improving medication fatigue ascribable to the long-term medication and improving QOL (quality of life) of patients in such a way that the patients more enjoy daily life.

In order to meet such demands, an integrase inhibitor cabotegravir is under development as a long-acting injection at Ph3. Also, non-nucleic acid reverse transcriptase inhibitor rilpivirine is also under development as a long-acting injection. The establishment of a treatment method is being attempted using these two drugs. However, these drugs are injected once a month or two months and need to be injected at a total of 3 or 4 sites with pain. Hence, the development of a drug with which treatment is completed by one injection per 3 months with less pain at a lower dose is desired for further improving QOL of patients.

Raltegravir and elvitegravir as the first-generation oral agents and dolutegravir as the second-generation oral agent have already been launched as integrase inhibitors. When a naive patient uses dolutegravir, no resistant mutation appears. However, dolutegravir, when used in the treatment of a patient infected with a resistant virus to the first-generation integrase inhibitor, may be no longer effective due to the further addition of a resistant mutation. Hence, the development of an inhibitor having a higher resistance barrier than that of dolutegravir is also desired.

Bicyclic or higher polycyclic carbamoylpyridone derivatives are known as one of the anti-HIV drugs having an integrase inhibitory effect (Patent Documents 1 to 29). Among them, Patent Document 3 describes a carbamoylpyridotriazine derivative. However, none of the documents describe an optically active tricyclic or more polycyclic carbamoylpyridotriazine derivative which is the compound of the present application.

PRIOR ART REFERENCES

Patent Document

[Patent Document 1] WO 2006/088173
[Patent Document 2] WO 2006/116764
[Patent Document 3] WO 2007/049675
[Patent Document 4] WO 2011/129095
[Patent Document 5] WO 2014/099586
[Patent Document 6] WO 2014/100323
[Patent Document 7] WO 2014/104279
[Patent Document 8] WO 2014/183532
[Patent Document 9] WO 2014/200880
[Patent Document 10] WO 2015/039348
[Patent Document 11] WO 2015/048363
[Patent Document 12] WO 2015/089847
[Patent Document 13] WO 2015/095258
[Patent Document 14] WO 2015/006731
[Patent Document 15] WO 2015/006733
[Patent Document 16] WO 2015/199167
[Patent Document 17] WO 2016/090545
[Patent Document 18] WO 2016/094198
[Patent Document 19] WO 2016/094197
[Patent Document 20] WO 2016/106237
[Patent Document 21] WO 2016/154527
[Patent Document 22] WO 2016/161382
[Patent Document 23] WO 2016/187788
[Patent Document 24] WO 2016/191239
[Patent Document 25] WO 2017/087256
[Patent Document 26] WO 2017/087257
[Patent Document 27] WO 2017/106071
[Patent Document 28] WO 2017/113288
[Patent Document 29] WO 2017/116928

SUMMARY OF INVENTION

Problems to be Solved by the Invention

An object of the present invention is to provide a novel long-acting compound having integrase inhibitory activity with a high resistance barrier.

Means for Solving the Problem

The present inventors have conducted diligent studies and consequently found that a novel carbamoylpyridone derivative has an integrase inhibitory effect with a high resistance barrier. The present inventors have further discovered that the compound of the present invention and a medicament including thereof are useful as an antiviral drug (e.g., an anti-retrovirus drug, an anti-HIV drug, an anti-HTLV-1 (human T cell leukemia virus type 1) drug, an anti-FIV (feline immunodeficiency virus) drug, and an anti-SIV (simian immunodeficiency virus) drug), particularly, an anti-HIV drug, an anti-AIDS drug, or a therapeutic drug for related diseases thereof, etc., completing the present invention given below.

The present invention provides inventions given below.

[1] A compound represented by the following formula (I) or a pharmaceutically acceptable salt thereof:

[Chemical Formula 1]

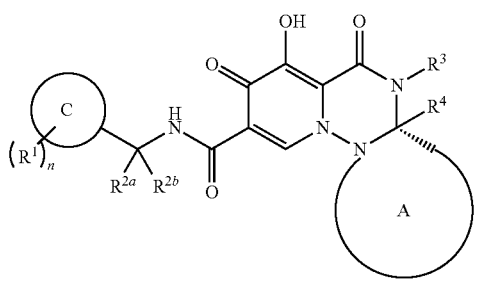

(I)

wherein
- ring A is a substituted or unsubstituted nonaromatic heterocycle;
- ring C is a benzene ring, a pyridine ring, or a 5-membered aromatic heterocycle;
- $R^1$ is each independently halogen, alkyl, haloalkyl, alkyloxy, cyano, or haloalkyloxy;
- $R^{2a}$ and $R^{2b}$ are each independently hydrogen, alkyl, or haloalkyl;
- $R^{2a}$ and $R^{2b}$ may be taken together with the adjacent carbon atom to form a nonaromatic carbocycle or a nonaromatic heterocycle;
- $R^3$ is substituted or unsubstituted alkyl, substituted or unsubstituted nonaromatic carbocyclyl, or substituted or unsubstituted nonaromatic heterocyclyl;
- $R^4$ is hydrogen, or substituted or unsubstituted alkyl;
- $R^3$ and $R^4$, or $R^3$ and a substituent on ring A may be taken together with the adjacent atoms to form a substituted or unsubstituted nonaromatic heterocycle; and
- n is an integer of 1 to 3.

[2] The compound according to [1] or a pharmaceutically acceptable salt thereof, wherein ring A is any of the following rings:

[Chemical Formula 2]

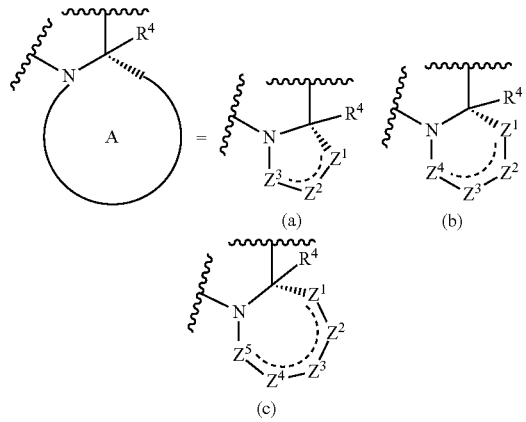

wherein
- $R^4$ is hydrogen, or substituted or unsubstituted alkyl;
- the broken line represents the presence or absence of a bond;
- $Z^1$, $Z^2$, $Z^3$, $Z^4$ and $Z^5$ are each independently $CR^{5a}R^{5b}$, $CR^{5a}$, O, N, $NR^{5c}$, or S, wherein the number of heteroatoms constituting the ring structure of ring A in $Z^1$, $Z^2$, $Z^3$, $Z^4$ and $Z^5$ is 0 or 1;
- $Z^1$ and $Z^3$, $Z^1$ and $Z^4$, $Z^1$ and $Z^5$, $Z^2$ and $Z^4$, $Z^2$ and $Z^5$, $Z^3$ and $Z^5$, $R^4$ and $Z^2$, $R^4$ and $Z^3$, $R^4$ and $Z^4$, or $R^4$ and $Z^5$ may be taken together to form a substituted or unsubstituted C1-C4 cross-link optionally interrupted by a heteroatom selected from $NR^{5c}$, O and S;
- $R^{5a}$ and $R^{5b}$ are each independently hydrogen, halogen, substituted or unsubstituted alkyl, or substituted or unsubstituted alkyloxy;
- $R^{5a}$ and $R^{5b}$ on the same carbon atom may be taken together to form a substituted or unsubstituted nonaromatic carbocycle, or a substituted or unsubstituted nonaromatic heterocycle;
- $R^{5c}$ is each independently hydrogen, substituted or unsubstituted alkyl, substituted or unsubstituted alkylcarbonyl, substituted or unsubstituted alkyloxycarbonyl, substituted or unsubstituted carbamoyl, substituted or unsubstituted aromatic carbocyclyl, substituted or unsubstituted nonaromatic carbocyclyl, substituted or unsubstituted aromatic heterocyclyl, or substituted or unsubstituted nonaromatic heterocyclyl;
- $R^3$ and $R^4$ may be taken together with the adjacent atoms to form a substituted or unsubstituted nonaromatic heterocycle.

[3] The compound according to or a pharmaceutically acceptable salt thereof, wherein ring A is any of the following rings:

[Chemical Formula 3]

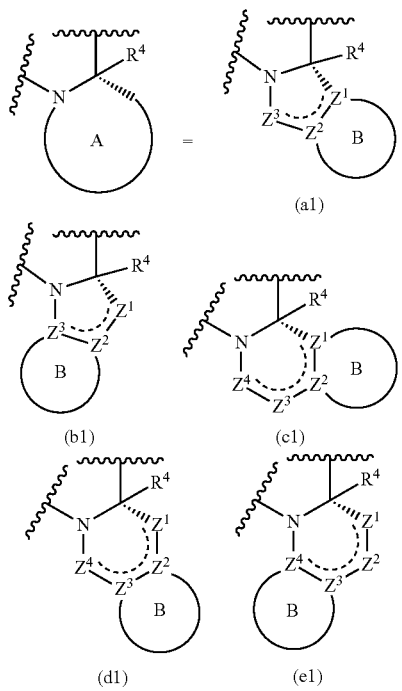

-continued

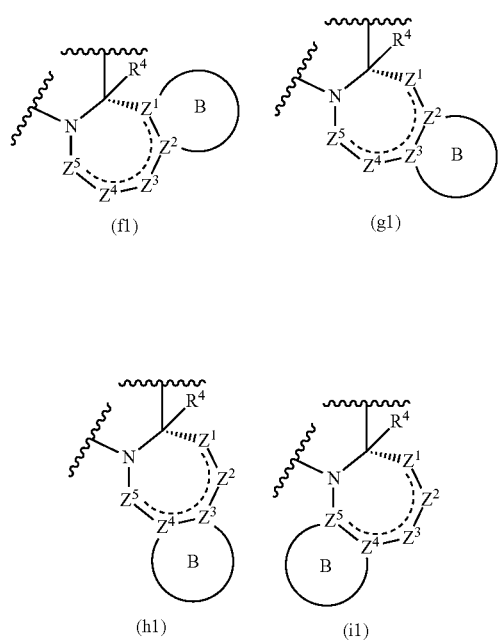

(f1)   (g1)

(h1)   (i1)

wherein
  $R^4$ is hydrogen, or substituted or unsubstituted alkyl;
  the broken line represents the presence or absence of a bond;
  ring B is a substituted or unsubstituted aromatic carbocycle, a substituted or unsubstituted nonaromatic carbocycle, or a substituted or unsubstituted nonaromatic heterocycle;
  $Z^1$, $Z^2$, $Z^3$, $Z^4$ and $Z^5$ are each independently $CR^{5a}R^{5b}$, $CR^{5a}$, C, O, N, $NR^{5c}$, or S (provided that an atom constituting ring B is $CR^{5a}$, C, or N);
  $Z^1$ and $Z^3$, $Z^1$ and $Z^4$, $Z^1$ and $Z^5$, $Z^2$ and $Z^4$, $Z^2$ and $Z^5$, $Z^3$ and $Z^5$, $R^4$ and $Z^2$, $R^4$ and $Z^3$, $R^4$ and $Z^4$ or $R^4$ and $Z^5$ may be taken together to form a substituted or unsubstituted C2-C4 cross-link optionally interrupted by a heteroatom selected from $NR^{5c}$, O and S;
  $R^{5a}$ and $R^{5b}$ are each independently hydrogen, halogen, substituted or unsubstituted alkyl, or substituted or unsubstituted alkyloxy;
  $R^{5a}$ and $R^{5b}$ on the same carbon atom may be taken together to form a substituted or unsubstituted nonaromatic carbocycle, or a substituted or unsubstituted nonaromatic heterocycle;
  $R^{5c}$ is hydrogen, substituted or unsubstituted alkyl, substituted or unsubstituted alkylcarbonyl, substituted or unsubstituted alkyloxycarbonyl, substituted or unsubstituted carbamoyl, substituted or unsubstituted aromatic carbocyclyl, substituted or unsubstituted nonaromatic carbocyclyl, substituted or unsubstituted aromatic heterocyclyl, or substituted or unsubstituted nonaromatic heterocyclyl;
  $R^3$ and $R^4$ may be taken together with the adjacent atoms to form a substituted or unsubstituted nonaromatic heterocycle.

[4] The compound according to any one of [1] to [3] or a pharmaceutically acceptable salt thereof, wherein the compound is represented by the following formula (I):

[Chemical Formula 4]

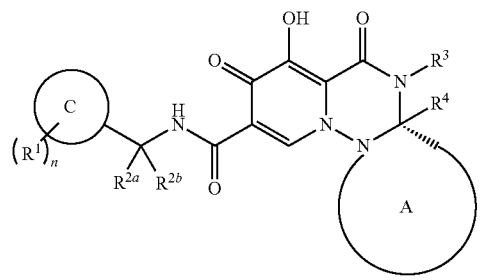

(I)

wherein
  ring A is any of the following ring:

[Chemical Formula 5]

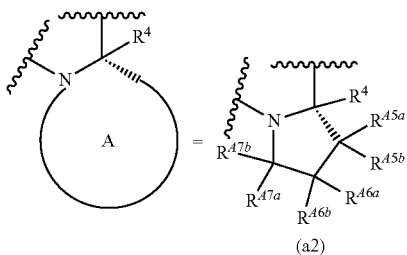

(a2)

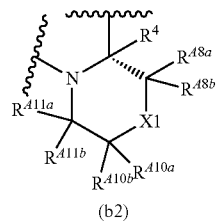

(b2)

X1 is $CR^{A9a}R^{A9b}$ or ( );
$R^{A5a}$, $R^{A5b}$, $R^{A6a}$, $R^{A6b}$, $R^{A7a}$ and $R^{A7b}$ are each independently hydrogen, alkyl, alkyloxy, or alkyloxyalkyl;
$R^{A5a}$ and $R^{A6a}$ or $R^{A6a}$ and $R^{A7a}$ may be taken together with the adjacent atoms to form an aromatic carbocycle optionally substituted by halogen, a 3- to 6-membered nonaromatic carbocycle optionally substituted by halogen, or a 4- to 6-membered nonaromatic heterocycle optionally substituted by halogen (provided that, when forming an aromatic carbocycle, $R^{A5b}$ and $R^{A6b}$, or $R^{A6b}$ and $R^{A7b}$ are taken together to form a bond);
$R^{A5b}$ and $R^{A6b}$ may be taken together to form a bond;
RhuA8a, $R^{A8b}$, $R^{A9a}$, $R^{A9b}$, $R^{A10a}$, $R^{A10b}$, $R^{A11a}$ and $R^{A11b}$ are each independently hydrogen, alkyl, alkyloxy, or alkyloxyalkyl;
$R^{A8a}$ and $R^{A10a}$ may be taken together to form a C1-C3 cross-link;

$R^{410a}$ and $R^{411a}$ may be taken together with the adjacent atoms to form a 5-membered nonaromatic carbocycle;
$R^{49a}$ and $R^{49b}$ may be taken together with the adjacent atom to form a 4-membered nonaromatic carbocycle or a 5-membered nonaromatic heterocycle;
$R^{48a}$ and $R^{49a}$ may be taken together to form a bond;
ring C is a benzene ring or a pyridine ring;
$R^1$ is each independently halogen, alkyl, haloalkyl, alkyloxy, cyano, or haloalkyloxy;
$R^{2a}$ and $R^{2b}$ are each independently hydrogen, alkyl, or haloalkyl;
$R^3$ is alkyl or haloalkyl;
$R^4$ is hydrogen or alkyl;
n is an integer of 1 to 3.

[5] The compound according to any one of [1] to [3] or a pharmaceutically acceptable salt thereof, wherein $R^3$ is alkyl or haloalkyl.

[6] The compound according to any one of [1] to [4] or a pharmaceutically acceptable salt thereof, wherein $R^3$ is alkyl.

[7] The compound according to any one of [1] to [3], [5] and [6] or a pharmaceutically acceptable salt thereof, wherein $R^4$ is hydrogen or alkyl.

[8] The compound according to any one of [1] to [7] or a pharmaceutically acceptable salt thereof, wherein $R^1$ is each independently halogen, alkyl, or haloalkyl.

[9] The compound according to any one of [1] to [7] or a pharmaceutically acceptable salt thereof, wherein $R^1$ is each independently halogen.

[10] The compound according to any one of [1] to [3] and [5] to [9] or a pharmaceutically acceptable salt thereof, wherein $R^{2a}$ is hydrogen and $R^{2b}$ is hydrogen or alkyl,
or $R^{2a}$ and $R^{2b}$ are taken together with the adjacent carbon atom to form a C3-C4 carbocycle.

[11] The compound according to any one of [1] to [9] or a pharmaceutically acceptable salt thereof, wherein $R^{2a}$ is hydrogen and $R^{2b}$ is hydrogen or alkyl.

[12] The compound according to any one of [1] to [3] and [5] to or a pharmaceutically acceptable salt thereof, wherein ring C is a benzene ring or a pyridine ring.

[13] The compound according to [1] or a pharmaceutically acceptable salt thereof, wherein the compound is selected from the group consisting of compounds I-2, I-6, I-11, and I-15.

[14] The compound according to [1] or a pharmaceutically acceptable salt thereof, wherein the compound is selected from the group consisting of compounds II-4, II-8, II-9, II-15, II-18, 11-20, II-21, II-22, II-23, II-24, II-26, II-28, II-31, II-37, II-40, II-41, II-42, II-44, II-46, II-49, II-51, II-53, II-57, II-60, II-66, II-70, II-71, II-87, II-90, II-99, II-106, II-112, II-133, II-136, II-153 and II-156.

[15] A pharmaceutical composition comprising the compound according to any one of [1] to [14] or a pharmaceutically acceptable salt thereof.

[16] The pharmaceutical composition according to [15], wherein the pharmaceutical composition is an anti-HIV agent.

[17] An HIV integrase inhibitor comprising the compound according to any one of [1] to [14] or a pharmaceutically acceptable salt thereof.

[18] A method for treating and/or preventing HIV infection, comprising administering the compound according to any one of [1] to or a pharmaceutically acceptable salt thereof.

[19] The compound according to any one of [1] [4] to or a pharmaceutically acceptable salt thereof for use in treating and/or preventing HIV infection.

[1'] A compound represented by the following formula (I') or a pharmaceutically acceptable salt thereof:

[Chemical Formula 6]

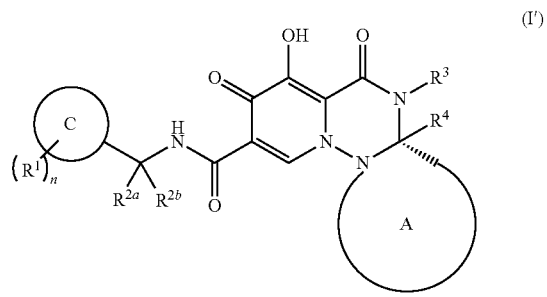

(I')

wherein
ring A is a substituted or unsubstituted heterocycle;
$R^1$ is each independently halogen, alkyl, haloalkyl, alkyloxy, nitrile, or haloalkyloxy;
$R^{2a}$ and $R^{2b}$ are each independently hydrogen, alkyl, or haloalkyl;
$R^{2a}$ and $R^{2b}$ may be taken together with an adjacent carbon atom to form a carbocycle or a heterocycle;
$R^3$ is substituted or unsubstituted alkyl, substituted or unsubstituted nonaromatic carbocyclyl, or substituted or unsubstituted nonaromatic heterocyclyl;
$R^4$ is hydrogen, or substituted or unsubstituted alkyl;
$R^3$ and $R^4$, or $R^3$ and a substituent on ring A may be taken together with the adjacent atoms to form a substituted or unsubstituted heterocycle; and
n is an integer of 1 to 3.

[2'] The compound according to [1'] or a pharmaceutically acceptable salt thereof, wherein ring A is any of the following rings:

[Chemical Formula 7]

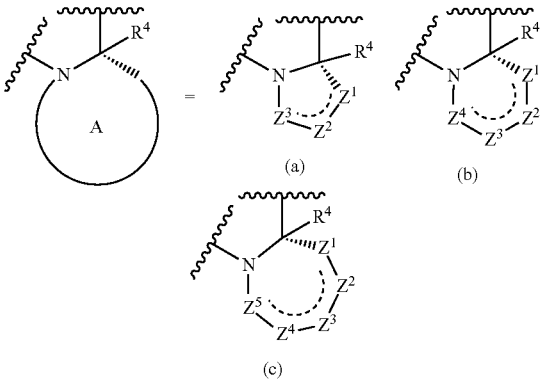

wherein
$R^4$ is hydrogen, or substituted or unsubstituted alkyl;
the broken line represents the presence or absence of a bond;
$Z^1$, $Z^2$, $Z^3$, $Z^4$ and $Z^5$ are each independently $CR^{5a}R^{5b}$, $CR^{5a}$, O, N, $NR^{5c}$, S, $S(=O)$, $S(=O)_2$, or $S(=O)=NR^{5d}$, wherein the number of heteroatoms among $Z^1$, $Z^2$, $Z^3$, $Z^4$ and $Z^5$ is 0 or 1;
$Z^1$ and $Z^3$, $Z^1$ and $Z^4$, $Z^1$ and $Z^5$, $Z^2$ and $Z^4$, $Z^2$ and $Z^5$, $Z^3$ and $Z^5$, $R^4$ and $Z^2$, $R^4$ and $Z^3$, $R^4$ and $Z^4$, or $R^4$ and $Z^5$ may be taken together to form a substituted or unsubstituted C2-C4 cross-link;

R$^{5a}$ and R$^{5b}$ are each independently hydrogen, halogen, hydroxy, substituted or unsubstituted alkyl, substituted or unsubstituted alkyloxy, substituted or unsubstituted alkyloxycarbonyl, substituted or unsubstituted amino, substituted or unsubstituted carbamoyl, substituted or unsubstituted ureido, substituted or unsubstituted aromatic carbocyclyl, substituted or unsubstituted nonaromatic carbocyclyl, substituted or unsubstituted aromatic heterocyclyl, substituted or unsubstituted nonaromatic heterocyclyl, substituted or unsubstituted aromatic carbocyclyloxy, substituted or unsubstituted nonaromatic carbocyclyloxy, substituted or unsubstituted aromatic heterocyclyloxy, or substituted or unsubstituted nonaromatic heterocyclyloxy;

R$^{5a}$ and R$^{5b}$ on the same carbon atom may be taken together to form oxo, thioxo or a substituted or unsubstituted Spiro ring;

R$^{5c}$ is hydrogen, substituted or unsubstituted alkyl, substituted or unsubstituted alkylcarbonyl, substituted or unsubstituted alkyloxycarbonyl, substituted or unsubstituted carbamoyl, substituted or unsubstituted aromatic carbocyclylcarbonyl, substituted or unsubstituted nonaromatic carbocyclylcarbonyl, substituted or unsubstituted aromatic heterocyclylcarbonyl, substituted or unsubstituted nonaromatic heterocyclylcarbonyl, substituted or unsubstituted aromatic carbocyclyloxycarbonyl, substituted or unsubstituted nonaromatic carbocyclyloxycarbonyl, substituted or unsubstituted aromatic heterocyclyloxycarbonyl, or substituted or unsubstituted nonaromatic heterocyclyloxycarbonyl;

R$^{5d}$ is hydrogen, substituted or unsubstituted alkyl, substituted or unsubstituted alkylcarbonyl, substituted or unsubstituted alkyloxycarbonyl, substituted or unsubstituted carbamoyl, substituted or unsubstituted aromatic carbocyclylcarbonyl, substituted or unsubstituted nonaromatic carbocyclylcarbonyl, substituted or unsubstituted aromatic heterocyclylcarbonyl, substituted or unsubstituted nonaromatic heterocyclylcarbonyl, substituted or unsubstituted aromatic carbocyclyloxycarbonyl, substituted or unsubstituted nonaromatic carbocyclyloxycarbonyl, substituted or unsubstituted aromatic heterocyclyloxycarbonyl, or substituted or unsubstituted nonaromatic heterocyclyloxycarbonyl; and R$^3$ and R$^4$, or R$^3$ and a substituent on Z$^1$ may be taken together with the adjacent atoms to form a substituted or unsubstituted heterocycle.

[3'] The compound according to or a pharmaceutically acceptable salt thereof, wherein ring A is any of the following rings:

[Chemical Formula 8]

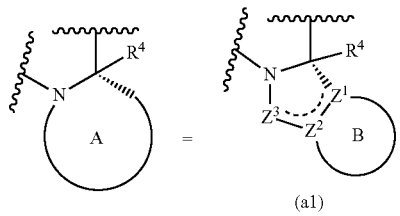

(a1)

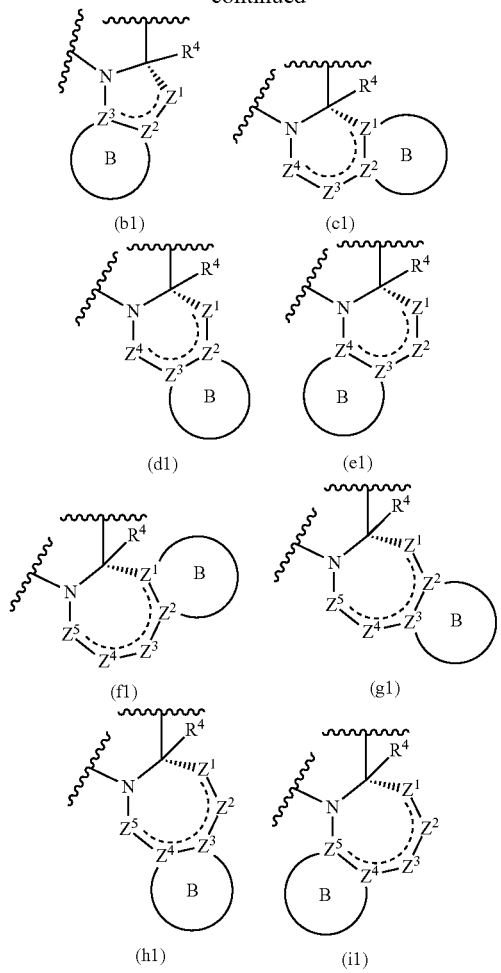

wherein
R$^4$ is hydrogen, or substituted or unsubstituted alkyl;
the broken line represents the presence or absence of a bond;
ring B is a substituted or unsubstituted carbocycle, or a substituted or unsubstituted heterocycle;
Z$^1$, Z$^2$, Z$^3$, Z$^4$ and Z$^5$ are each independently CR$^{5a}$R$^{5b}$, CR$^{5a}$, C, O, N, NR$^{5c}$, S, S(=O), S(=O)$_2$, or S(=O)=NR$^{5c}$ (provided that an atom constituting ring B is CR$^{5a}$, C, or N);
Z$^1$ and Z$^3$, Z$^1$ and Z$^4$, Z$^1$ and Z$^5$, Z$^2$ and Z$^4$, Z$^2$ and Z$^5$, Z$^3$ and Z$^5$, R$^4$ and Z$^2$, R$^4$ and Z$^3$, R$^4$ and Z$^4$, or R$^4$ and Z$^5$ may be taken together to form a substituted or unsubstituted C2-C4 cross-link;
R$^{5a}$ and R$^{5b}$ are each independently hydrogen, halogen, hydroxy, substituted or unsubstituted alkyl, substituted or unsubstituted alkyloxy, substituted or unsubstituted alkyloxycarbonyl, substituted or unsubstituted amino, substituted or unsubstituted carbamoyl, substituted or unsubstituted ureido, substituted or unsubstituted aromatic carbocyclyl, substituted or unsubstituted nonaromatic carbocyclyl, substituted or unsubstituted aromatic heterocyclyl, substituted or unsubstituted nonaromatic heterocyclyl, substituted or unsubstituted aromatic carbocyclyloxy, substituted or unsubstituted nonaromatic carbocyclyloxy, substituted or unsubstituted aromatic heterocyclyloxy, or substituted or unsubstituted nonaromatic heterocyclyloxy;

$R^{5a}$ and $R^{5b}$ on the same carbon atom may be taken together to form oxo, thioxo or a substituted or unsubstituted Spiro ring;

$R^{5c}$ is hydrogen, substituted or unsubstituted alkyl, substituted or unsubstituted alkylcarbonyl, substituted or unsubstituted alkyloxycarbonyl, substituted or unsubstituted carbamoyl, substituted or unsubstituted aromatic carbocyclylcarbonyl, substituted or unsubstituted nonaromatic carbocyclylcarbonyl, substituted or unsubstituted aromatic heterocyclylcarbonyl, substituted or unsubstituted nonaromatic heterocyclylcarbonyl, substituted or unsubstituted aromatic carbocyclyloxycarbonyl, substituted or unsubstituted nonaromatic carbocyclyloxycarbonyl, substituted or unsubstituted aromatic heterocyclyloxycarbonyl, or substituted or unsubstituted nonaromatic heterocyclyloxycarbonyl; and $R^3$ and $R^4$, or $R^3$ and a substituent on $Z^1$ may be taken together with the adjacent atoms to form a substituted or unsubstituted heterocycle.

[4'] The compound according to any one of [1'] to [3'] or a pharmaceutically acceptable salt thereof, wherein the compound is represented by the following formula (I-2):

[Chemical Formula 9]

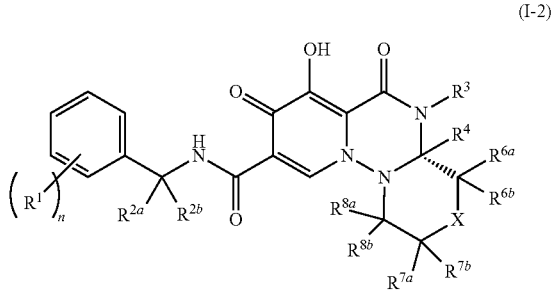

(I-2)

wherein
- $R^3$ is substituted or unsubstituted alkyl, substituted or unsubstituted nonaromatic carbocyclyl, or substituted or unsubstituted nonaromatic heterocyclyl;
- $R^4$ is hydrogen, or substituted or unsubstituted alkyl;
- X is $CR^{9a}R^{9b}$, $NR^{10}$, O, S, $S(=O)$, $S(=O)_2$, or $S(=O)=NR^{11}$;
- $R^{6a}$, $R^{6b}$, $R^{7a}$, $R^{7b}$, $R^{8a}$, $R^{8b}$, $R^{9a}$, and $R^{9b}$ are each independently hydrogen, halogen, hydroxy, substituted or unsubstituted alkyl, substituted or unsubstituted alkyloxy, or substituted or unsubstituted amino;
- $R^{6b}$ and $R^{9b}$, $R^{9b}$ and $R^{7b}$, or $R^{7b}$ and $R^{8b}$ may be taken together with the adjacent atoms to form a substituted or unsubstituted carbocycle or a substituted or unsubstituted heterocycle;
- $R^4$ and $R^{7b}$, or $R^{6b}$ and $R^{8b}$ may be taken together to form a substituted or unsubstituted C2-C4 cross-link;
- $R^{6b}$ and $R^{10}$, or $R_{10}$ and $R^{7b}$ may be taken together with the adjacent atoms to form a substituted or unsubstituted heterocycle;
- $R^3$ and $R^4$, or $R^3$ and $R^{6b}$ may be taken together with the adjacent atoms to form a substituted or unsubstituted heterocycle;
- $R^{10}$ is substituted or unsubstituted alkyl, substituted or unsubstituted alkylcarbonyl, substituted or unsubstituted alkyloxycarbonyl, substituted or unsubstituted carbamoyl, substituted or unsubstituted aromatic carbocyclylcarbonyl, substituted or unsubstituted nonaromatic carbocyclylcarbonyl, substituted or unsubstituted aromatic heterocyclylcarbonyl, substituted or unsubstituted nonaromatic heterocyclylcarbonyl, substituted or unsubstituted aromatic carbocyclyloxycarbonyl, substituted or unsubstituted nonaromatic carbocyclyloxycarbonyl, substituted or unsubstituted aromatic heterocyclyloxycarbonyl, or substituted or unsubstituted nonaromatic heterocyclyloxycarbonyl;
- $R^{11}$ is substituted or unsubstituted alkyl, substituted or unsubstituted alkylcarbonyl, substituted or unsubstituted alkyloxycarbonyl, substituted or unsubstituted carbamoyl, substituted or unsubstituted aromatic carbocyclylcarbonyl, substituted or unsubstituted nonaromatic carbocyclylcarbonyl, substituted or unsubstituted aromatic heterocyclylcarbonyl, substituted or unsubstituted nonaromatic heterocyclylcarbonyl, substituted or unsubstituted aromatic carbocyclyloxycarbonyl, substituted or unsubstituted nonaromatic carbocyclyloxycarbonyl, substituted or unsubstituted aromatic heterocyclyloxycarbonyl, or substituted or unsubstituted nonaromatic heterocyclyloxycarbonyl; and
- $R^1$, $R^{2a}$, $R^{2b}$ and n are as the same defined in [1'].

[5'] The compound according to any one of [1'] to [4'] or a pharmaceutic ally acceptable salt thereof, wherein $R^3$ is alkyl or haloalkyl.

[6'] The compound according to any one of [1'] to [5'] or a pharmaceutically acceptable salt thereof, wherein $R^4$ is hydrogen.

[7'] The compound according to any one of [1'] to [6'] or a pharmaceutically acceptable salt thereof, wherein n is an integer of 2 or 3, and $R^1$ is each independently halogen, alkyl, or haloalkyl.

[8'] The compound according to any one of [1'] to [7'] or a pharmaceutically acceptable salt thereof, wherein $R^{2a}$ is hydrogen, and $R^{2b}$ is hydrogen or alkyl, or $R^{2a}$ and $R^{2b}$ are taken together with the adjacent carbon atom to form a C3-C4 carbocycle.

[9'] The compound according to [1'] or a pharmaceutically acceptable salt thereof, wherein the compound is selected from the group consisting of the following compounds:

[Chemical Formula 10]

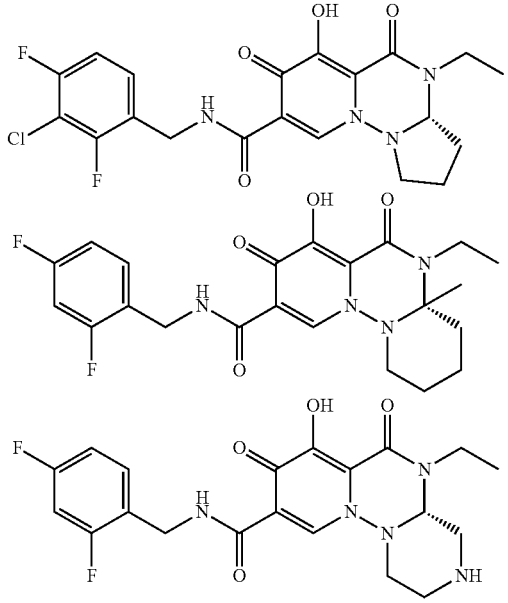

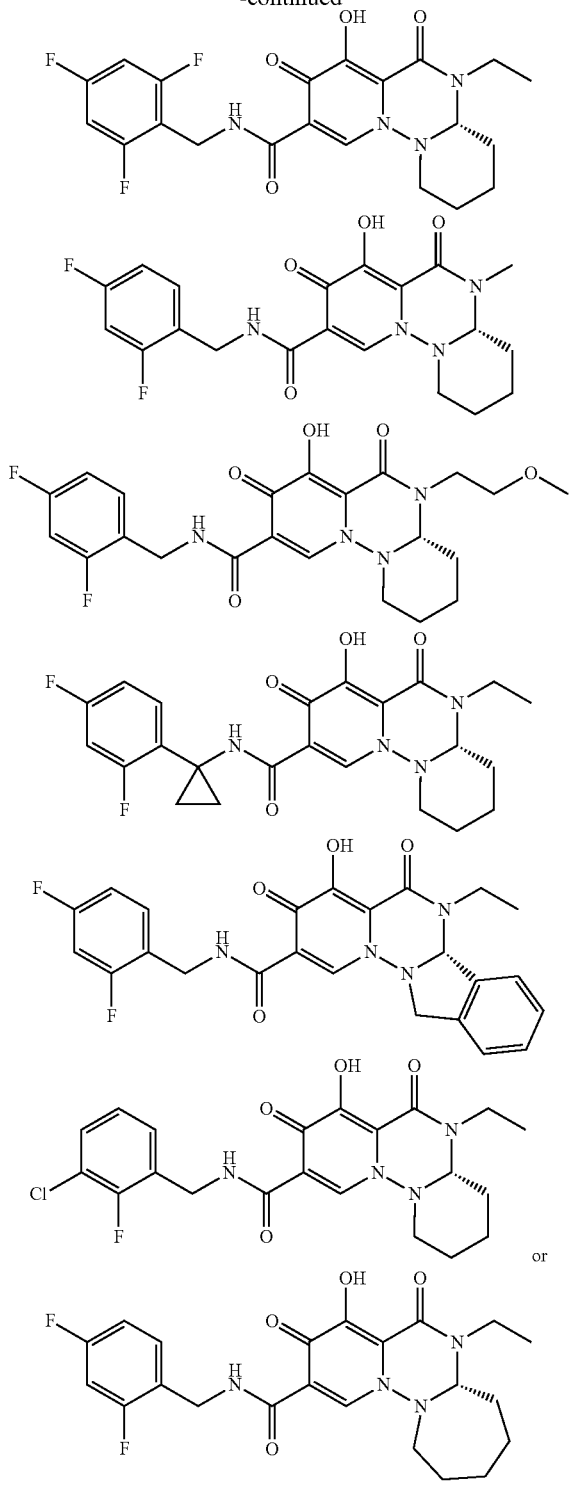

[10'] A pharmaceutical composition comprising the compound according to any one of [1'] to [9'] or a pharmaceutically acceptable salt thereof.
[11'] The pharmaceutical composition according to [10'], wherein the pharmaceutical composition is an anti-HIV agent.
[12'] The pharmaceutical composition according to [10'], wherein the pharmaceutical composition is an HIV integrase inhibitor.

The present invention further provides a method for preventing or treating HIV, comprising administering an effective amount of the above compound to a human.

The present invention further provides the above compound for use as an anti-HIV drug.

Effect of the Invention

The compound of the present invention has integrase inhibitory activity and/or cell growth inhibitory activity against a virus, particularly, HIV or a resistant virus thereof. Accordingly, the compound of the present invention is useful in the prevention or treatment of various diseases, virus infections (e.g., AIDS), and the like involving integrase. More preferably, the compound of the present invention is useful as a long-acting integrase inhibitor. Furthermore, the compound of the present invention is also excellent in resistance profile that the compound cannot easily cause a new HIV-resistant virus, and the like. Further preferably, the compound of the present invention also has a prophylactic or therapeutic effect on an HIV drug-resistant virus. Still further preferably, the compound of the present invention has small clearance, a long in vivo half-life, and excellent solubility, metabolic stability, or bioavailability, etc. and is also useful as a medicament with less concerns about cytotoxicity or a side effect (e.g., mutagenicity, the QT interval prolongation of the electrocardiogram, and arrhythmia).

MODE FOR CARRYING OUT THE INVENTION

The meaning of each term used in the present description is explained below. Each term is used in a unified sense, and is used in the same sense when used alone, or when used in combination with other terms, unless otherwise specified.

The term "consisting of" means having only components.

The term "comprising" means not restricting with components and not excluding undescribed factors.

The term "halogen" includes a fluorine atom, a chlorine atom, a bromine atom, and an iodine atom. Particularly, a fluorine atom and a chlorine atom are preferred.

The term "alkyl" includes a C1 to C15, preferably C1 to C10, more preferably C1 to C6, further preferably C1 to C4, linear or branched hydrocarbon group. Examples thereof include methyl, ethyl, n-propyl, isopropyl, n-butyl, isobutyl, sec-butyl, tert-butyl, n-pentyl, isopentyl, neopentyl, n-hexyl, isohexyl, n-heptyl, isoheptyl, n-octyl, isooctyl, n-nonyl, and n-decyl.

Examples of preferred embodiments of "alkyl" include methyl, ethyl, n-propyl, isopropyl, n-butyl, isobutyl, sec-butyl, tert-butyl, and n-pentyl. Examples of more preferred embodiments include methyl, ethyl, n-propyl, isopropyl, and tert-butyl.

The term "alkenyl" includes a C2 to C15, preferably C2 to C10, more preferably C2 to C6, further preferably C2 to C4, linear or branched hydrocarbon group having one or more double bond(s) at any position(s). Examples thereof include vinyl, allyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl, undecenyl, dodecenyl, tridecenyl, tetradecenyl, and pentadecenyl.

Examples of preferred embodiments of "alkenyl" include vinyl, allyl, propenyl, isopropenyl, and butenyl.

The term "aromatic carbocyclyl" means a cyclic aromatic hydrocarbon group which is monocyclic or polycyclic having two or more rings. Examples thereof include phenyl, naphthyl, anthryl, and phenanthryl.

Examples of preferred embodiments of "aromatic carbocyclyl" include phenyl.

The term "nonaromatic carbocyclyl" means a cyclic saturated hydrocarbon group or a cyclic unsaturated nonaromatic hydrocarbon group, which is monocyclic or polycyclic having two or more rings. The "nonaromatic carbocyclyl", which is polycyclic having two or more rings, includes a fused ring group wherein a nonaromatic carbocyclyl, which is monocyclic or polycyclic having two or more rings, is fused with a ring of the above "aromatic carbocyclyl".

In addition, the "nonaromatic carbocyclyl" also includes a group having a cross-link or a group forming a Spiro ring as follows:

[Chemical Formula 11]

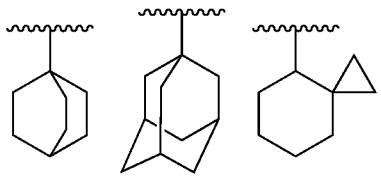

The nonaromatic carbocyclyl which is monocyclic is preferably C3 to C16, more preferably C3 to C12, further preferably C4 to C8 carbocyclyl. Examples thereof include cyclopropyl, cyclobutyl, cyclopentyl, cyclohexyl, cycloheptyl, cyclooctyl, cyclononyl, cyclodecyl, cyclopropenyl, cyclobutenyl, cyclopentenyl, cyclohexenyl, cycloheptenyl, and cyclohexadienyl.

The nonaromatic carbocyclyl which is polycyclic having two or more rings is preferably C8 to C20, and more preferably C8 to $C_{16}$ carbocyclyl. Examples thereof include indanyl, indenyl, acenaphthyl, tetrahydronaphthyl, and fluorenyl.

The term "aromatic heterocyclyl" means an aromatic cyclyl, which is monocyclic or polycyclic having two or more rings, containing one or more and same or different heteroatoms selected independently from O, S and N.

The aromatic heterocyclyl, which is polycyclic having two or more rings, includes a fused ring group wherein an aromatic heterocyclyl, which is monocyclic or polycyclic having two or more rings, is fused with a ring of the above "aromatic carbocyclyl". The bond may be present on any of the rings.

The aromatic heterocyclyl, which is monocyclic, is preferably 5- to 8-membered, more preferably 5- to 6-membered aromatic heterocyclyl. Examples of the 5-membered aromatic heterocyclyl include pyrrolyl, imidazolyl, pyrazolyl, triazolyl, tetrazolyl, furyl, thienyl, isoxazolyl, oxazolyl, oxadiazolyl, isothiazolyl, thiazolyl, and thiadiazolyl. Examples of the 6-membered aromatic heterocyclyl include pyridyl, pyridazinyl, pyrimidinyl, pyrazinyl, and triazinyl.

The aromatic heterocyclyl, which is bicyclic, is preferably 8- to 10-membered, more preferably 9- or 10-membered aromatic heterocyclyl. Examples thereof include indolyl, isoindolyl, indazolyl, indolizinyl, quinolinyl, isoquinolinyl, cinnolinyl, phthalazinyl, quinazolinyl, naphthyridinyl, quinoxalinyl, purinyl, pteridinyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, oxazolopyridyl, and thiazolopyridyl.

The aromatic heterocyclyl, which is polycyclic having three or more rings, is preferably 13- to 15-membered aromatic heterocyclyl. Examples thereof include carbazolyl, acridinyl, xanthenyl, phenothiazinyl, phenoxathiinyl, phenoxazinyl, and dibenzofuryl.

The term "nonaromatic heterocyclyl" means nonaromatic cyclyl, which is monocyclic or polycyclic having two or more rings, containing one or more and same or different heteroatoms selected independently from O, S and N in the ring. The nonaromatic heterocyclyl, which is polycyclic having two or more rings, includes a fused ring group wherein nonaromatic heterocyclyl, which is monocyclic or polycyclic having two or more rings, is fused with a ring of the "aromatic carbocyclyl", the "nonaromatic carbocyclyl", and/or the "aromatic heterocyclyl" described above, and further includes a fused ring group wherein nonaromatic carbocyclyl, which is monocyclic or polycyclic having two or more rings, is fused with a ring of the above "aromatic heterocyclyl". The bond may be present on any of the rings.

The "nonaromatic heterocyclyl" also includes a group having a cross-link or a group to form a spiro ring as follows:

[Chemical Formula 12]

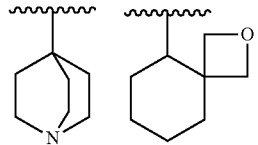

The nonaromatic heterocyclyl, which is monocyclic, is preferably 3- to 8-membered, more preferably 5- or 6-membered nonaromatic heterocyclyl.

Examples of the 3-membered nonaromatic heterocyclyl include thiiranyl, oxiranyl, and aziridinyl. Examples of the 4-membered nonaromatic heterocyclyl include oxetanyl and azetidinyl. Examples of the 5-membered nonaromatic heterocyclyl include oxathiolanyl, thiazolidinyl, pyrrolidinyl, pyrrolinyl, imidazolidinyl, imidazolinyl, pyrazolidinyl, pyrazolinyl, tetrahydrofuryl, dihydrothiazolyl, tetrahydroisothiazolyl, dioxolanyl, dioxolyl, and thiolanyl. Examples of the 6-membered nonaromatic heterocyclyl include dioxanyl, thianyl, piperidinyl, piperazinyl, morpholinyl, morpholino, thiomorpholinyl, thiomorpholino, dihydropyridyl, tetrahydropyridyl, tetrahydropyranyl, dihydrooxazinyl, tetrahydropyridazinyl, hexahydropyrimidinyl, dioxazinyl, thiinyl, and thiazinyl. Examples of the 7-membered nonaromatic heterocyclyl include hexahydroazepinyl, tetrahydrodiazepinyl, and oxepanyl.

The nonaromatic heterocyclyl, which is polycyclic having two or more rings, is preferably 8- to 20-membered, more preferably 8- to 10-membered nonaromatic heterocyclyl. Examples thereof include indolinyl, isoindolinyl, chromanyl, and isochromanyl.

The terms "aromatic carbocycle", "nonaromatic carbocycle", "aromatic heterocycle" and "nonaromatic heterocycle" mean rings derived from the "aromatic carbocyclyl", the "nonaromatic carbocyclyl", the "aromatic heterocyclyl" and the "nonaromatic heterocyclyl" described above, respectively.

The term "carbocycle" means the "aromatic carbocycle" or the "nonaromatic carbocycle" described above.

The term "heterocycle" means the "aromatic heterocycle" or the "nonaromatic heterocycle" described above.

The term "spiro ring" means the "nonaromatic carbocycle" or the "nonaromatic heterocycle" described above.

In the present description, the phrase "optionally substituted by the substituent group α" means "optionally substituted by one or more groups selected from the substituent group α". The same applies to the phrases "optionally substituted by the substituent group β", "optionally substituted by the substituent group γ", and "optionally substituted by the substituent group γ'".

Examples of the substituent of the "substituted alkyl", the "substituted alkyloxy", the "substituted alkylcarbonyl", the "substituted alkyloxycarbonyl", the "substituted C1-C4 cross-link", and the "substituted C2-C4 cross-link" include the substituent group A given below. A carbon atom at any position(s) may be bonded to one or more group(s) selected from the following substituent group A.

Substituent group A: halogen, hydroxy, carboxy, formyl, formyloxy, sulfanyl, sulfino, sulfo, thioformyl, thiocarboxy, dithiocarboxy, thiocarbamoyl, cyano, nitro, nitroso, azide, hydrazino, ureido, amidino, guanidino, alkyloxy optionally substituted by the substituent group α, alkenyloxy optionally substituted by the substituent group α, alkylcarbonyloxy optionally substituted by the substituent group α, alkenylcarbonyloxy optionally substituted by the substituent group α, alkylcarbonyl optionally substituted by the substituent group α, alkenylcarbonyl optionally substituted by the substituent group α, alkyloxycarbonyl optionally substituted by the substituent group α, alkenyloxycarbonyl optionally substituted by the substituent group α, alkylsulfanyl optionally substituted by the substituent group α, alkenylsulfanyl optionally substituted by the substituent group α, alkylsulfinyl optionally substituted by the substituent group α, alkenylsulfinyl optionally substituted by the substituent group α, alkylsulfonyl optionally substituted by the substituent group α, alkenylsulfonyl optionally substituted by the substituent group α, amino optionally substituted by the substituent group β, imino optionally substituted by the substituent group β, carbamoyl optionally substituted by the substituent group β, sulfamoyl optionally substituted by the substituent group β, ureido optionally substituted by the substituent group β, aromatic carbocyclyl optionally substituted by the substituent group γ, nonaromatic carbocyclyl optionally substituted by the substituent group γ', aromatic heterocyclyl optionally substituted by the substituent group γ, nonaromatic heterocyclyl optionally substituted by the substituent group γ', aromatic carbocyclyloxy optionally substituted by the substituent group γ, nonaromatic carbocyclyloxy optionally substituted by the substituent group γ', aromatic heterocyclyloxy optionally substituted by the substituent group γ, nonaromatic heterocyclyloxy optionally substituted by the substituent group γ', aromatic carbocyclylcarbonyloxy optionally substituted by the substituent group γ, nonaromatic carbocyclylcarbonyloxy optionally substituted by the substituent group γ', aromatic heterocyclylcarbonyloxy optionally substituted by the substituent group γ, nonaromatic heterocyclylcarbonyloxy optionally substituted by the substituent group γ', aromatic carbocyclylcarbonyl optionally substituted by the substituent group γ, nonaromatic carbocyclylcarbonyl optionally substituted by the substituent group γ', aromatic heterocyclylcarbonyl optionally substituted by the substituent group γ, nonaromatic heterocyclylcarbonyl optionally substituted by the substituent group γ', aromatic carbocyclyloxycarbonyl optionally substituted by the substituent group γ, nonaromatic carbocyclyloxycarbonyl optionally substituted by the substituent group γ', aromatic heterocyclyloxycarbonyl optionally substituted by the substituent group γ, nonaromatic heterocyclyloxycarbonyl optionally substituted by the substituent group γ', aromatic carbocyclylalkyloxy optionally substituted by the substituent group γ, nonaromatic carbocyclylalkyloxy optionally substituted by the substituent group γ', aromatic heterocyclylalkyloxy optionally substituted by the substituent group γ, nonaromatic heterocyclylalkyloxy optionally substituted by the substituent group γ', aromatic carbocyclylalkyloxycarbonyl optionally substituted by the substituent group γ, nonaromatic carbocyclylalkyloxycarbonyl optionally substituted by the substituent group γ', aromatic heterocyclylalkyloxycarbonyl optionally substituted by the substituent group γ, nonaromatic heterocyclylalkyloxycarbonyl optionally substituted by the substituent group γ', aromatic carbocyclylsulfanyl optionally substituted by the substituent group γ, nonaromatic carbocyclylsulfanyl optionally substituted by the substituent group γ', aromatic heterocyclylsulfanyl optionally substituted by the substituent group γ, nonaromatic heterocyclylsulfanyl optionally substituted by the substituent group γ', aromatic carbocyclylsulfinyl optionally substituted by the substituent group γ, nonaromatic carbocyclylsulfinyl optionally substituted by the substituent group γ', aromatic heterocyclylsulfinyl optionally substituted by the substituent group γ, nonaromatic heterocyclylsulfinyl optionally substituted by the substituent group γ', aromatic carbocyclylsulfonyl optionally substituted by the substituent group γ, nonaromatic carbocyclylsulfonyl optionally substituted by the substituent group γ', aromatic heterocyclylsulfonyl optionally substituted by the substituent group γ, and nonaromatic heterocyclylsulfonyl optionally substituted by the substituent group γ'.

Substituent group α: halogen, hydroxy, carboxy, alkyloxy, haloalkyloxy, alkenyloxy, sulfanyl, cyano, nitro, and guanidino.

Substituent group β: alkyl optionally substituted by the substituent group α, alkenyl optionally substituted by the substituent group α, alkylcarbonyl optionally substituted by the substituent group α, alkenylcarbonyl optionally substituted by the substituent group α, alkylsulfanyl optionally substituted by the substituent group α, alkenylsulfanyl optionally substituted by the substituent group α, alkylsulfinyl optionally substituted by the substituent group α, alkenylsulfinyl optionally substituted by the substituent group α, alkylsulfonyl optionally substituted by the substituent group α, alkenylsulfonyl optionally substituted by the substituent group α, aromatic carbocyclyl optionally substituted by the substituent group γ, nonaromatic carbocyclyl optionally substituted by the substituent group γ', aromatic heterocyclyl optionally substituted by the substituent group γ, nonaromatic heterocyclyl optionally substituted by the substituent group γ', aromatic carbocyclylalkyl optionally substituted by the substituent group γ, nonaromatic carbocyclylalkyl optionally substituted by the substituent group γ', aromatic heterocyclylalkyl optionally substituted by the substituent group γ, nonaromatic heterocyclylalkyl optionally substituted by the substituent group γ', aromatic carbocyclylcarbonyl optionally substituted by the substituent group γ, nonaromatic carbocyclylcarbonyl optionally substituted by the substituent group γ', aromatic heterocyclylcarbonyl optionally substituted by the substituent group γ, nonaromatic heterocyclylcarbonyl optionally substituted by the substituent group γ', aromatic carbocyclyloxycarbonyl optionally substituted by the substituent group γ, nonaromatic carbocyclyloxycarbonyl optionally substituted by the substituent group γ', aromatic heterocyclyloxycarbonyl optionally substituted by the substituent group γ, aromatic carbocyclylsulfanyl optionally substituted by the substituent group γ, nonaromatic carbocyclylsulfanyl optionally substituted by the substituent group γ', aromatic heterocyclylsulfanyl optionally substituted by the substituent group γ, nonaromatic heterocyclylsulfanyl optionally substituted by the substituent group γ', aromatic carbocyclylsulfinyl optionally substituted by the substituent group γ, nonaromatic carbocyclylsulfinyl optionally substituted by the substituent group γ', aromatic heterocyclylsulfinyl optionally substituted by the substituent group γ, nonaromatic heterocyclylsulfinyl optionally substituted by the substituent group γ', aromatic carbocyclylsulfonyl optionally substituted by the substituent group γ, nonaromatic carbocyclylsulfonyl optionally substituted by the substituent group γ', aromatic heterocyclylsulfonyl optionally substituted by the substituent group γ, and nonaromatic heterocyclylsulfonyl optionally substituted by the substituent group γ'.

Substituent group γ: substituent group α, alkyl, haloalkyl, hydroxyalkyl, alkenyl, alkylcarbonyl, haloalkylcarbonyl, and alkenylcarbonyl.

Substituent group γ': substituent group γ and oxo.

Examples of the substituent on the ring of the "aromatic carbocycle" and the "aromatic heterocycle" of the "substituted carbocycle", the "substituted heterocycle", the "substituted aromatic carbocyclyl", the "substituted aromatic heterocyclyl", the "substituted aromatic carbocyclyloxy", the "substituted aromatic heterocyclyloxy", the "substituted aromatic carbocyclylcarbonyl", the "substituted aromatic heterocyclylcarbonyl", the "substituted aromatic carbocyclyloxycarbonyl" and the "substituted aromatic heterocyclyloxycarbonyl" include the substituent group B given below. An atom at any position(s) on the ring may be bonded to one or more group(s) selected from the following substituent group B.

Substituent group B: halogen, hydroxy, carboxy, formyl, formyloxy, sulfanyl, sulfino, sulfo, thioformyl, thiocarboxy, dithiocarboxy, thiocarbamoyl, cyano, nitro, nitroso, azide, hydrazino, ureido, amidino, and guanidino, alkyl optionally substituted by the substituent group α, alkenyl optionally substituted by the substituent group α, alkyloxy optionally substituted by the substituent group α, alkenyloxy optionally substituted by the substituent group α, alkylcarbonyloxy optionally substituted by the substituent group α, alkenylcarbonyloxy optionally substituted by the substituent group α, alkylcarbonyl optionally substituted by the substituent group α, alkenylcarbonyl optionally substituted by the substituent group α, alkyloxycarbonyl optionally substituted by the substituent group α, alkenyloxycarbonyl optionally substituted by the substituent group α, alkylsulfanyl optionally substituted by the substituent group α, alkenylsulfanyl optionally substituted by the substituent group α, alkylsulfinyl optionally substituted by the substituent group α, alkenylsulfinyl optionally substituted by the substituent group α, alkylsulfonyl optionally substituted by the substituent group α, alkenylsulfonyl optionally substituted by the substituent group α,
    amino optionally substituted by the substituent group β,
        imino optionally substituted by the substituent group β,
        carbamoyl optionally substituted by the substituent group β, sulfamoyl optionally substituted by the substituent group β, ureido optionally substituted by the substituent group β,
aromatic carbocyclyl optionally substituted by the substituent group γ, nonaromatic carbocyclyl optionally substituted by the substituent group γ', aromatic heterocyclyl optionally substituted by the substituent group γ, nonaromatic heterocyclyl optionally substituted by the substituent group γ', aromatic carbocyclyloxy optionally substituted by the substituent group γ, nonaromatic carbocyclyloxy optionally substituted by the substituent group γ', aromatic heterocyclyloxy optionally substituted by the substituent group γ, nonaromatic heterocyclyloxy optionally substituted by the substituent group γ', aromatic carbocyclylcarbonyloxy optionally substituted by the substituent group γ, nonaromatic carbocyclylcarbonyloxy optionally substituted by the substituent group γ', aromatic heterocyclylcarbonyloxy optionally substituted by the substituent group γ, nonaromatic heterocyclylcarbonyloxy optionally substituted by the substituent group γ', aromatic carbocyclylcarbonyl optionally substituted by the substituent group γ, nonaromatic carbocyclylcarbonyl optionally substituted by the substituent group γ', aromatic heterocyclylcarbonyl optionally substituted by the substituent group γ, nonaromatic heterocyclylcarbonyl optionally substituted by the substituent group γ', aromatic carbocyclyloxycarbonyl optionally substituted by the substituent group γ, nonaromatic carbocyclyloxycarbonyl optionally substituted by the substituent group γ', aromatic heterocyclyloxycarbonyl optionally substituted by the substituent group γ, nonaromatic heterocyclyloxycarbonyl optionally substituted by the substituent group γ', aromatic carbocyclylalkyl optionally substituted by the substituent group γ, nonaromatic carbocyclylalkyl optionally substituted by the substituent group γ', aromatic heterocyclylalkyl optionally substituted by the substituent group γ, nonaromatic heterocyclyl alkyl optionally substituted by the substituent group γ', aromatic carbocyclylalkyloxy optionally substituted by the substituent group γ, nonaromatic carbocyclylalkyloxy optionally substituted by the substituent group γ', aromatic heterocyclylalkyloxy optionally substituted by the substituent group γ, nonaromatic heterocyclylalkyloxy optionally substituted by the substituent group γ', aromatic carbocyclylalkyloxycarbonyl optionally substituted by the substituent group γ, nonaromatic carbocyclylalkyloxycarbonyl optionally substituted by the substituent group γ', aromatic heterocyclylalkyloxycarbonyl optionally substituted by the substituent group γ, nonaromatic heterocyclylalkyloxycarbonyl optionally substituted by the substituent group γ', aromatic carbocyclylalkyloxyalkyl optionally substituted by the substituent group γ, nonaromatic carbocyclylalkyloxyalkyl optionally substituted by the substituent group γ', aromatic heterocyclylalkyloxyalkyl optionally substituted by the substituent group γ, nonaromatic heterocyclylalkyloxyalkyl optionally substituted by the substituent group γ', aromatic carbocyclylsulfanyl optionally substituted by the substituent group γ, nonaromatic carbocyclylsulfanyl optionally substituted by the substituent group γ', aromatic heterocyclylsulfanyl optionally substituted by the substituent group γ, nonaromatic heterocyclylsulfanyl optionally substituted by the substituent group γ', aromatic carbocyclylsulfinyl optionally substituted by the substituent group γ, nonaromatic carbocyclylsulfinyl optionally substituted by the substituent group γ', aromatic heterocyclylsulfinyl optionally substituted by the substituent group γ, nonaromatic heterocyclylsulfinyl optionally substituted by the substituent group γ', aromatic carbocyclylsulfonyl optionally substituted by the substituent group γ, nonaromatic carbocyclylsulfonyl optionally substituted by the substituent group γ', aromatic heterocyclylsulfonyl optionally substituted by the substituent group γ, and nonaromatic heterocyclylsulfonyl optionally substituted by the substituent group γ'.

Examples of the substituent on the ring of the "nonaromatic carbocycle" and the "nonaromatic heterocycle" of the "substituted carbocycle", the "substituted heterocycle", the "substituted nonaromatic carbocyclyl", the "substituted nonaromatic heterocyclyl", the "substituted nonaromatic carbocyclyloxy", the "substituted nonaromatic heterocyclyloxy", the "substituted nonaromatic carbocyclylcarbonyl", the "substituted nonaromatic heterocyclylcarbonyl", the "substituted nonaromatic carbocyclyloxycarbonyl" and the "substituted nonaromatic heterocyclyloxycarbonyl" include the substituent group C given below. An atom at any position(s) on the ring may be bonded to one or more group(s) selected from the following substituent group C.

Substituent group C: substituent group B and oxo.

Examples of the substituent of the "substituted amino", the "substituted carbamoyl", and the "substituted ureido" include the substituent group D given below. The moiety is optionally substituted by 1 or 2 groups selected from the substituent group D.

Substituent group D: alkyl optionally substituted by the substituent group α, alkenyl optionally substituted by the substituent group α, alkylcarbonyl optionally substituted by the substituent group α, alkenylcarbonyl optionally substituted by the substituent group α, alkylsulfanyl optionally substituted by the substituent group α, alkenylsulfanyl optionally substituted by the substituent group α, alkylsulfinyl optionally substituted by the substituent group α, alkenylsulfinyl optionally substituted by the substituent group α, alkylsulfonyl optionally substituted by the substituent group α, alkenylsulfonyl optionally substituted by the substituent group α, aromatic carbocyclyl optionally substituted by the substituent group γ, nonaromatic carbocyclyl optionally substituted by the substituent group γ', aromatic heterocyclyl optionally substituted by the substituent group γ, nonaromatic heterocyclyl optionally substituted by the substituent group γ', aromatic carbocyclylalkyl optionally substituted by the substituent group γ, nonaromatic carbocyclylalkyl optionally substituted by the substituent group γ', aromatic heterocyclylalkyl optionally substituted by the substituent group γ, nonaromatic heterocyclylalkyl optionally substituted by the substituent group γ', aromatic carbocyclylcarbonyl optionally substituted by the substituent group γ, nonaromatic carbocyclylcarbonyl optionally substituted by the substituent group γ', aromatic heterocyclylcarbonyl optionally substituted by the substituent group γ, nonaromatic heterocyclylcarbonyl optionally substituted by the substituent group γ', aromatic carbocyclyloxycarbonyl optionally substituted by the substituent group γ, nonaromatic carbocyclyloxycarbonyl optionally substituted by the substituent group γ', aromatic heterocyclyloxycarbonyl optionally substituted by the substituent group γ, nonaromatic heterocyclyloxycarbonyl optionally substituted by the substituent group γ', aromatic carbocyclylsulfanyl optionally substituted by the substituent group γ, nonaromatic carbocyclylsulfanyl optionally substituted by the substituent group γ', aromatic heterocyclylsulfanyl optionally substituted by the substituent group γ, nonaromatic heterocyclylsulfanyl optionally substituted by the substituent group γ', aromatic carbocyclylsulfinyl optionally substituted by the substituent group γ, nonaromatic carbocyclylsulfinyl optionally substituted by the substituent group γ', aromatic heterocyclylsulfinyl optionally substituted by the substituent group γ, nonaromatic heterocyclylsulfinyl optionally substituted by the substituent group γ', aromatic carbocyclylsulfonyl optionally substituted by the substituent group γ, nonaromatic carbocyclylsulfonyl optionally substituted by the substituent group γ', aromatic heterocyclylsulfonyl optionally substituted by the substituent group γ, and nonaromatic heterocyclylsulfonyl optionally substituted by the substituent group γ'.

Preferred embodiments of each symbol in the compound represented by Formula (I) or (I') are described below. Examples of the compound represented by Formula (I) or (I') include embodiments of all combinations of specific examples given below.

Examples of ring A include substituted or unsubstituted nonaromatic heterocycles.

Ring A is preferably a 5- to 7-membered ring having 1 to 3, preferably 1 or 2( ), S and/or N atoms, more preferably a ring selected from the nonaromatic heterocycles described above. One preferred embodiment of ring A is the following ring (a), (b) or (c), more preferably ring (a) or (b):

[Chemical Formula 13]

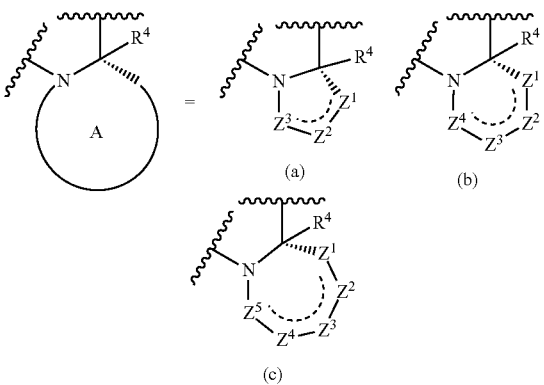

$Z^1$, $Z^2$, $Z^3$, $Z^4$ and $Z^5$ are each independently $CR^{5a}R^{5b}$, $CR^{5a}$, O, N, $NR^{5c}$, or S, wherein the number of heteroatoms constituting the ring structure of ring A in $Z^1$, $Z^2$, $Z^3$, $Z^4$ and $Z^5$ is 0 or 1.

One preferred embodiment of $Z^1$ is $CR^{5a}R^{5b}$, O, S or $NR^{5c}$, more preferably $CR^{5a}R^{5b}$.

One preferred embodiment of $Z^2$ is $CR^{5a}R^{5b}$, O, S or $NR^{5c}$, more preferably $CR^{5a}R^{5b}$, O or $NR^{5c}$, particularly preferably $CR^{5a}R^{5b}$ or O.

One preferred embodiment of $Z^3$ is $CR^{5a}R^{5b}$, O, S or $NR^{5c}$, more preferably $CR^{5a}R^{5b}$ or O, particularly preferably $CR^{5a}R^{5b}$.

One preferred embodiment of $Z^4$ is $CR^{5a}R^{5b}$, O, S or $NR^{5c}$, more preferably $CR^{5a}R^{5b}$.

One preferred embodiment of $Z^5$ is $CR^{5a}R^{5b}$, O, S or $NR^{5c}$, more preferably $CR^{5a}R^{5b}$.

Alternatively, $Z^1$ and $Z^3$, $Z^1$ and $Z^4$, $Z^1$ and $Z^5$, $Z^2$ and $Z^4$, $Z^2$ and $Z^5$, $Z^3$ and $Z^5$, $R^4$ and $Z^2$, $R^4$ and $Z^3$, $R^4$ and $Z^4$, or $R^4$ and $Z^5$ may be taken together to form a substituted or unsubstituted C1-C4 cross-link. Preferably, $Z^1$ and $Z^3$, $Z^1$ and $Z^4$, $Z^1$ and $Z^5$, $Z^2$ and $Z^4$, $Z^2$ and $Z^5$, or $Z^3$ and $Z^5$ may be taken together to form a substituted or unsubstituted (C1-C4) cross-link.

Ring A may further have ring B as shown below. In this case, $Z^1$, $Z^2$, $Z^3$, $Z^4$ and $Z^5$ constituting ring B are each independently $CR^{5a}$, C or N.

[Chemical Formula 8]

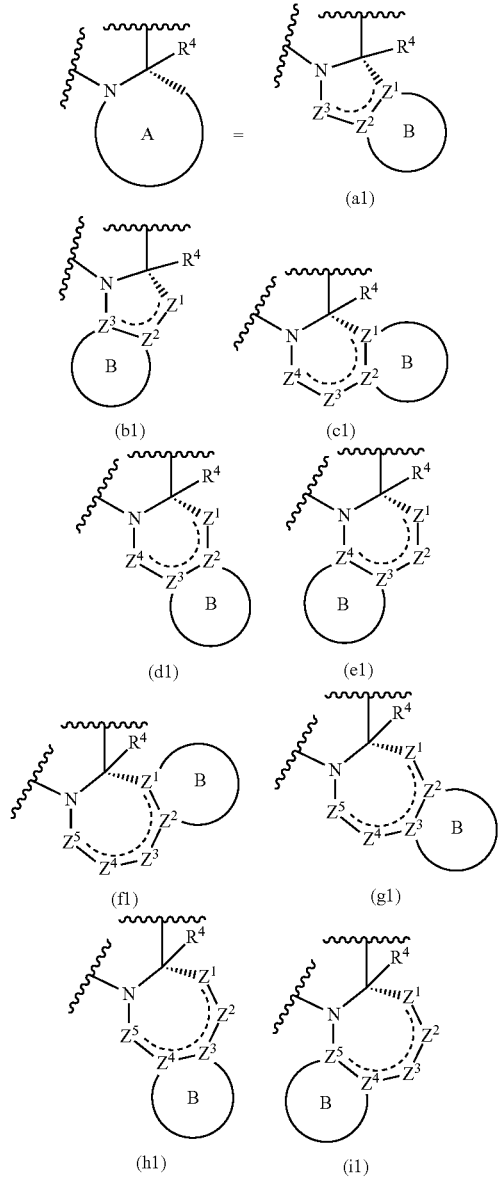

One more preferred embodiment of ring A is the following ring (a1), (b1), (c1) or (e1), particularly preferably ring (a1) or (b1).

Ring B is preferably a substituted or unsubstituted 3- to 7-membered carbocycle (wherein examples of the substituent include alkyl, halogen, hydroxy, and haloalkyl) or a substituted or unsubstituted 4- to 7-membered heterocycle (wherein examples of the substituent include alkyl, halogen, hydroxy, and haloalkyl), more preferably a benzene ring, a 5- to 6-membered unsubstituted carbocycle or a 5- to 6-membered unsubstituted heterocycle.

Examples of another preferred embodiment of ring A include the following ring:

[Chemical Formula 15]

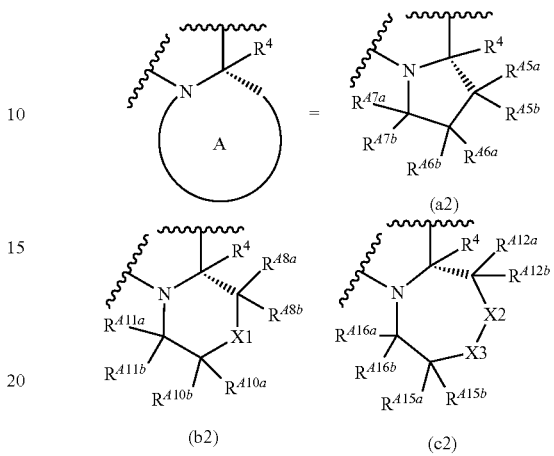

One still preferred embodiment of ring A is the following ring:

[Chemical Formula 16]

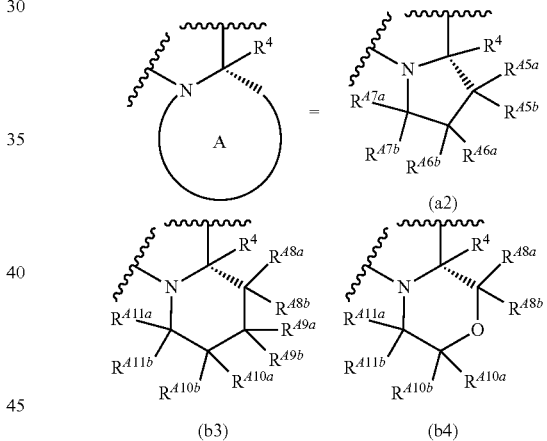

A more preferred embodiment of ring A is the above ring (a2) or (b3).

Examples of X1 include $CR^{A9a}R^{A9b}$, O, or $NR^{A9c}$.
One preferred embodiment of X1 is $CR^{A9a}R^{A9b}$ or O.
Examples of X2 include $CR^{A13a}R^{A13b}$, O, or $NR^{A13c}$.
One preferred embodiment of X2 is $CR^{A13a}R^{A13b}$ or O.
Examples of X3 include $CR^{A14a}R^{A9b}$, O, or $NR^{A14c}$.
One preferred embodiment of X3 is $CR^{A14a}R^{A14b}$ or O.
However, when either one of X2 or X3 is $NR^{A13c}$, $NR^{A14c}$, or O, the other of X2 or X3 is $CR^{A13a}R^{A13b}$ or $CR^{A14a}R^{A14b}$).

Examples of $R^{A5a}$, $R^{A5b}$, $R^{A6a}$, $R^{A6b}$, $R^{A7a}$ and $R^{A7b}$ include each independently hydrogen, alkyl, alkyloxy, or alkyloxyalkyl.
One preferred embodiment of $R^{A5a}$ is hydrogen or alkyl, preferably hydrogen.
One preferred embodiment of $R^{A5b}$ is hydrogen or alkyl, preferably hydrogen.
One preferred embodiment of $R^{A6a}$ is hydrogen, alkyl or alkyloxyalkyl, preferably hydrogen.

One preferred embodiment of $R^{A6b}$ is hydrogen.

One preferred embodiment of $R^{A7a}$ is hydrogen, alkyl or alkyloxyalkyl, preferably alkyloxyalkyl.

One preferred embodiment of $R^{A7b}$ is hydrogen.

$R^{A5a}$ and $R^{A6a}$, or $R^{A6a}$ and $R^{A7a}$ may be taken together with the adjacent atoms to form an aromatic carbocycle optionally substituted by halogen, a 3- to 6-membered nonaromatic carbocycle optionally substituted by halogen, or a 4- to 6-membered nonaromatic heterocycle optionally substituted by halogen (provided that, when forming an aromatic carbocycle, $R^{A5b}$ and $R^{A6b}$, or $R^{A6b}$ and $R^{A7b}$ are taken together to form a bond).

$R^{A5b}$ and $R^{A6b}$ may be taken together to form a bond.

$R^{A6a}$ and $R^{A6b}$ may be taken together with the adjacent atom to form a 3- to 6-membered nonaromatic carbocycle or a 4- to 6-membered nonaromatic heterocycle.

Examples of Rhu A8a, $R^{A8b}$, $R^{A9a}$, $R^{A9b}$, $R^{A10a}$, $R^{A10b}$, $R^{A11a}$ and $R^{A11b}$ include each independently hydrogen, alkyl, haloalkyl, alkyloxy, or alkyloxyalkyl.

One preferred embodiment of $R^{A8a}$ is hydrogen or alkyl, preferably hydrogen.

One preferred embodiment of $R^{A8b}$ is hydrogen or alkyl, preferably hydrogen.

One preferred embodiment of $R^{A9a}$ is hydrogen, alkyl or alkyloxyalkyl.

One preferred embodiment of $R^{A9b}$ is hydrogen or alkyl, preferably hydrogen.

One preferred embodiment of $R^{A10a}$ is hydrogen, alkyl or alkyloxy, preferably hydrogen.

One preferred embodiment of $R^{A10b}$ is hydrogen.

One preferred embodiment of $R^{A11a}$ is hydrogen or alkyl, preferably hydrogen.

One preferred embodiment of $R^{A11b}$ is hydrogen.

Rhu A8a and $R^{A10a}$, or $R^{A8a}$ and $R^{A11a}$ may be taken together to form a C1-C3 cross-link.

$R^{A9a}$ and $R^{A11a}$ may be taken together with the adjacent atoms to form a 5-membered nonaromatic carbocycle.

$R^{A9a}$ and $R^{A9b}$ may be taken together with the adjacent atoms to form a 4-membered nonaromatic carbocycle or a 5-membered nonaromatic heterocycle.

$R^{A8a}$ and $R^{A9a}$ may be taken together to form a bond.

$R^{A9c}$ is hydrogen, alkyl, alkyloxyalkyl, alkyloxycarbonyl, alkylcarbamoyl, aromatic carbocyclyl, aromatic heterocyclyl, aromatic carbocyclylalkyl, or aromatic heterocyclylalkyl.

$R^{A12a}$, $R^{A12b}$, $R^{A13a}$, $R^{A13b}$, $R^{A14a}$, $R^{A14b}$, $R^{A15a}$, $R^{A15b}$, $R^{A16a}$ and $R^{A16b}$ are each independently hydrogen, alkyl, alkyloxy, or alkyloxyalkyl.

$R^{A13c}$ or $R^{A14c}$ is each independently alkyl, alkyloxyalkyl, alkyloxycarbonyl, alkylcarbamoyl, aromatic carbocyclyl, aromatic heterocyclyl, aromatic carbocyclylalkyl, or aromatic heterocyclylalkyl.

Examples of $R^1$ include each independently halogen, alkyl, haloalkyl, alkyloxy, cyano, or haloalkyloxy.

One preferred embodiment of $R^1$ is halogen, alkyl or haloalkyl.

$R^1$ is preferably halogen.

Examples of $R^{2a}$ and $R^{2b}$ include each independently hydrogen, alkyl, and haloalkyl.

One preferred embodiment of $R^{2a}$ and $R^{2b}$ is hydrogen.

Another preferred embodiment of $R^{2a}$ and $R^{2b}$ is taken together with the adjacent carbon atom to form a carbocycle.

$R^{2a}$ is preferably hydrogen.

$R^{2b}$ is preferably hydrogen or methyl, more preferably hydrogen.

$R^{2a}$ and $R^{2b}$ are preferably taken together with the adjacent carbon atom to form a C3-C4 nonaromatic carbocycle.

$R^3$ is substituted or unsubstituted alkyl (wherein examples of the substituent include halogen, alkyloxy, haloalkyloxy, nonaromatic cyclyl, or nonaromatic heterocyclyl), substituted or unsubstituted nonaromatic carbocyclyl (wherein examples of the substituent include halogen), or substituted or unsubstituted nonaromatic heterocyclyl (wherein examples of the substituent include halogen).

One preferred embodiment of $R^3$ is alkyl or haloalkyl.

$R^3$ is preferably alkyl.

Examples of $R^4$ include hydrogen and alkyl.

One preferred embodiment of $R^4$ is hydrogen or methyl, more preferably hydrogen.

Examples of $R^{5a}$ and $R^{5b}$ include each independently hydrogen, halogen, substituted or unsubstituted alkyl (wherein examples of the substituent include halogen and alkyloxy), and substituted or unsubstituted alkyloxy (wherein examples of the substituent include halogen). $R^{5a}$ and $R^{5b}$ on the same carbon atom may be taken together to form a substituted or unsubstituted nonaromatic carbocycle (wherein examples of the substituent include halogen), or a substituted or unsubstituted nonaromatic heterocycle (wherein examples of the substituent include halogen).

One preferred embodiment of $R^{5a}$ and $R^{5b}$ is each independently hydrogen, alkyl, or alkyloxyalkyl.

Examples of $R^{5c}$ include each independently hydrogen, substituted or unsubstituted alkyl (wherein examples of the substituent include alkyloxy, aromatic carbocyclyl, and aromatic heterocyclyl), substituted or unsubstituted alkylcarbonyl, substituted or unsubstituted alkyloxycarbonyl, substituted or unsubstituted carbamoyl (wherein examples of the substituent include alkyl), substituted or unsubstituted aromatic carbocyclyl, substituted or unsubstituted nonaromatic carbocyclyl, substituted or unsubstituted aromatic heterocyclyl, or substituted or unsubstituted nonaromatic heterocyclyl.

One preferred embodiment of $R^{5c}$ is each independently hydrogen, or substituted or unsubstituted alkyl (wherein examples of the substituent include alkyloxy).

Examples of n include an integer of 1 to 3.

One preferred embodiment of n is an integer of 2 to 3.

One more preferred embodiment of n is an integer of 1 to 2.

Examples of ring C include a benzene ring, a pyridine ring, or a 5-membered aromatic heterocycle.

One preferred embodiment of ring C is a benzene ring or a pyridine ring, preferably a benzene ring.

The compound represented by Formula (I') is preferably a compound represented by the following Formula (I-2):

[Chemical Formula 17]

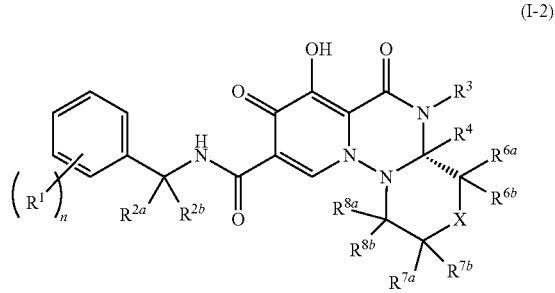

(I-2)

Preferred embodiments of each symbol in the compound represented by Formula (I-2) are described below. Examples of the compound represented by Formula (I-2) include embodiments of all combinations of specific examples given below.

$R^1$, $R^{2a}$, $R^{2b}$, $R^3$, $R^4$, and n are the same as defined in the preferred embodiments of the compound represented by Formula (I').

One preferred embodiment of X is $CR^{9a}R^{9b}$, $NR^{10}$, or O, more preferably $CR^{9a}R^{9b}$ or $NR^{10}$, particularly preferably $CR^{9a}R^{9b}$.

One preferred embodiment of $R^{6a}$, $R^{6b}$, $R^{7a}$, $R^{7b}$, $R^{8a}$, $R^{8b}$, $R^{9a}$, and $R^{9b}$ is each independently hydrogen, or substituted or unsubstituted alkyl.

$R^{6a}$, $R^{6b}$, $R^{7a}$, $R^{7b}$, $R^{8a}$, $R^{8b}$, $R^{9a}$, and $R^{9b}$ are preferably, each independently, hydrogen, or substituted or unsubstituted alkyl (wherein example of the substituent include halogen), particularly preferably hydrogen or methyl.

One preferred embodiment of $R^{10}$ is substituted or unsubstituted alkyl.

One preferred embodiment in the compound represented by Formula (I) is described below.

Ring A is the following ring:

[Chemical Formula 18]

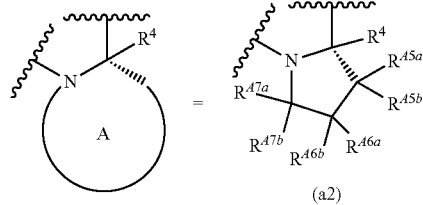

(a2)

wherein
$R^{A5a}$, $R^{A5b}$, $R^{A6a}$, $R^{A6b}$, $R^{A7a}$ and $R^{A7b}$ are each independently hydrogen, alkyl, alkyloxy, or alkyloxyalkyl;
$R^{A5a}$ and $R^{A6a}$, or $R^{A6a}$ and $R^{A7a}$ may be taken together with the adjacent atoms to form an aromatic carbocycle optionally substituted by halogen, a 3- to 6-membered nonaromatic carbocycle optionally substituted by halogen, or a 4- to 6-membered nonaromatic heterocycle optionally substituted by halogen (provided that, when forming an aromatic carbocycle, $R^{A5b}$ and $R^{A6b}$, or $R^{A6b}$ and $R^{A7b}$ is taken together to form a bond);
ring C is a benzene ring;
$R^1$ is each independently halogen;
$R^{2a}$ and $R^{2b}$ are each independently hydrogen;
$R^3$ is alkyl;
$R^4$ is hydrogen or alkyl; and
n is an integer of 1 to 3.

A feature of the compound of the present invention is that ring A in Formula (I), (I') or (I-2) is fixed to a specific conformation to attain excellent resistance profile, in vivo kinetics and safety. Another feature of the compound of the present invention is that an optically active tricyclic or more polycyclic carbamoylpyridotriazine derivative is obtained in Formula (I), (I') or (I-2) to attain excellent resistance profile, in vivo kinetics and safety.

The compound of the present invention is not limited to a specific isomer and includes all possible isomers (e.g., keto-enol isomers, imine-enamine isomers, diastereomers, optical isomers, and rotational isomers), racemates or mixtures thereof, unless otherwise specified.

Examples of the pharmaceutically acceptable salt of the compound of the present invention include salts of the compound of the present invention with alkali metals (e.g., lithium, sodium, or potassium), alkaline earth metals (e.g., calcium, or barium), magnesium, transition metals (e.g., zinc and iron), ammonia, organic bases (e.g., trimethylamine, triethylamine, dicyclohexylamine, ethanolamine, diethanolamine, triethanolamine, meglumine, ethylenediamine, pyridine, picoline, or quinoline) or amino acids, and salts of the compound of the present invention with inorganic acids (e.g., hydrochloric acid, sulfuric acid, nitric acid, carbonic acid, hydrobromic acid, phosphoric acid, or hydroiodic acid) or organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, or ethanesulfonic acid). These salts can be formed by the method which is usually performed.

The compound of the present invention or a pharmaceutically acceptable salt thereof may form a solvate (e.g., a hydrate), a cocrystal and/or a crystal polymorph. The present invention also encompasses such various solvates, cocrystals and crystal polymorphs. The "solvate" may be a solvate wherein any number of solvent molecules (e.g., water molecules) are coordinated with the compound of the present invention. The compound of the present invention or a pharmaceutically acceptable salt thereof, when left standing in the atmosphere, may attach adsorbed water or may form a hydrate, by absorbing moisture. The compound of the present invention or a pharmaceutically acceptable salt thereof may form a crystal polymorph by recrystallization. The "cocrystal" means that the compound of the present invention or a salt thereof and a counter molecule coexist in the same crystal lattice, and may be a cocrystal formed with any number of counter molecules.

The compound of the present invention or a pharmaceutically acceptable salt thereof may form a prodrug. The present invention also encompasses such various prodrugs. The prodrug is a derivative of the compound of the present invention having a chemically or metabolically decomposable group, and is a compound that becomes the pharmaceutically active compound of the present invention by solvolysis or under physiological conditions in vivo. The prodrug includes, for example, a compound that is converted to the compound represented by Formula (I), (I') or (I-2) through enzymatic oxidation, reduction, hydrolysis, or the like under physiological conditions in vivo, and a compound that is converted to the compound represented by Formula (I), (I') or (I-2) through hydrolysis by gastric acid or the like. Methods for selecting and preparing suitable prodrug derivatives are described in, for example, "Design of Prodrugs, Elsevier, Amsterdam, 1985". Prodrugs themselves may have some activity.

When the compound represented by Formula (I), (I') or (I-2) or a pharmaceutically acceptable salt thereof has a hydroxyl group, examples of the prodrug include prodrugs such as acyloxy derivatives and sulfonyloxy derivatives produced by reacting the compound having a hydroxyl group with an appropriate acyl halide, an appropriate acid anhydride, an appropriate sulfonyl chloride, an appropriate sulfonyl anhydride and a mixed anhydride, or using a condensing agent. Examples thereof include $CH_3COO—$, $C_2H_5COO—$, tert-BuCOO—, $C_{15}H_{31}COO-$, PhCOO—, (m-NaOOCPh)COO—, $NaOOCCH_2CH_2COO—$, $CH_3CH(NH_2)COO—$, $CH_2N(CH_3)_2COO—$, $CH_3SO_3—$, $CH_3CH_2SO_3—$, $CF_3SO_3—$, $CH_2FSO_3—$, $CF_3CH_2SO_3—$, p-$CH_3O$-$PhSO_3—$, $PhSO_3—$, and p-$CH_3PhSO_3—$.

(Method for Producing Compound of Present Invention)

The compound of the present invention can be produced by, for example, general synthesis methods shown below. The methods for extraction, purification, and the like may be carried out by using the usual methods for the experiments of organic chemistry.

The compound of the present invention can be synthesized by referring to the methods known in the art.

(Process 1)

[Chemical Formula 19]

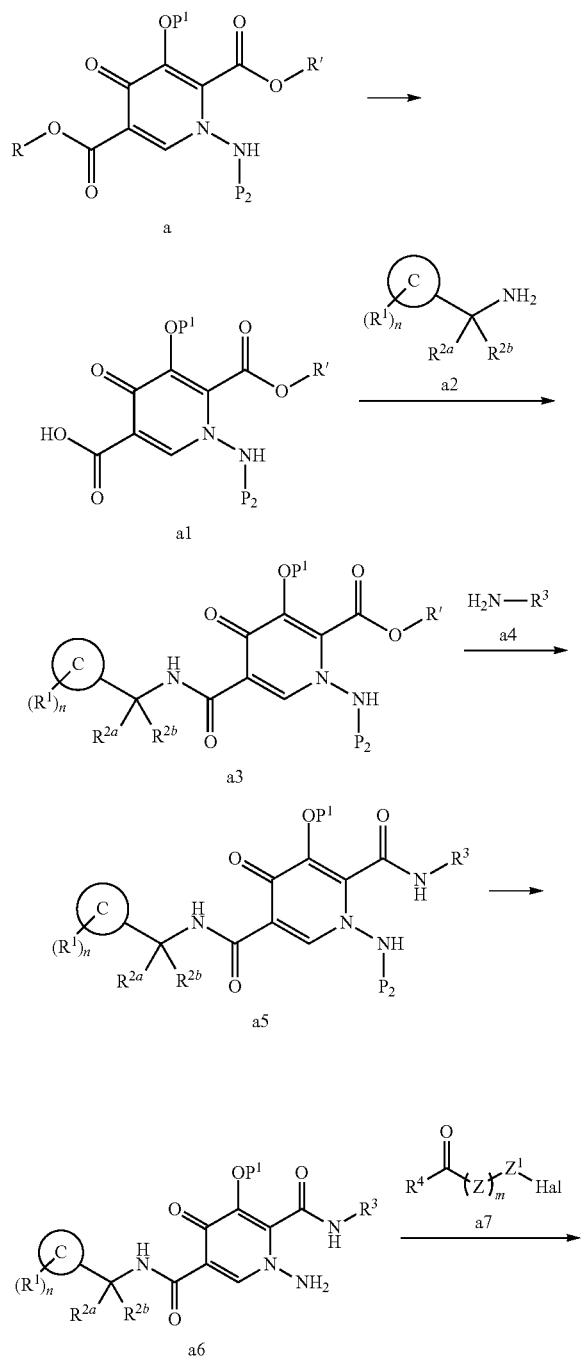

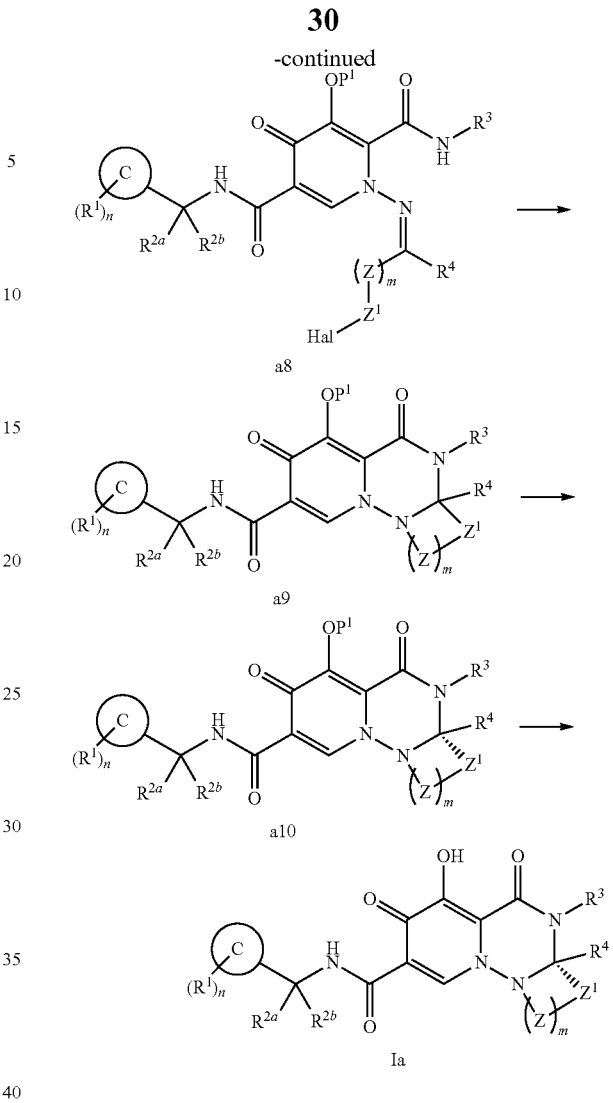

wherein $P^1$ is a hydroxy-protective group; $P^2$ is an amino-protective group; each of R and R' is a carboxy-protective group; Z is $Z^2$, $Z^3$, $Z^4$ or $Z^5$; m is an integer of 1 to 4; Hal is halogen; each of $P^1$, $P^2$, R and R' can be a group that can be protected and/or deprotected by a method described in, for example, Protective Groups in Organic Synthesis, Theodora W Green (John Wiley & Sons Inc.), and, for example, $P^1$ is aromatic carbocyclylalkyl or the like, $P^2$ is alkyloxycarbonyl or the like, and each of R and R' is alkyl or the like; and the other symbols are the same as defined above.

Step 1

Compound a1 can be obtained by subjecting compound a which can be commercially available or prepared by a known method to the general deprotection reaction of carboxy-protective groups.

Step 2

Compound a3 can be obtained by adding a condensing agent such as HATU, WSC·HCl, or PyBOP to compound a1 in the presence of a solvent such as DMF, DMA, NMP, THF, chloroform, or dichloromethane, adding thereto compound a2 which can be commercially available or prepared by a known method, and a tertiary amine such as triethylamine, N-methylmorpholine, pyridine, or DIEA, and reacting the mixture at 10° C. to 60° C., preferably 20° C. to 40° C., for 0.1 hours to 24 hours, preferably 1 hour to 12 hours.

Step 3

Compound a5 can be obtained by adding compound a4 to compound a3 in the presence of a solvent such as THF, methanol, ethanol, chloroform, dichloromethane, or THF, and reacting the mixture at 60° C. to 120° C., preferably 80° C. to 100° C., for 0.5 hours to 24 hours, preferably 1 hour to 12 hours.

Step 4

Compound a6 can be obtained by subjecting compound a5 to the general deprotection reaction of amino-protective groups.

Step 5

Compound a8 can be obtained by adding compound a7 which can be commercially available or prepared by a known method, and an acid such as acetic acid, p-toluenesulfonic acid, or methanesulfonic acid to compound a6 in the presence of a solvent such as dichloromethane, dichloroethane, chloroform, methanol, ethanol, toluene, DMF, DMA, or THF, and reacting the mixture at 20° C. to 130° C., preferably 20° C. to 100° C., for 0.1 hours to 24 hours, preferably 1 hour to 12 hours.

Step 6

Compound a9 can be obtained by adding a base such as cesium carbonate or potassium carbonate and a salt such as sodium iodide or potassium iodide to compound a8 in the presence of a solvent such as DMF, DMA, NMP, or THF, and reacting the mixture at 0° C. to 60° C., preferably 0° C. to 40° C., for 0.1 hours to 24 hours, preferably 1 hour to 12 hours.

Step 7

Compound a9 can be resolved into compound a10 by chiral SFC.

Step 8

Compound Ia can be obtained by subjecting compound a10 to the general deprotection reaction of hydroxy-protective groups.

(Process 2)

[Chemical Formula 20]

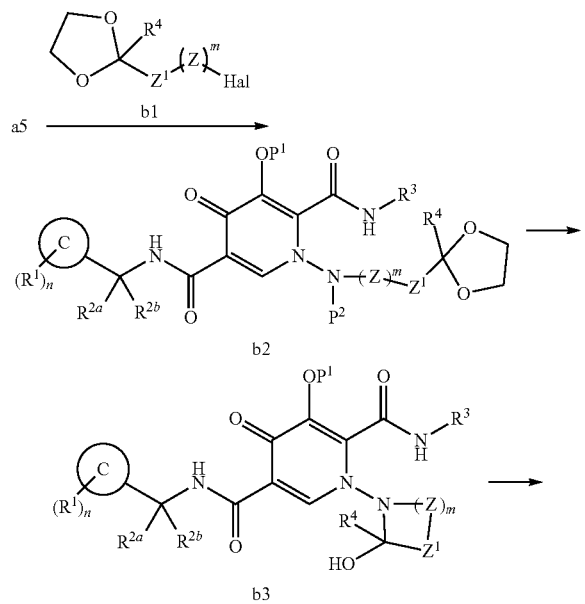

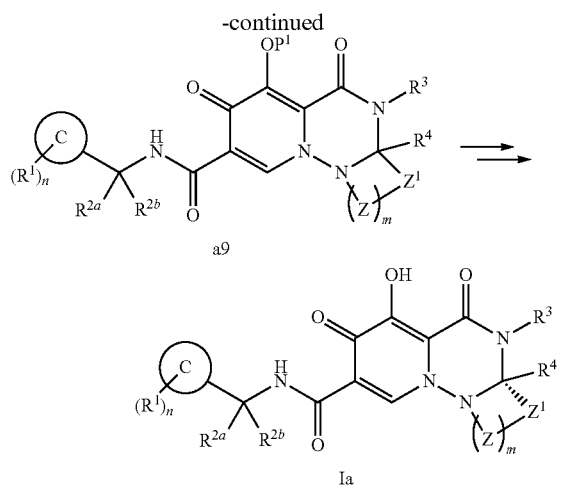

wherein each symbol is the same as defined above.

Step 1

Compound b2 can be obtained by adding a base such as cesium carbonate, potassium carbonate, or triethylamine and, when Hal is chloro, a salt such as sodium iodide or potassium iodide to compound a5 in the presence of a solvent such as DMF, DMA, NMP, or THF, adding thereto compound b1 which can be commercially available or prepared by a known method, and reacting the mixture at 0° C. to 60° C., preferably 20° C. to 40° C., for 0.1 hours to 24 hours, preferably 1 hour to 12 hours.

Step 2

Compound b3 can be obtained by subjecting compound b2 to the general deprotection reaction of acetals.

Step 3

Compound a9 can be obtained by adding an acid such as acetic acid, p-toluenesulfonic acid, methanesulfonic acid, or trifluoroacetic acid to compound b3 in the presence of a solvent such as dichloromethane, dichloroethane, chloroform, acetonitrile, methanol, ethanol, toluene, DMF, DMA, or THF, and reacting the mixture at 20° C. to 130° C., preferably 80° C. to 120° C., for 0.1 hours to 24 hours, preferably 1 hour to 12 hours.

Step 4

Compound Ia can be synthesized according to steps 7 and 8 of process 1 described above.

(Process 3)

[Chemical Formula 21]

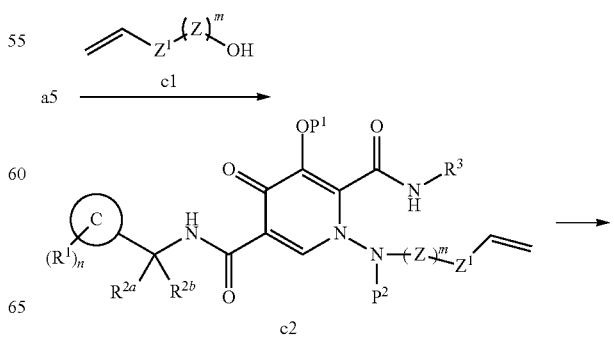

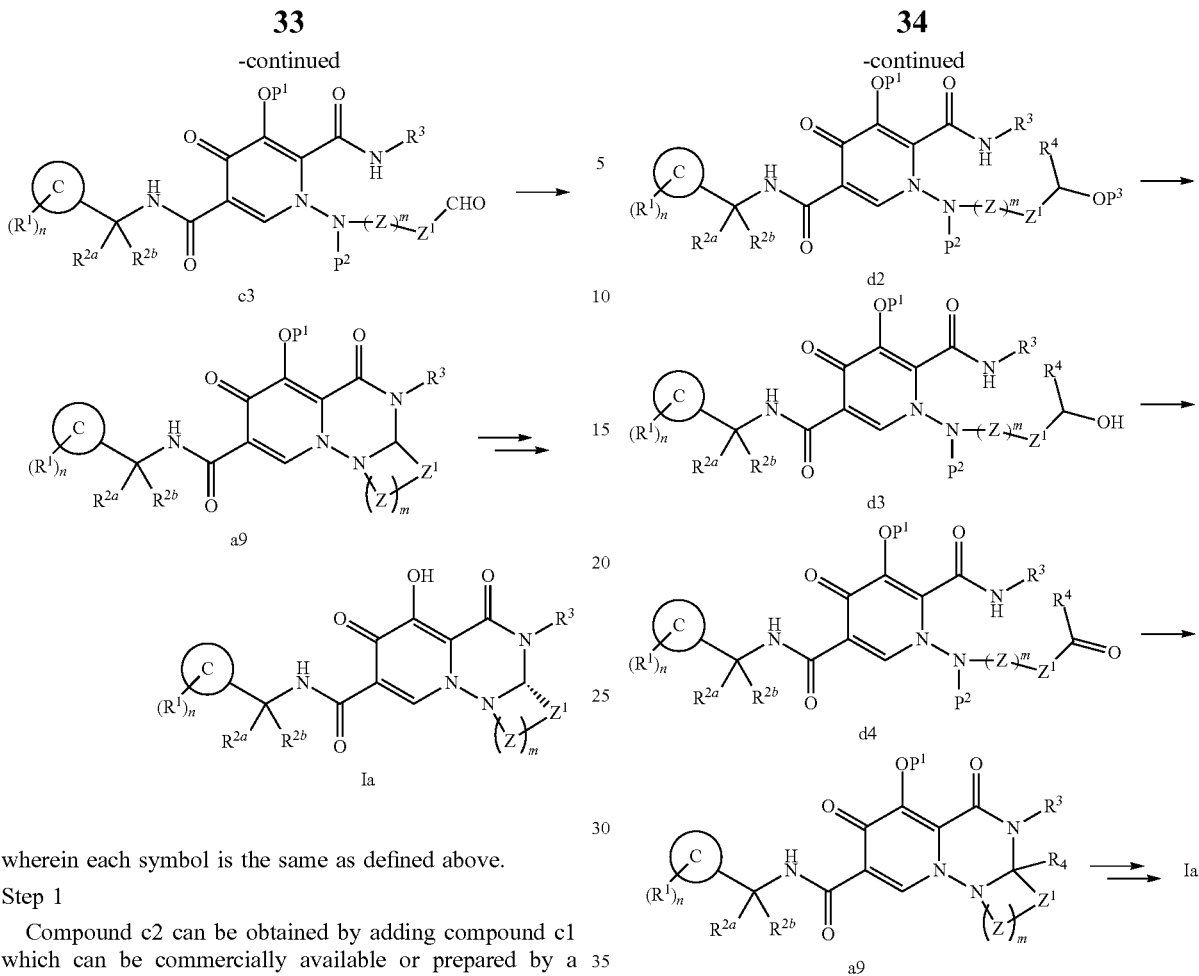

wherein each symbol is the same as defined above.

Step 1

Compound c2 can be obtained by adding compound c1 which can be commercially available or prepared by a known method, and a Mitsunobu reagent such as DEAD/PPh$_3$, DIAD/PPh$_3$, DMEAD/PPh$_3$, ADDP/n-Bu$_3$P to compound a5 in the presence of a solvent such as THF or toluene, and reacting the mixture at 0° C. to 100° C., preferably 20° C. to 80° C., for 0.1 hours to 24 hours, preferably 1 hour to 12 hours.

Step 2

Compound c3 can be obtained by subjecting compound c2 to the general oxidative cleavage reaction of alkene. Examples of the reaction include a reaction by ozonolysis or by using K$_2$OsO$_4$/NaIO$_4$ or the like.

Step 3

Compound a9 can be obtained by reacting compound c3 under the same conditions as in step 3 of process 2.

Step 4

Compound Ia can be synthesized according to steps 7 and 8 of process 1.

(Process 4)

[Chemical Formula 22]

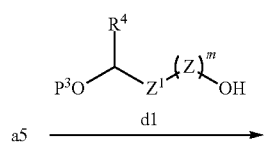

wherein each symbol is the same as defined above.

Step 1

Compound d2 can be obtained by reacting compound a5 and compound d1 under the same conditions as in step 1 of process 3.

Step 2

Compound d3 can be obtained by subjecting compound d2 to the general deprotection reaction of hydroxy-protective groups.

Step 3

Compound d4 can be obtained by subjecting compound d3 to the general oxidation reaction of hydroxyl groups.

Step 4

Compound a9 can be obtained by reacting compound d4 under the same conditions as in step 3 of process 2.

Step 5

Compound Ia can be synthesized according to steps 7 and 8 of process 1.

(Process 5)

[Chemical Formula 23]

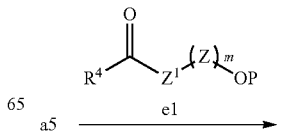

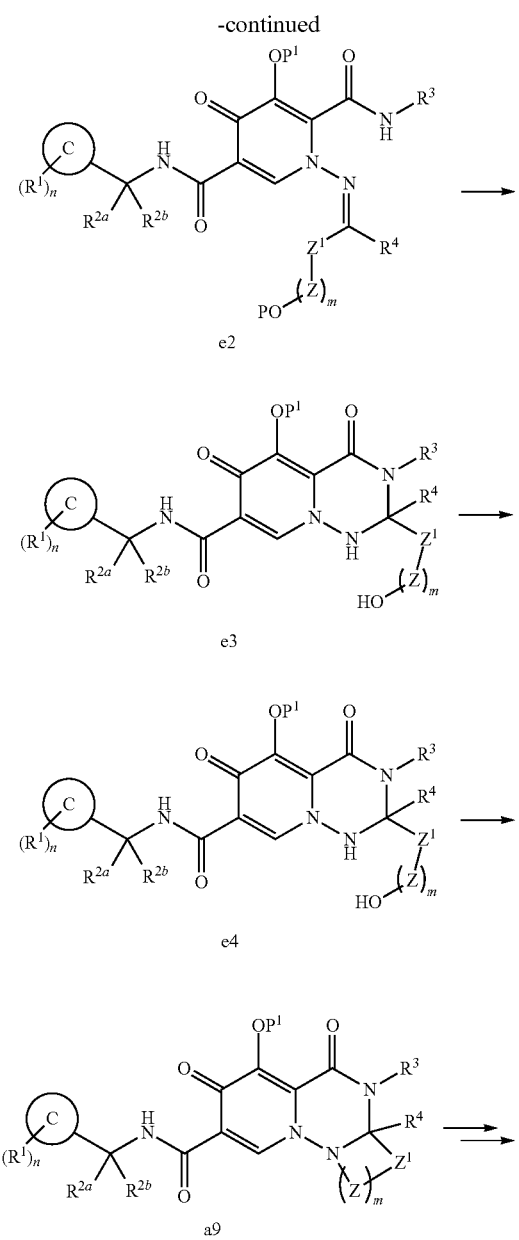

wherein each symbol is the same as defined above.

Step 1

Compound e2 can be obtained by reacting compound a5 and compound e1 under the same conditions as in step 5 of process 1.

Step 2

Compound e3 can be obtained by adding a base such as cesium carbonate or potassium carbonate to compound e2 in the presence of a solvent such as DMF, DMA, NMP, or THF, and reacting the mixture at 0° C. to 60° C., preferably 0° C. to 40° C., for 0.1 hours to 24 hours, preferably 1 hour to 12 hours.

Step 3

Compound e4 can be obtained by subjecting compound e3 to the general deprotection reaction of hydroxy-protective groups.

Step 4

Compound a9 can be obtained by adding a Mitsunobu reagent such as DEAD/PPh$_3$, DIAD/PPh$_3$, DMEAD/PPh$_3$, or ADDP/n-Bu$_3$P to compound e4 in the presence of a solvent such as THF or toluene, and reacting the mixture at 0° C. to 100° C., preferably 20° C. to 80° C., for 0.1 hours to 24 hours, preferably 1 hour to 12 hours.

Step 5

Compound Ia can be synthesized according to steps 7 and 8 of process 1.

The compound of the present invention thus obtained may be further chemically modified to synthesize another compound. When a reactive functional group (e.g., OH, COOH, or NH$_2$) is present at a side chain moiety or the like during the reaction, this functional group may be protected before the reaction and deprotected after the reaction, if desired.

Examples of the protective groups (amino-protective group, hydroxy-protective group, etc.) can include protective groups described in, for example, Protective Groups in Organic Synthesis, T. W. Green, John Wiley & Sons Inc. (1991), such as ethoxycarbonyl, tert-butoxycarbonyl, acetyl, and benzyl. Methods for introducing and eliminating the protective groups can be performed by methods routinely used in organic synthetic chemistry [see, for example, Protective Groups in Organic Synthesis, T. W. Greene, John Wiley & Sons Inc. (1991)] or methods equivalent thereto. The conversion of a functional group contained in each substituent can also be performed by a known method [e.g., Comprehensive Organic Transformations, R. C. Larock (1989)] other than the production methods described above. Some compound of the present invention can be further converted to novel derivatives with the compounds as intermediates for synthesis. The intermediate and the compound of interest in each production method described above can be subjected to a purification method routinely used in organic synthetic chemistry, for example, neutralization, filtration, extraction, washing, drying, concentration, recrystallization, or various chromatography techniques, and thereby isolated or purified. Alternatively, the intermediate may be subjected to next reaction without particular purification.

The compound of the present invention is useful as a medicament, for example, an antiviral drug. The compound of the present invention has a marked inhibitory effect on virus integrase. Accordingly, the compound of the present invention can be expected to have a prophylactic or therapeutic effect on various diseases caused by viruses that grow by producing at least integrase at the time of infection in animal cells, and is useful as, for example, a retrovirus (e.g., HIV-1, HIV-2, HTLV-1, SIV, or FTV) integrase inhibitor and as an anti-HIV drug. A preferred compound also has the following characteristics as pharmacokinetics in the body: the blood concentration is high; the duration of an effect is long; the transitivity to tissue is remarkable; and/or the like. In addition, a preferred compound is safe with regard to a side effect (e.g., inhibition of CYP enzymes, mutagenicity, the QT interval prolongation of the electrocardiogram, and arrhythmia).

The compound of the present invention can also be used in combination therapy with an anti-HIV drug having the different action mechanism, such as a reverse transcriptase inhibitor, a protease inhibitor, and/or an entry inhibitor.

The use described above includes not only use as an anti-HIV combination but use as a concomitant agent that elevates the anti-HIV activity of another anti-HIV drug, as in cocktail therapy or the like.

The compound of the present invention can be used for preventing infection with a retrovirus vector from spreading to tissues other than a tissue of interest when a retrovirus vector based on HTV or MIN is used in the field of gene therapy. Particularly, when cells or the like are infected with the vector in vitro and brought back to the body, the administration of the compound of the present invention beforehand can prevent the unnecessary infection of the body.

A pharmaceutical composition of the present invention can be administered orally or parenterally. Examples of the parenteral administration method include percutaneous administration, subcutaneous administration, intravenous administration, intraarterial administration, intramuscular administration, intraperitoneal administration, transmucosal administration, inhalation, transnasal administration, eye drop, ear drop, and intravaginal administration.

For oral administration, any dosage form usually used such as a solid preparation for internal use (e.g., a tablet, a powder, a granule, a capsule, a pill, and a film) or a liquid preparation for internal use (e.g., a suspension, an emulsion, an elixir, a syrup, a lemonade, a spirit, an aromatic water, an extract, a decoction, and a tincture) can be prepared according to a routine method, and administered. The tablet may be a sugar-coated tablet, a film-coated tablet, an enteric coated tablet, a sustained-release tablet, a troche tablet, a sublingual tablet, a buccal tablet, a chewable tablet or an orally disintegrating tablet. The powder and the granule may be a dry syrup. The capsule may be a soft capsule, a microcapsule or a sustained-release capsule.

For parenteral administration, any dosage form usually used such as an injection, a drop, and an external preparation (e.g., an eye drop, a nasal drop, an ear drop, an aerosol, an inhalant, a lotion, an infusion, a liniment, a gargle, an enema, an ointment, a plaster, a jelly, a cream, a patch, a poultice, a powder for external use, and a suppository) can be suitably administered. The injection may be an emulsion of O/W, W/O, O/W/O, W/O/W type, or the like.

The pharmaceutical composition may be manufactured by mixing an effective amount of the compound of the present invention with various pharmaceutical additives suitable for the formulation, such as excipients, binders, disintegrants, lubricants, and the like. Furthermore, the pharmaceutical composition can be for pediatric patients, geriatric patients, serious cases or operations by appropriately changing the effective amount of the compound of the present invention, formulation and/or various pharmaceutical additives. For example, the pediatric pharmaceutical compositions can be administered to neonate (under 4 weeks after the birth), infant (4 weeks after birth to under 1 year old), toddler (1 or more and under 7 years old), child (7 or more and under 15 years old) or patients of 15 to 18 years old. The geriatric pharmaceutical compositions, for example, are administered to patients of 65 or more years old.

The dose of the pharmaceutical composition of the present invention is desirably set in consideration of the age or body weight of a patient, the type or severity of a disease, an administration route, etc. For oral administration, the dose is within the range of usually 0.05 to 100 mg/kg/day, preferably 0.1 to 10 mg/kg/day. For parenteral administration, the dose differs largely depending on an administration route and is within the range of usually 0.005 to 10 mg/kg/day, preferably 0.01 to 1 mg/kg/day. This dose can be administered once a day to once a month or once three months.

EXAMPLES

Hereinafter, Examples are described.

Abbreviation

ADDP: 1,1'-(azodicarbonyl)dipiperidine
Bn: benzyl
DEAD: diethyl azodicarboxylate
DIAD: diisopropyl azodicarboxylate
DIEA: N,N-diisopropylethylamine
DMA: dimethylacetamide
DMEAD: di-2-methoxyethylazodicarboxylate
DMF: dimethylformamide
DMSO: dimethyl sulfoxide
HATU: O-(7-azabenzotriazol-1-yl)-N,N,N',N'-tetramethyluronium hexafluorophosphate
NMP: N-methylpyrrolidone
PyBOP: (benzotriazol-1-yloxy)tripyrrolidinophosphonium hexafluorophosphate
TBAF: tetrabutylammonium fluoride
THF: tetrahydrofuran
WSC·HCl: 1-ethyl-3-(3-dimethylaminopropyl)carbodiimide hydrochloride NMR analysis obtained in each Example was conducted at 300 MHz or 400 MHz, and the measurement was performed using DMSO-$d_6$ or CDCl$_3$. Sometimes not all the peaks detected are shown in NMR data.

In Examples, "No." represents compound number, "Structure" means a chemical structure, and "MS" represents a molecular weight in LC/MS (liquid chromatography/mass spectrometry).

(Measurement Conditions)
  (A) Column: ACQUITY UPLC(R) BEH C18 (1.7 μm i.d. 2.1×50 mm) (Waters Corporation)
    Flow rate: 0.8 mL/min; UV detection wavelength: 254 nm;
    Mobile phase: [A]: an aqueous solution containing 0.1% formic acid, [B]: an acetonitrile solution containing 0.1% formic acid
    Linear gradient of 5% to 100% solvent [B] was performed in 3.5 minutes, and then 100% solvent [B] was kept for 0.5 minutes.
  (B) Column: Shim-pack XR-ODS (2.2 μm, i.d. 50×3.0 mm) (Shimadzu Corporation)
    Flow rate: 1.6 mL/min; UV detection wavelength: 254 nm;
    Mobile phase: [A]: an aqueous solution containing 0.1% formic acid, [B]: an acetonitrile solution containing 0.1% formic acid
    Gradient: linear gradient of 10% to 100% solvent was performed in 3 minutes, and 100% solvent [B] was kept for 0.5 minutes.
  (C) Column: Shim-pack XR-ODS (2.2 μm, i.d. 50×3.0 mm) (Shimadzu Corporation)
    Flow rate: 1.6 mL/min; UV detection wavelength: 254 nm;
    Mobile phase: [A]: an aqueous solution containing 0.1% formic acid, [B]: an acetonitrile solution containing 0.1% formic acid
    Gradient: linear gradient of 10% to 100% solvent was performed in 8 minutes, and 100% solvent [B] was kept for 0.5 minutes.

Example 1

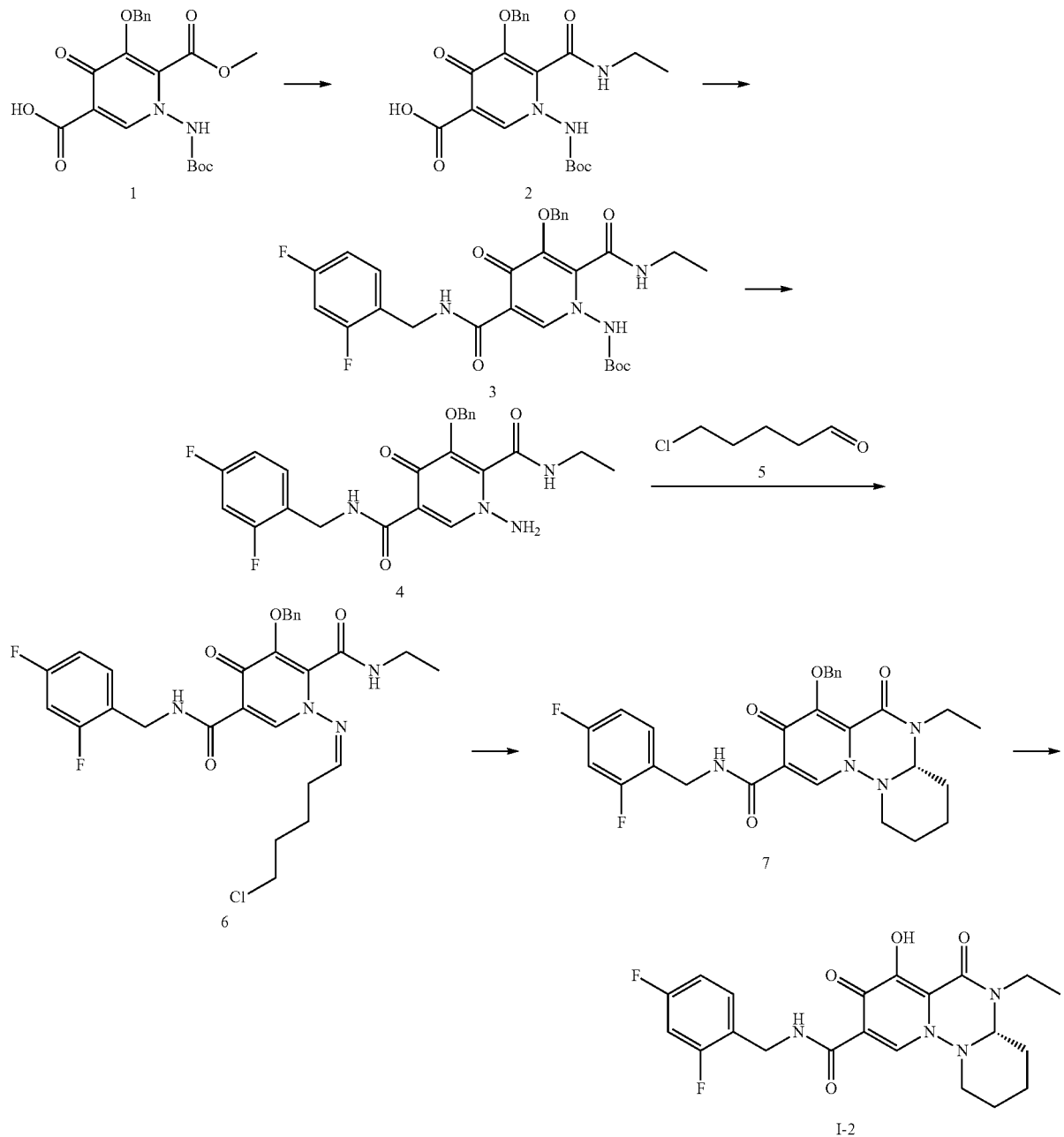

Step 1

To compound 1 (1.50 g, 3.59 mmol), a 2 mol/L solution of ethylamine in methanol (17.9 ml, 35.9 mmol) was added, and the mixture was stirred at 100° C. for 1 hour under microwave irradiation. The solvent in the reaction solution was distilled off under reduced pressure. The residue was then rendered acidic by the addition of dilute hydrochloric acid, followed by extraction with ethyl acetate. The organic layer was dried over sodium sulfate, and the solvent was then distilled off. The obtained residue was purified by silica gel column chromatography (chloroform-methanol) to give compound 2 (1.15 g, yield 74%).

1H-NMR (CDCl$_3$) δ: 14.53 (s, 1H), 8.64 (brs, 1H), 8.46 (s, 1H), 7.37 (m, 5H), 6.57 (brs, 1H), 5.38 (s, 2H), 3.24 (dt, J=14.0, 6.6 Hz, 2H), 1.45 (s, 9H), 1.02 (t, J=7.3 Hz, 4H).

Step 2

Compound 2 (9.59 g, 22.2 mmol) was dissolved in dichloromethane (180 ml). To the solution, (2,4-difluorophenyl)methanamine (4.77 g, 33.3 mmol), PyBOP (13.9 g, 26.7 mmol) and DIEA (11.7 ml, 66.7 mmol) were added, and the mixture was stirred at room temperature for 18 hours. The reaction solution was washed with water and brine. The organic layer was dried over sodium sulfate, and the solvent was then distilled off. The obtained residue was purified by silica gel column chromatography (chloroform-methanol) to give compound 3 (11.5 g, yield 93%). 1H-NMR (CDCl₃) δ: 10.20 (t, J=5.8 Hz, 1H), 8.54 (brs, 1H), 8.49 (s, 1H), 7.38 (m, 5H), 6.87-6.79 (m, 2H), 6.61 (t, J=5.5 Hz, 1H), 5.28 (s, 2H), 4.64 (d, J=5.9 Hz, 2H), 3.18 (ddt, J=18.8, 10.2, 3.8 Hz, 3H), 1.83-1.80 (m, 1H), 1.43 (s, 9H), 0.99 (t, J=7.3 Hz, 3H).

Step 3

Compound 3 (11.5 g, 9.54 mmol) was dissolved in dioxane (57.5 ml). To the solution, 4 mol/L solution of hydrochloric acid in dioxane (300 ml) was added, and the mixture was stirred at room temperature for 4 hours. The solvent in the reaction solution was distilled off under reduced pressure. Then, a saturated aqueous solution of sodium carbonate was added to the residue, and the mixture was extracted with chloroform-methanol. The organic layer was dried over sodium sulfate, and the solvent was then distilled off. The obtained crude product was solidified from diisopropyl ether to give compound 4 (7.80 g, yield 83%).

1H-NMR (CDCl₃) δ: 10.33 (s, 1H), 8.60 (s, 1H), 7.39 (m, 5H), 6.83 (m, 3H), 5.82 (s, 2H), 5.26 (s, 2H), 4.64 (d, J=5.8 Hz, 2H), 3.28-3.21 (m, 2H), 1.02 (t, J=7.3 Hz, 3H).

Step 4

Compound 4 (200 mg, 0.438 mmol) was dissolved in dichloromethane (4 ml). To the solution, compound 5 (111 mg, 0.920 mmol) and acetic acid (catalytic amount) were added, and the mixture was stirred at room temperature for 19 hours. The reaction solution was concentrated under reduced pressure, and the residue was purified by silica gel column chromatography (chloroform-methanol) to give compound 6 (265 mg, yield 100%).

MS: m/z=559 [M+H]+

Step 5

Compound 6 (245 mg, 0.438 mmol) was dissolved in DMF (5 ml). To the solution, cesium carbonate (428 mg, 1.31 mmol) was added at 0° C., and the mixture was stirred at room temperature for 18 hours. To the reaction solution, dilute hydrochloric acid was added, and the mixture was extracted with ethyl acetate. The organic layer was washed with water and dried over sodium sulfate, and the solvent was then distilled off. The obtained residue was purified by silica gel column chromatography (chloroform-methanol) to give a racemic mixture (139 mg, yield 60%).

The obtained racemic mixture was optically resolved by SFC to give compound 7.

Column: CHIRALPAK IA/SFC (5 μm, i.d. 250×20 mm)
Flow rate: 30 mL/min
UV detection wavelength: 250 nm
Fractionation conditions: a compositional ratio of MeOH/CO₂=45/55 was kept, and the solution was sent for 21 minutes.

1H-NMR (CDCl₃) δ: 10.46 (s, 1H), 8.51 (s, 1H), 7.58 (m, 2H), 7.34 (m, 4H), 6.81 (m, 2H), 5.41 (d, J=10.4 Hz, 1H), 5.26 (d, J=10.4 Hz, 1H), 4.91 (s, 1H), 4.64 (m, 2H), 4.39 (dd, J=14.3, 7.2 Hz, 1H), 3.18-2.88 (m, 3H), 2.24 (d, J=14.7 Hz, 1H), 2.00 (m, 1H), 1.85 (m, 2H), 1.72 (d, J=13.6 Hz, 1H), 1.38 (m, 1H), 1.16 (t, J=7.1 Hz, 3H).

Step 6

Compound 7 (44.0 mg, 0.0840 mmol) was dissolved in DMF (0.88 ml). To the solution, lithium chloride (35.7 mg, 0.842 mmol) was added, and the mixture was stirred at 90° C. for 1.5 hours. To the reaction solution, water was added, and the mixture was rendered acidic with a 10% aqueous citric acid solution, followed by extraction with ethyl acetate. The organic layer was washed with water and dried over sodium sulfate, and the solvent was then distilled off. The obtained crude product was solidified from diethyl ether to give compound 1-2 (19 mg, yield 52%).

1H-NMR (CDCl₃) δ: 11.98 (s, 1H), 10.42 (s, 1H), 8.46 (s, 1H), 7.36 (dd, d=15.2, 8.6 Hz, 1H), 6.83-6.77 (m, 2H), 5.06 (s, 1H), 4.64 (m, 2H), 4.35 (td, J=14.2, 6.9 Hz, 1H), 3.20-3.09 (m, 2H), 3.00 (d, J=10.8 Hz, 1H), 2.31 (d, J=15.4 Hz, 1H), 2.06 (m, 1H), 1.89 (m, 2H), 1.76 (m, 1H), 1.42-1.36 (m, 1H), 1.24 (t, J=7.1 Hz, 4H).

Example 2

[Chemical Formula 25]

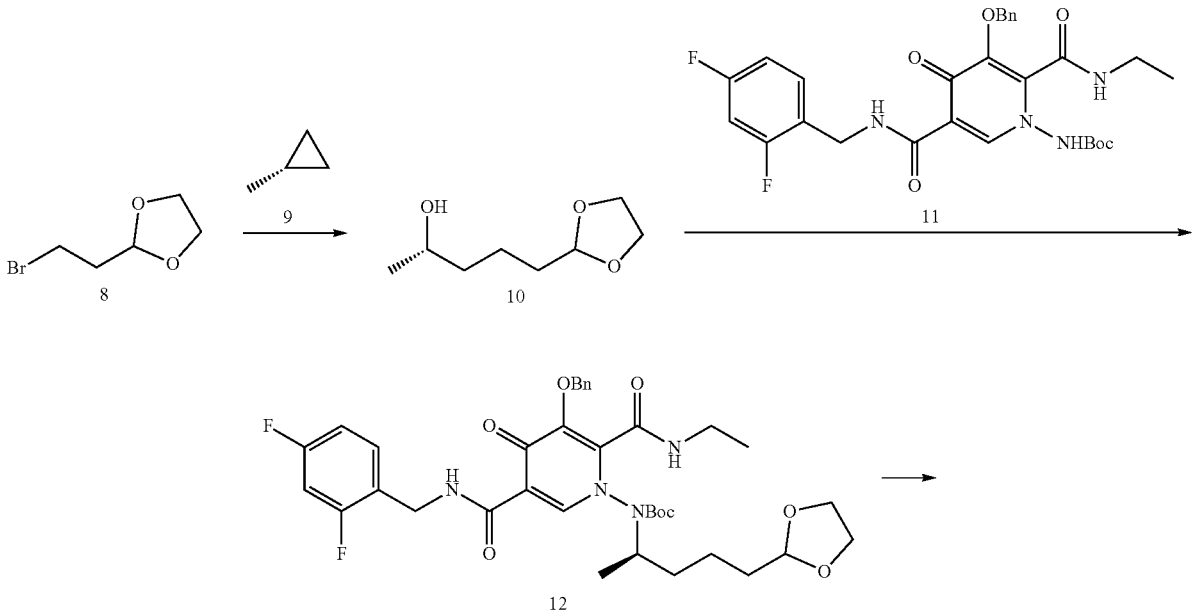

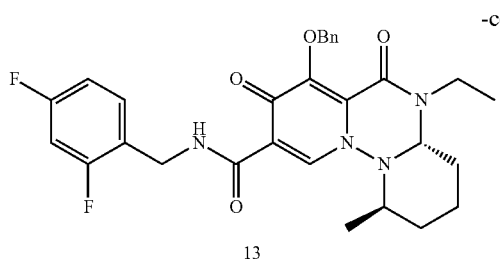
13

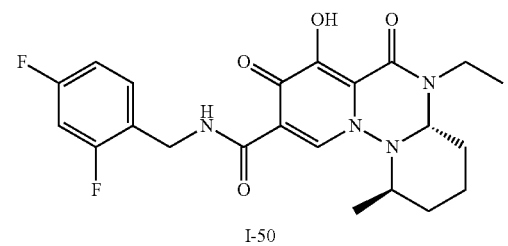
I-50

Step 1

Under nitrogen atmosphere, a solution of compound 8 (1.3 mL, 11.1 mmol) in THF (7.0 mL) was added dropwise to a solution of magnesium (322 mg, 13.3 mmol) in THF (3.0 mL), and the mixture was stirred at room temperature for 30 minutes. The reaction solution was cooled to 0° C., and copper iodide (210 mg, 1.1 mmol) was added, and a solution of compound 9 (1.2 mL, 16.6 mmol) in THF (6.0 mL) was added dropwise. The mixture was warmed to room temperature and stirred for 2 hours. To the reaction solution, a saturated aqueous solution of ammonium chloride was added. The mixture was extracted with ethyl acetate. The organic layer was washed with brine and dried over anhydrous sodium sulfate, and the solvent was then distilled off. The obtained residue was purified by silica gel column chromatography (hexane-ethyl acetate) to give compound 10 (192 mg, yield 11%).

1H-NMR (CDCl$_3$) δ: 4.86 (t, J=4.8 Hz, 1H), 3.99-3.96 (m, 2H), 3.90-3.79 (m, 3H), 1.72-1.67 (m, 2H), 1.55-1.48 (m, 4H), 1.36 (d, J=4.5 Hz, 1H), 1.20 (d, J=6.3 Hz, 3H).

Step 2

To a solution of compound 11 (334 mg, 0.60 mmol) in THF (2.0 mL), compound 10 (192.2 mg, 1.2 mmol), triphenylphosphine (315 mg, 1.2 mmol) and bis(2-methoxyethyl) azodicarboxylate (281 mg, 1.0 mmol) were added, and the mixture was stirred at room temperature for 1 hour. To the reaction solution, water was added, and the mixture was extracted with ethyl acetate. The organic layer was washed with brine and dried over anhydrous sodium sulfate, and the solvent was then distilled off. The obtained residue was roughly purified by silica gel column chromatography (hexane-ethyl acetate).

MS: m/z=699 [M+H]+

Step 3

To a solution of the crude purified product (100 mg) obtained in Step 2 in acetonitrile (1.0 mL), p-toluenesulfonic acid hydrate (45.1 mg, 0.242 mmol) was added, and the mixture was heated to reflux for 210 minutes. The reaction solution was left to cool to room temperature, and a saturated aqueous solution of sodium hydrogen carbonate was added. The mixture was extracted with ethyl acetate. The organic layer was washed with brine and dried over anhydrous sodium sulfate, and the solvent was then distilled off. The obtained residue was dissolved in DMF (1.0 mL). To the solution, cesium carbonate (140 mg, 0.43 mmol) and benzyl bromide (34.1 μL, 0.29 mmol) were added, and the mixture was stirred at room temperature for 3 hours. To the reaction solution, water was added, and the mixture was extracted with ethyl acetate. The organic layer was washed with brine and dried over anhydrous sodium sulfate, and the solvent was then distilled off. The obtained residue was purified by silica gel column chromatography (chloroform-methanol) to give compound 13 (65.1 mg).

MS: m/z=537 [M+H]+

Step 4

Compound 13 was subjected to the same reaction as in step 6 of Example 1 to give compound 1-50 (31 mg, yield 57%).

1H-NMR (CDCl$_3$) δ: 11.93 (s, 1H), 10.40 (s, 1H), 8.39 (s, 1H), 7.40-7.34 (m, 1H), 6.84-6.77 (m, 2H), 5.11-5.09 (m, 1H), 4.64 (d, J=5.8 Hz, 2H), 4.40-4.31 (m, 1H), 3.27-3.21 (m, 1H), 3.13-3.06 (m, 1H), 2.32-2.28 (m, 1H), 2.12-2.04 (m, 1H), 1.86-1.83 (m, 1H), 1.79-1.75 (m, 1H), 1.63-1.48 (m, 2H), 1.21 (t, J=7.2 Hz, 3H), 0.89 (d, J=6.3 Hz, 3H).

Example 3

[Chemical Formula 26]

11 ⟶

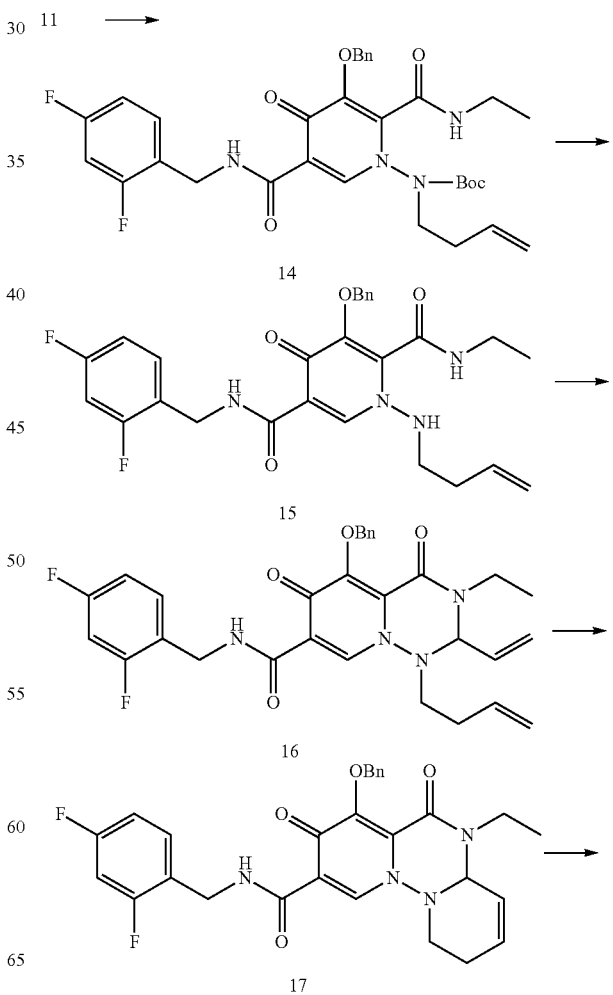

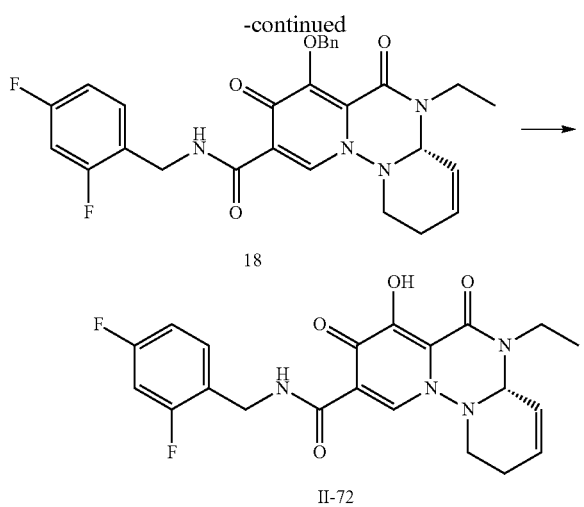

Step 1

To a solution of compound 11 (352 mg, 0.629 mmol) in DMF (3.5 ml), potassium carbonate (261 mg, 1.89 mmol) and 4-bromobutene (147 mg, 0.943 mmol) were added, and the mixture was reacted overnight at room temperature. To the reaction solution, water was added, and the mixture was extracted with ethyl acetate. The organic layer was washed with water and brine and dried over anhydrous sodium sulfate, and the solvent was then distilled off.

MS: m/z=611 [M+H]+

Step 2

To the obtained crude product in step 1, 4 mol/T, solution of hydrochloric acid in dioxane (3.15 ml) was added, and the mixture was stirred at room temperature for 2 hours. To the reaction solution, a saturated aqueous solution of sodium bicarbonate was added, and the mixture was extracted with ethyl acetate. The organic layer was washed with brine and dried over anhydrous sodium sulfate, and the solvent was then distilled off.

MS: m/z=511 [M+H]+

Step 3

The obtained crude product in step 2, acrolein (102 mg, 1.83 mmol) and p-toluenesulfonic acid hydrate (11.6 mg, 0.061 mmol) were dissolved in dichloroethane (9.6 mL). The solution was stirred at 100° C. for 6 hours. After the reaction solution was left to cool to room temperature, water and a saturated aqueous solution of sodium bicarbonate were added, and the mixture was extracted with ethyl acetate. The organic layer was washed with brine and dried over anhydrous sodium sulfate, and the solvent was then distilled off. The obtained residue was purified by silica gel column chromatography (hexane-ethyl acetate) to give compound 16 (115 mg).

MS: m/z=549 [M+H]+

Step 4

Compound 16 (66.4 mg, 0.121 mmol) and a Hoveyda-Grubbs second-generation catalyst (60 mg, 0.139 mmol) were dissolved in dichloromethane (10 mL). The solution was heated to reflux for 6 hours. The solvent of the reaction solution was then distilled off, and the obtained residue was roughly purified by silica gel column chromatography (ethyl acetate-methanol).

MS: m/z=521 [M+H]+

Step 5

The obtained compound 17 in step 4 was optically resolved by SFC to give compound 18.

Column: CHIRALPAK IC/SFC (5 μm, i.d. 250×20 mm)
Flow rate: 20 mL/min
UV detection wavelength: 220 nm
Analytical conditions: a compositional ratio of MeOH/$CO_2$=70/30 was kept, and the solution was sent for 21 minutes.

Step 6

Compound 18 was subjected to the same reaction as in step 6 of Example 1 to give compound 11-72 (11 mg, yield 74%).

1H-NMR (CDCl$_3$) δ: 11.93 (s, 1H), 10.42 (t, J=5.6 Hz, 1H), 8.50 (s, 1H), 7.40-7.33 (m, 1H), 6.84-6.77 (m, 2H), 6.28-6.24 (m, 1H), 5.96-5.91 (m, 1H), 5.32 (d, J=5.2 Hz, 1H), 4.68 (dd, J=15.2, 6.0 Hz, 1H), 4.61 (dd, J=15.6, 6.0 Hz, 1H), 3.83 (dt, J=21.2, 7.2 Hz, 1H), 3.53 (dt, J=20.8, 6.8 Hz, 1H), 3.39 (td, J=11.2, 4.4 Hz, 1H), 3.04 (dd, J=10.8, 6.8 Hz, 1H), 2.77-2.68 (m, 1H), 2.35 (dt, J=18.8, 4.8 Hz, 1H), 1.23 (t, J=7.2 Hz, 3H).

Example 4

[Chemical Formula 27]

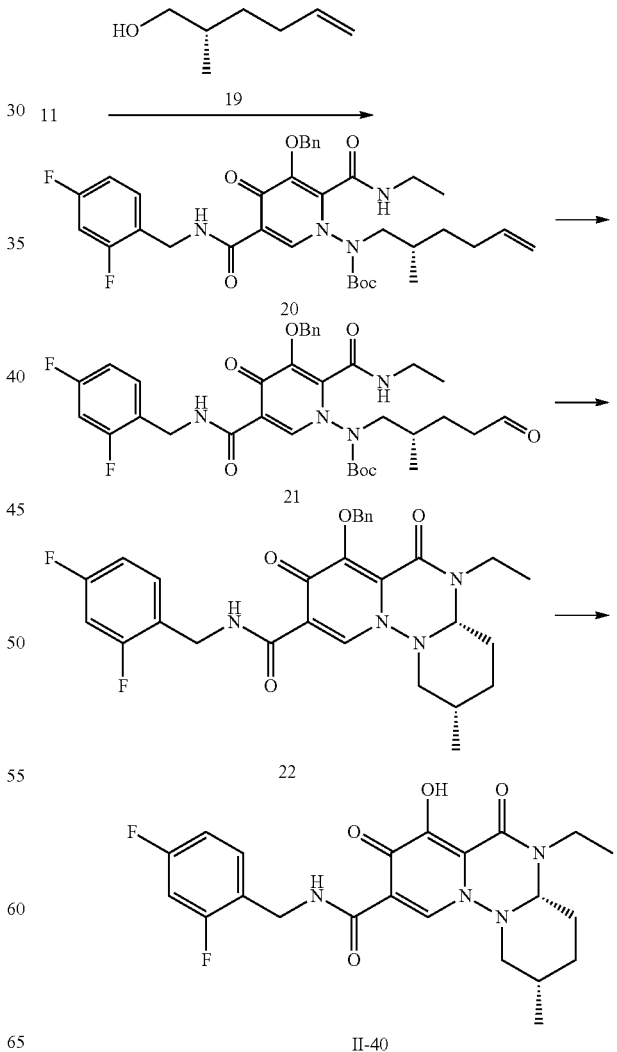

47

Step 1

To a solution of compound 11 (326 mg, 0.59 mmol), compound 19 (87 mg, 0.77 mmol), and triphenylphosphine (307 mg, 1.18 mmol) in THF (3.5 mL), di-2-methoxyethyl azodicarboxylate (274 mg, 1.18 mmol) was added at 0° C., and the mixture was left still at room temperature for 12 hours. To the reaction solution, water was added, and the mixture was extracted with ethyl acetate. The organic layer was washed with water and brine and dried over anhydrous sodium sulfate, and the solvent was then distilled off. The obtained residue was purified by silica gel column chromatography (hexane-ethyl acetate) to give compound 20 (293 mg, yield 77%).

MS: m/z=653 [M+H]+

Step 2

Compound 20 (287 mg, 0.44 mmol) was suspended in dioxane (3.4 mL) and water (2.3 mL). To the suspension, 2,6-lutidine (0.10 mL), sodium hydrogen periodate (282 mg, 1.32 mmol), and potassium osmium (VI) acid dihydrate (8.0 mg, 0.02 mmol) were added at 0° C., and the mixture was warmed from 0° C. to room temperature for 5 hours. The reaction solution was filtered with Celite® and 10% aqueous solution of sodium thiosulfate was added. The mixture was extracted with ethyl acetate. The organic layer was washed with water and brine and dried over anhydrous sodium sulfate, and the solvent was then distilled off. The obtained residue was purified by silica gel column chromatography (hexane-ethyl acetate) to give compound 21 (223 mg, yield 78%).

MS: m/z=655 [M+H]+

Step 3

The compound 21 (192 mg, 0.29 mmol) was dissolved in 4 mol/L solution of hydrochloric acid in dioxane (1.47 ml). The mixture was stirred at room temperature for 2 hours. The solvent was distilled, and the obtained crude product was dissolved in toluene (2.0 ml). To the solution, a catalytic amount of acetic acid was added, and the mixture was stirred at 90° C. for 2 hours. To the reaction solution, a saturated aqueous solution of sodium bicarbonate was added, and the mixture was extracted with ethyl acetate. The organic layer was washed with water and brine and dried over sodium sulfate, and the solvent was then distilled off. The obtained residue was purified by silica gel column chromatography to give a diastereomeric mixture. The obtained diastereomeric mixture was optically resolved by SFC to give compound 22 (69 mg, yield 44%).

Column: Two columns, CHIRALPAK IC/SFC (5 μm, i.d. 250×20 mm), were used in series.

Flow rate: 20 mL/min

UV detection wavelength: 220 nm

Fractionation conditions: a compositional ratio of MeOH/$CO_2$=65/35 was kept, and the solution was sent for 35 minutes.

MS: m/z=537 [M+H]+

Step 4

Compound 22 was subjected to the same reaction as in step 6 of Example 1 to give compound II-40.

MS: m/z=447 [M+H]+

48

Example 5

[Chemical Formula 28]

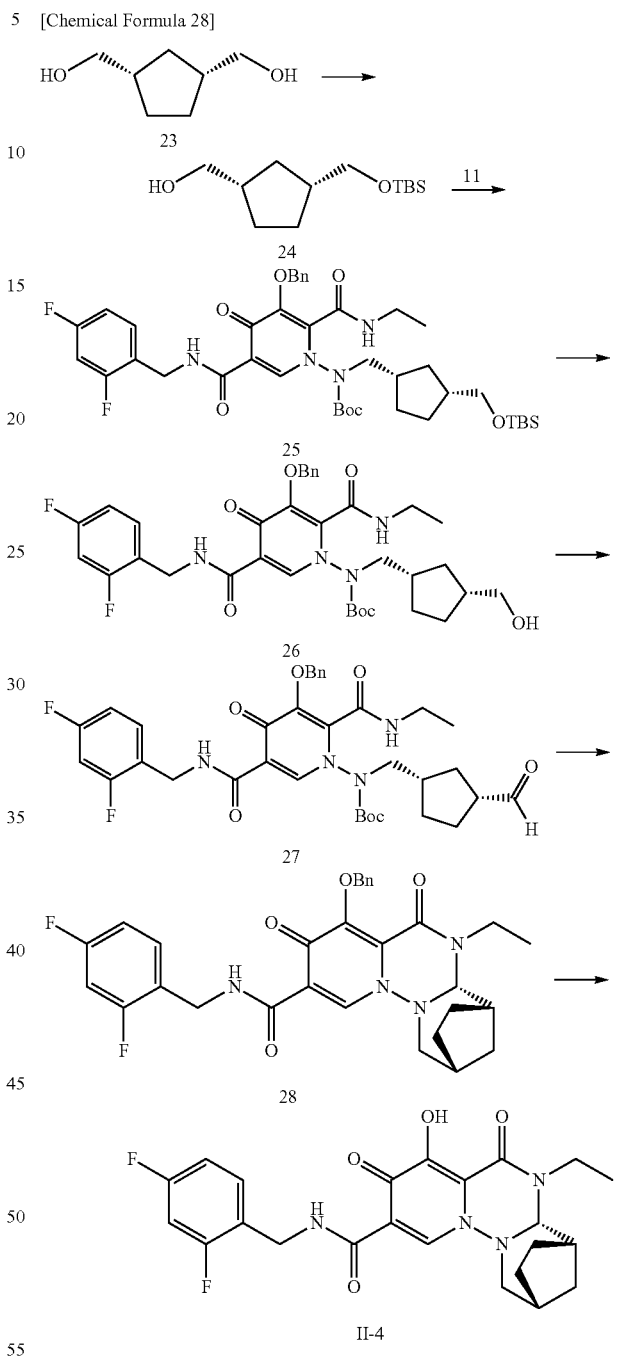

Step 1

To a solution of compound 23 (1.59 g, 12.2 mmol) in DMF (16.0 mL), imidazole (0.998 g, 14.66 mmol) and t-butyldimethylsilyl chloride (1.84 g, 12.21 mmol) were added at 0° C., and the mixture was stirred at room temperature for 3 hours. To the reaction solution, a saturated aqueous solution of ammonium chloride was added, and the mixture was extracted with ethyl acetate. The organic layer was washed with water and brine and dried over anhydrous sodium sulfate, and the solvent was then distilled off. The obtained residue was purified by silica gel column chromatography (hexane-ethyl acetate) to give compound 24 (1.39 g, 47%).

1H-NMR (CDCl$_3$) δ: 3.47-3.55 (m, 4H), 2.09-2.15 (m, 2H), 1.88-1.95 (s, 1H), 1.65-1.79 (m, 2H), 1.32-1.42 (m, 2H), 0.88-0.89 (m, 1H), 0.85 (s, 9H), 0.039 (s, 6H).

Step 2

To a solution of compound 24 (400 mg, 0.164 mmol), compound 11 (700 mg, 1.26 mmol), and triphenylphosphine (660 mg, 2.52 mmol) in THF (7 mL), di-2-methoxyethyl azodicarboxylate (589 mg, 2.52 mmol) was added at 0° C., and the mixture was left still at room temperature for 12 hours. To the reaction solution, water was added, and the mixture was extracted with ethyl acetate. The organic layer was washed with water and dried over anhydrous sodium sulfate, and the solvent was then distilled off. The obtained residue was roughly purified by silica gel column chromatography (hexane-ethyl acetate).

Step 3

To a solution of compound 25 (1.06 g, 1.35 mmol) in THF (10.0 mL), 1 mol/L solution of TBAF in THF (1.63 mL, 1.63 mmol) was added, and the mixture was stirred at room temperature for 12 hours. To the reaction solution, a saturated aqueous solution of ammonium chloride was added, and the mixture was extracted with ethyl acetate. The organic layer was washed with water and brine and dried over anhydrous sodium sulfate, and the solvent was then distilled off. The obtained residue was purified by silica gel column chromatography (hexane-ethyl acetate) to give compound 26 (720 mg, yield 80%).

MS: m/z=669 [M+H]+

Step 4

To the solution of compound 26 (720 mg, 1.08 mmol) in dichloromethane (8.0 mL), Dess-Martin periodinane was added at 0° C. The mixture was stirred at room temperature for 1 hour. To the reaction solution, a 10% aqueous solution of sodium thiosulfate and a saturated aqueous solution of sodium hydrogen carbonate were added, and the mixture was extracted with chloroform. The organic layer was washed with water and brine and dried over anhydrous sodium sulfate, and the solvent was then distilled off. The obtained residue was purified by silica gel column chromatography (hexane-ethyl acetate) to give compound 27 (393 mg, yield 55%).

MS: m/z=667 [M+H]+

Step 5

A solution of compound 27 (393 mg, 0.59 mmol) in acetonitrile (8.0 mL) was warmed to 60° C. and stirred for 80 minutes. To the reaction solution, a saturated aqueous solution of sodium hydrogen carbonate was added, and the mixture was extracted with ethyl acetate. The organic layer was washed with water and brine and dried over anhydrous sodium sulfate, and the solvent was then distilled off. The obtained crude product was dissolved in DMF (4.0 mL). To the solution, cesium carbonate (576 mg, 1.77 mmol) and benzyl bromide (0.21 mL, 1.77 mmol) were added at 0° C., and the mixture was stirred at room temperature overnight. To the reaction solution, water was added, and the mixture was extracted with ethyl acetate. The organic layer was washed with water and brine and dried over anhydrous sodium sulfate, and the solvent was then distilled off. The obtained residue was purified by silica gel column chromatography (hexane-ethyl acetate) and optically resolved by SFC to give compound 28 (89 mg, yield 28%).

Column: Two columns, CHIRALPAK IC/SFC (5 μm, i.d. 250×20 mm), were used in series.

Flow rate: 20 mL/min

UV detection wavelength: 220 nm

Fractionation conditions: a compositional ratio of MeOH/CO$_2$=75/25 was kept, and the solution was sent for 45 minutes.

MS: m/z=549 [M+H]+

Step 6

Compound 28 was subjected to the same reaction as in step 6 of Example 1 to give compound II-4 (11 mg, yield 74%).

MS: m/z=459 [M+H]+

The following compounds were also synthesized in the same way as above.

TABLE 1

| NO. | Structure |
|---|---|
| I-001 | 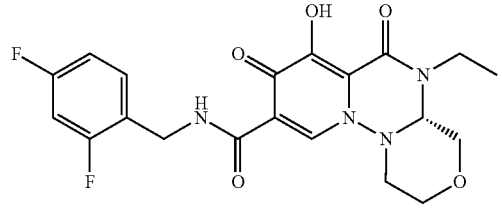 [SMILES: CCN1C(=O)c2c(O)c(=O)c(C(=O)NCc3ccc(F)cc3F)cn2N2CCOC[C@@H]12] |
| I-003 | 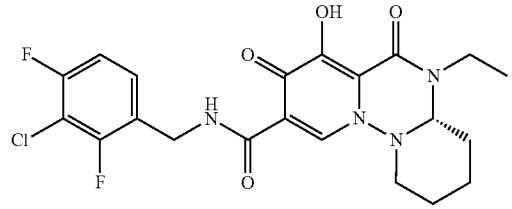 [SMILES: CCN1C(=O)c2c(O)c(=O)c(C(=O)NCc3ccc(F)c(Cl)c3F)cn2N2CCCC[C@@H]12] |

TABLE 1-continued

| NO. | Structure |
|---|---|
| I-004 | 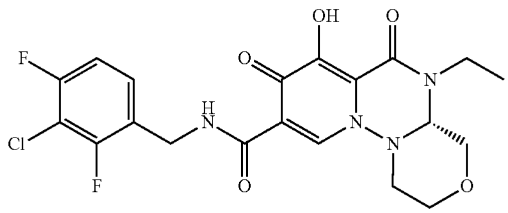 [SMILES: CCN1C(=O)c2c(O)c(=O)c(C(=O)NCc3ccc(F)c(Cl)c3F)cn2N2CCOC[C@@H]12] |
| I-005 | 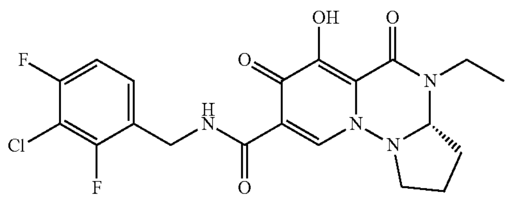 [SMILES: CCN1C(=O)c2c(O)c(=O)c(C(=O)NCc3ccc(F)c(Cl)c3F)cn2N2CCC[C@@H]12] |
| I-006 | 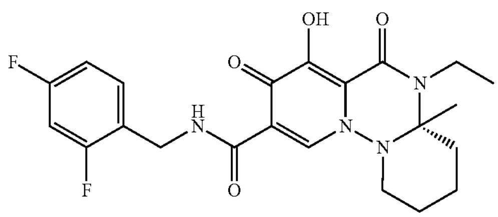 [SMILES: CCN1C(=O)c2c(O)c(=O)c(C(=O)NCc3ccc(F)cc3F)cn2N2CCCC[C@@]12C] |
| I-007 | 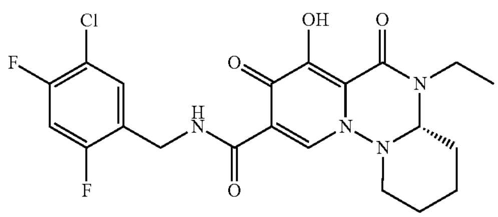 |
| I-008 | 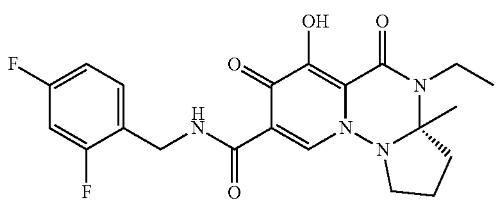 [SMILES: CCN1C(=O)c2c(O)c(=O)c(C(=O)NCc3ccc(F)cc3F)cn2N2CCC[C@@]12C] |
| I-009 | 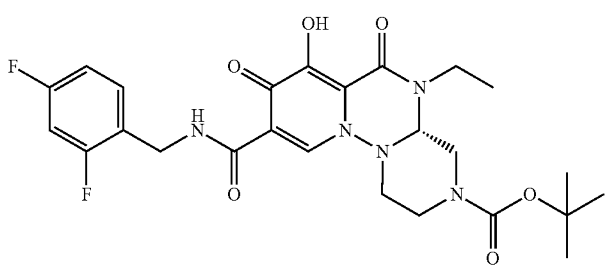 [SMILES: CCN1C(=O)c2c(O)c(=O)c(C(=O)NCc3ccc(F)cc3F)cn2N2CCN(C(=O)OC(C)(C)C)C[C@@H]12] |
| I-010 | 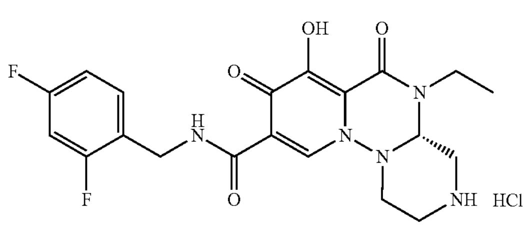 [SMILES: CCN1C(=O)c2c(O)c(=O)c(C(=O)NCc3ccc(F)cc3F)cn2N2CCNC[C@@H]12 ; Cl] |

TABLE 1-continued
| NO. | Structure |
|---|---|
| I-011 | 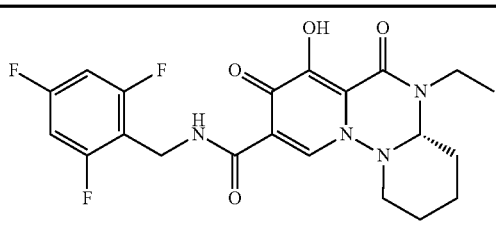 |
| I-012 | 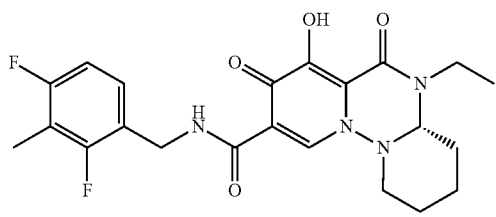 [SMILES: CCN1C(=O)c2c(O)c(=O)c(C(=O)NCc3ccc(F)c(C)c3F)cn2N2CCCC[C@@H]12] |
| I-013 | 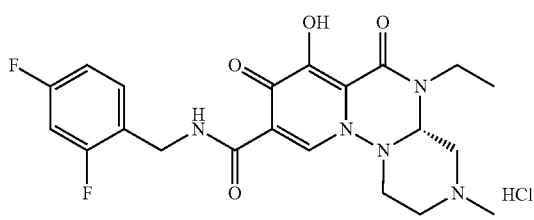 [SMILES: CCN1C(=O)c2c(O)c(=O)c(C(=O)NCc3ccc(F)cc3F)cn2N2CCN(C)C[C@@H]12 ; Cl] |
| I-014 | 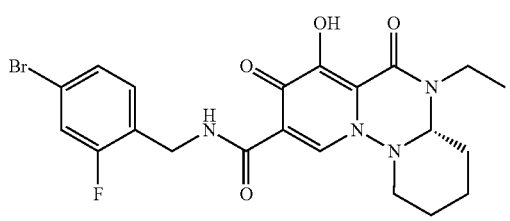 |
| I-015 | 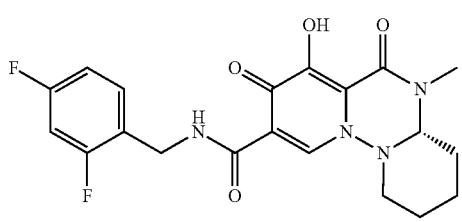 [SMILES: CN1C(=O)c2c(O)c(=O)c(C(=O)NCc3ccc(F)cc3F)cn2N2CCCC[C@@H]12] |
| I-016 | 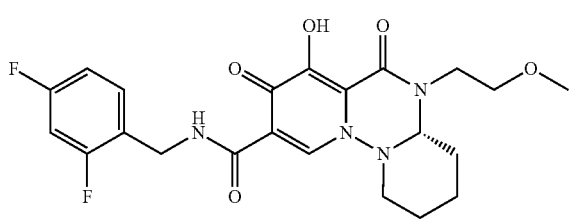 [SMILES: COCCN1C(=O)c2c(O)c(=O)c(C(=O)NCc3ccc(F)cc3F)cn2N2CCCC[C@@H]12] |
| I-017 | 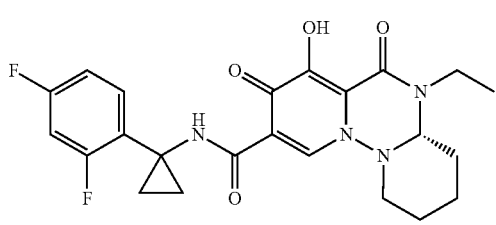 [SMILES: CCN1C(=O)c2c(O)c(=O)c(C(=O)NC3(c4ccc(F)cc4F)CC3)cn2N2CCCC[C@@H]12] |

TABLE 1-continued

| NO. | Structure |
|---|---|
| I-018 | (structure) |
| I-019 | (structure) |

TABLE 2

| NO. | Structure |
|---|---|
| I-020 | (structure) |
| I-021 | (structure) |
| I-022 | (structure) |
| I-023 | (structure) |

TABLE 2-continued
| NO. | Structure |
|---|---|
| I-024 | 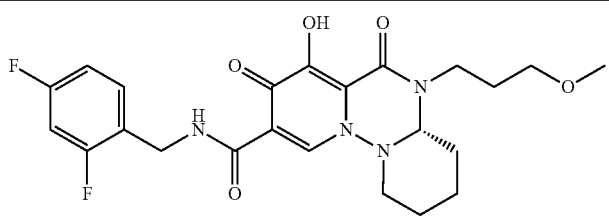 |
| I-025 | 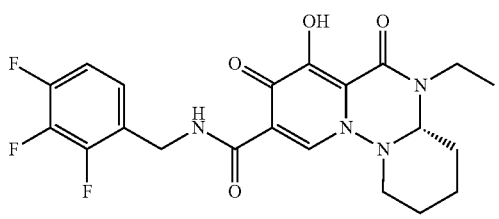 [SMILES: CCN1C(=O)c2c(O)c(=O)c(C(=O)NCc3ccc(F)c(F)c3F)cn2N2CCCC[C@@H]12] |
| I-026 | 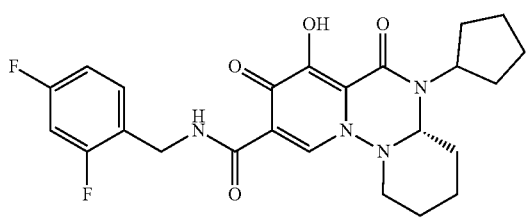 [SMILES: O=C(NCc1ccc(F)cc1F)c1cn2c(c(O)c1=O)C(=O)N(C1CCCC1)[C@@H]1CCCCN12] |
| I-027 | 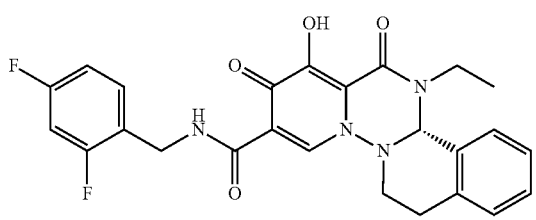 [SMILES: CCN1C(=O)c2c(O)c(=O)c(C(=O)NCc3ccc(F)cc3F)cn2N2CCc3ccccc3[C@@H]12] |
| I-028 | 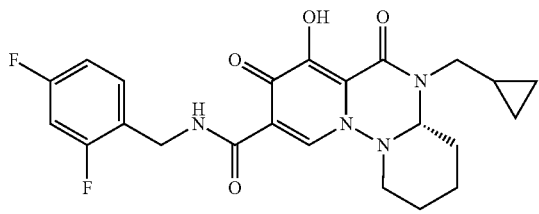 [SMILES: O=C(NCc1ccc(F)cc1F)c1cn2c(c(O)c1=O)C(=O)N(CC1CC1)[C@@H]1CCCCN12] |
| I-029 | 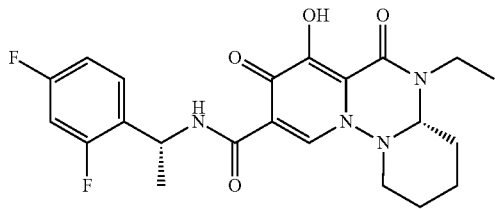 [SMILES: CCN1C(=O)c2c(O)c(=O)c(C(=O)N[C@H](C)c3ccc(F)cc3F)cn2N2CCCC[C@@H]12] |
| I-030 | 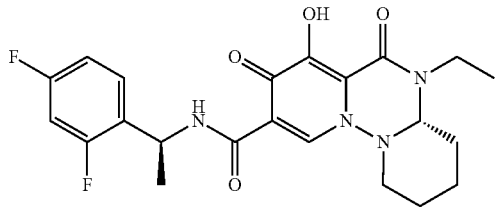 [SMILES: CCN1C(=O)c2c(O)c(=O)c(C(=O)N[C@@H](C)c3ccc(F)cc3F)cn2N2CCCC[C@@H]12] |

TABLE 2-continued
| NO. | Structure |
|---|---|
| I-031 | 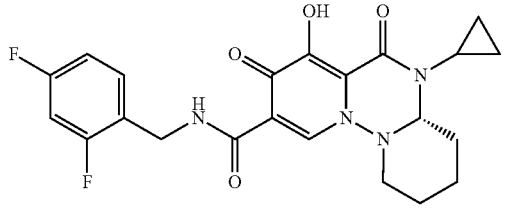 [SMILES: O=C(NCc1ccc(F)cc1F)c1cn2c(c(O)c1=O)C(=O)N(C1CC1)[C@@H]1CCCCN12] |
| I-032 | 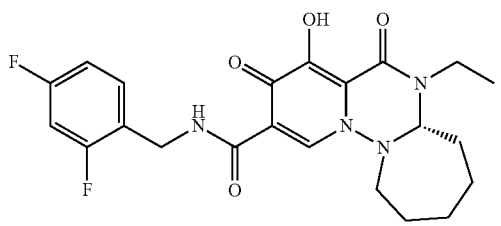 [SMILES: CCN1C(=O)c2c(O)c(=O)c(C(=O)NCc3ccc(F)cc3F)cn2N2CCCCC[C@@H]12] |
| I-033 | 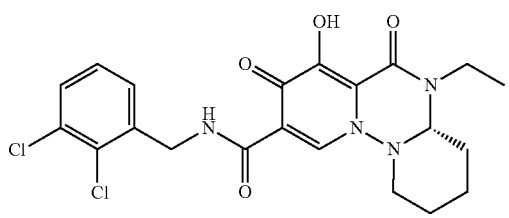 |
| I-034 | 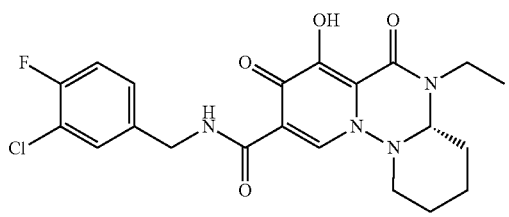 [SMILES: CCN1C(=O)c2c(O)c(=O)c(C(=O)NCc3ccc(F)c(Cl)c3)cn2N2CCCC[C@@H]12] |
| I-035 | 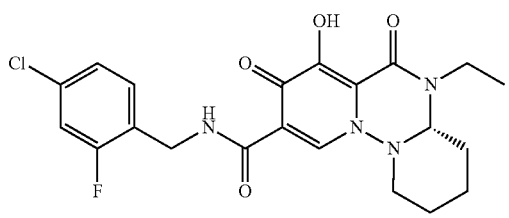 [SMILES: CCN1C(=O)c2c(O)c(=O)c(C(=O)NCc3ccc(Cl)cc3F)cn2N2CCCC[C@@H]12] |
| I-036 | 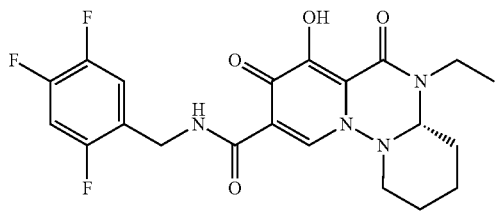 |
| I-037 | 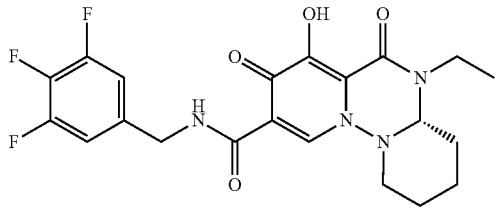 [SMILES: CCN1C(=O)c2c(O)c(=O)c(C(=O)NCc3cc(F)c(F)c(F)c3)cn2N2CCCC[C@@H]12] |

TABLE 3

| NO. | Structure |
|---|---|
| I-038 | 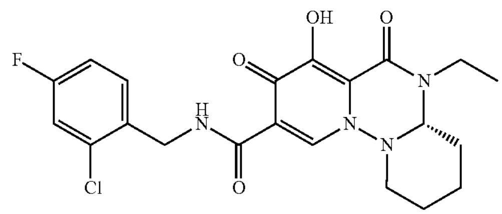 [SMILES: CCN1C(=O)c2c(O)c(=O)c(C(=O)NCc3ccc(F)cc3Cl)cn2N2CCCC[C@@H]12] |
| I-039 | 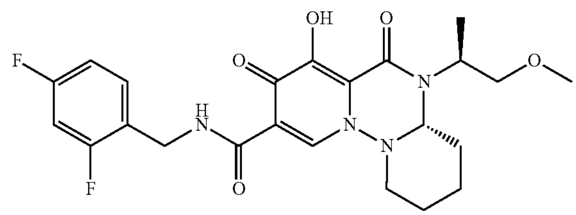 [SMILES: COC[C@H](C)N1C(=O)c2c(O)c(=O)c(C(=O)NCc3ccc(F)cc3F)cn2N2CCCC[C@@H]12] |
| I-040 | 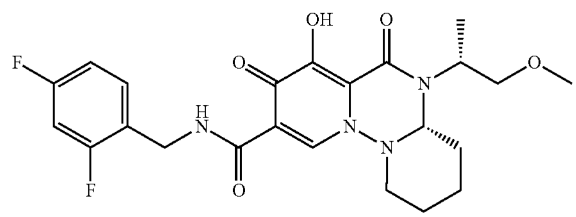 [SMILES: COC[C@@H](C)N1C(=O)c2c(O)c(=O)c(C(=O)NCc3ccc(F)cc3F)cn2N2CCCC[C@@H]12] |
| I-041 | 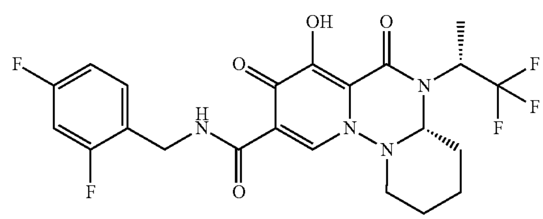 [SMILES: C[C@@H](N1C(=O)c2c(O)c(=O)c(C(=O)NCc3ccc(F)cc3F)cn2N2CCCC[C@@H]12)C(F)(F)F] |
| I-042 | 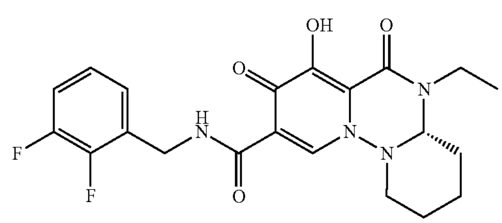 [SMILES: CCN1C(=O)c2c(O)c(=O)c(C(=O)NCc3cccc(F)c3F)cn2N2CCCC[C@@H]12] |
| I-043 | 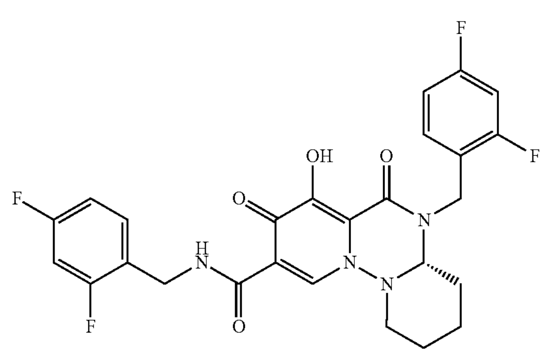 [SMILES: O=C(NCc1ccc(F)cc1F)c1cn2c(c(O)c1=O)C(=O)N(Cc1ccc(F)cc1F)[C@@H]1CCCCN12] |

TABLE 3-continued

| NO. | Structure |
|---|---|
| I-044 | 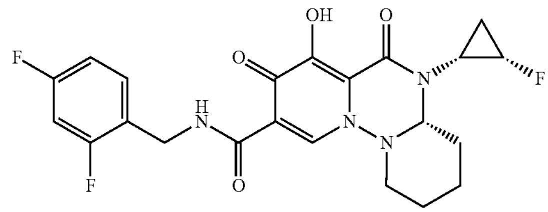 [SMILES: O=C(NCc1ccc(F)cc1F)c1cn2c(c(O)c1=O)C(=O)N([C@@H]1C[C@@H]1F)[C@@H]1CCCCN12] |
| I-045 | 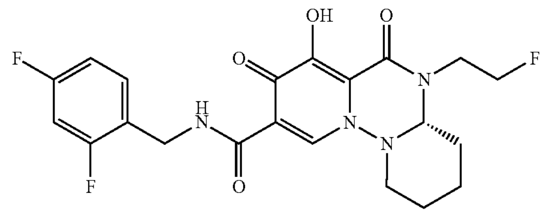 [SMILES: O=C(NCc1ccc(F)cc1F)c1cn2c(c(O)c1=O)C(=O)N(CCF)[C@@H]1CCCCN12] |
| I-046 | 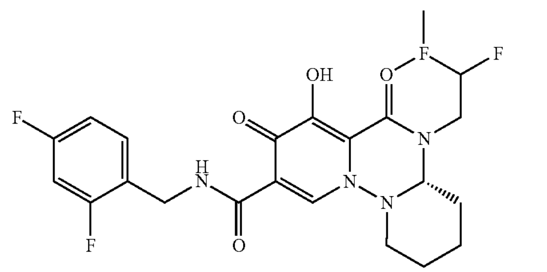 |
| I-047 | 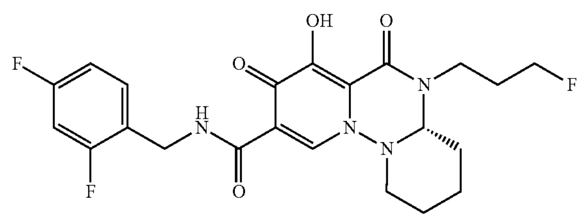 [SMILES: O=C(NCc1ccc(F)cc1F)c1cn2c(c(O)c1=O)C(=O)N(CCCF)[C@@H]1CCCCN12] |
| I-048 | 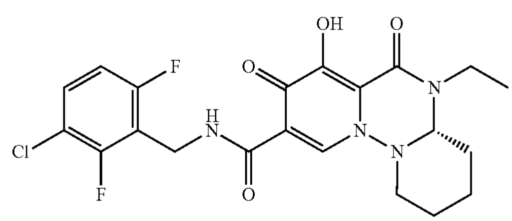 [SMILES: CCN1C(=O)c2c(O)c(=O)c(C(=O)NCc3c(F)ccc(Cl)c3F)cn2N2CCCC[C@@H]12] |
| I-049 | 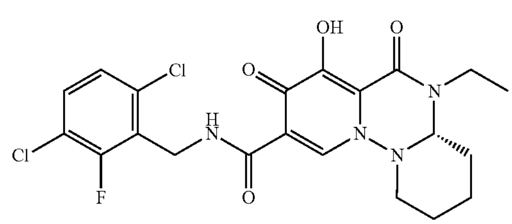 [SMILES: CCN1C(=O)c2c(O)c(=O)c(C(=O)NCc3c(Cl)ccc(Cl)c3F)cn2N2CCCC[C@@H]12] |
| I-051 | 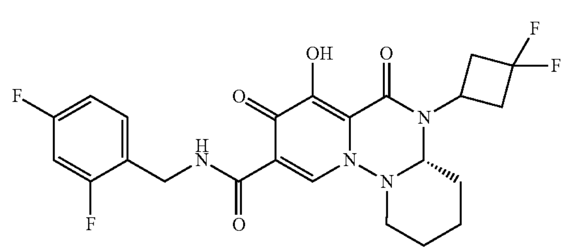 [SMILES: O=C(NCc1ccc(F)cc1F)c1cn2c(c(O)c1=O)C(=O)N(C1CC(F)(F)C1)[C@@H]1CCCCN12] |

TABLE 3-continued

| NO. | Structure |
|---|---|
| I-052 | 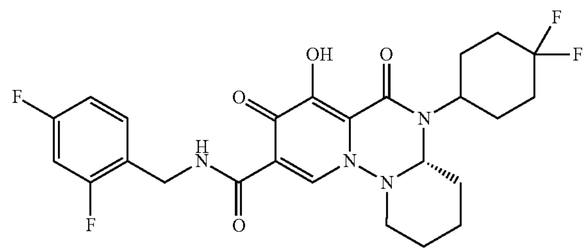 [SMILES: O=C(NCc1ccc(F)cc1F)c1cn2c(c(O)c1=O)C(=O)N(C1CCC(F)(F)CC1)[C@@H]1CCCCN12] |
| I-053 | 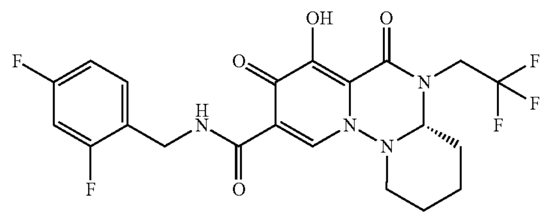 [SMILES: O=C(NCc1ccc(F)cc1F)c1cn2c(c(O)c1=O)C(=O)N(CC(F)(F)F)[C@@H]1CCCCN12] |
| II-001 | 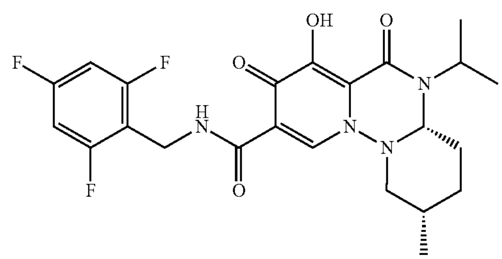 |

TABLE 4

| NO. | Structure |
|---|---|
| II-002 | 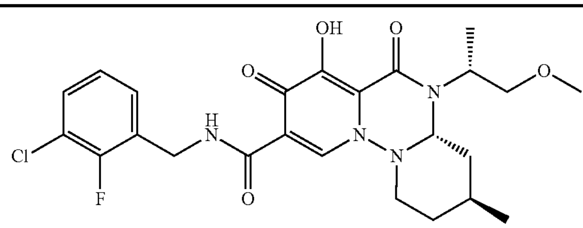 |
| II-003 | 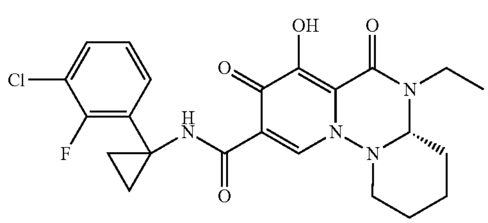 [SMILES: CCN1C(=O)c2c(O)c(=O)c(C(=O)NC3(c4cccc(Cl)c4F)CC3)cn2N2CCCC[C@@H]12] |
| II-005 | 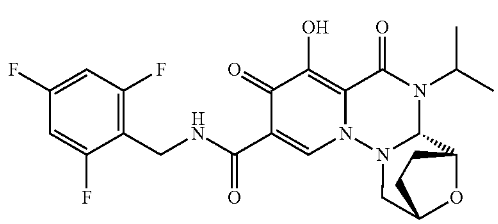 [SMILES: CC(C)N1C(=O)c2c(O)c(=O)c(C(=O)NCc3c(F)cc(F)cc3F)cn2N2C[C@@H]3CC[C@@H](O3)[C@@H]12] |

TABLE 4-continued
| NO. | Structure |
|---|---|
| II-006 | 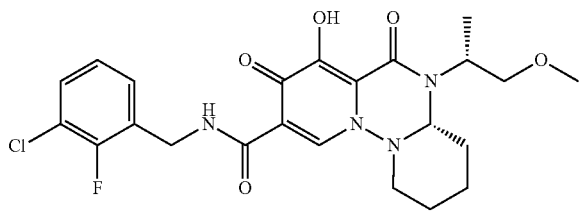 [SMILES: COC[C@@H](C)N1C(=O)c2c(O)c(=O)c(C(=O)NCc3cccc(Cl)c3F)cn2N2CCCC[C@@H]12] |
| II-007 | 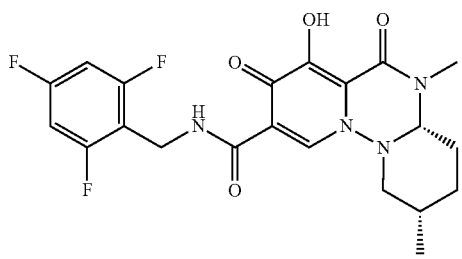 [SMILES: C[C@H]1CC[C@H]2N(C)C(=O)c3c(O)c(=O)c(C(=O)NCc4c(F)cc(F)cc4F)cn3N2C1] |
| II-008 | 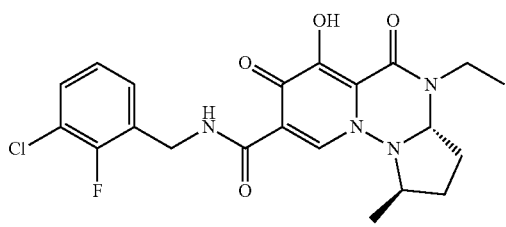 [SMILES: CCN1C(=O)c2c(O)c(=O)c(C(=O)NCc3cccc(Cl)c3F)cn2N2[C@H](C)CC[C@@H]12] |
| II-009 | 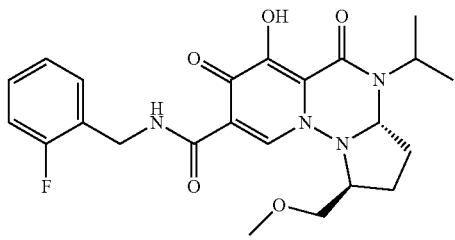 [SMILES: COC[C@@H]1CC[C@H]2N(C(C)C)C(=O)c3c(O)c(=O)c(C(=O)NCc4ccccc4F)cn3N12] |
| II-010 | 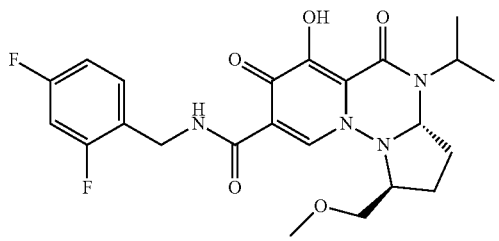 [SMILES: COC[C@@H]1CC[C@H]2N(C(C)C)C(=O)c3c(O)c(=O)c(C(=O)NCc4ccc(F)cc4F)cn3N12] |
| II-011 | 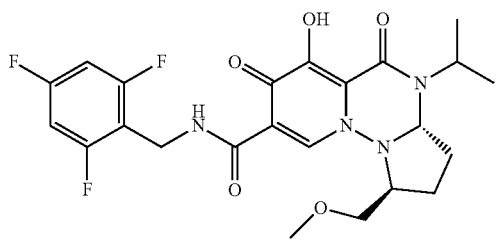 [SMILES: COC[C@@H]1CC[C@H]2N(C(C)C)C(=O)c3c(O)c(=O)c(C(=O)NCc4c(F)cc(F)cc4F)cn3N12] |

TABLE 4-continued
| NO. | Structure |
|---|---|
| II-012 | 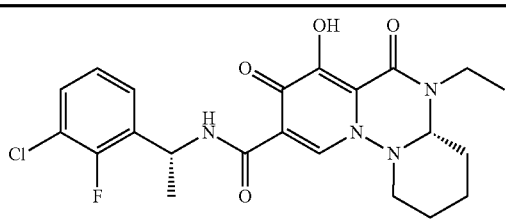 |
| II-013 | 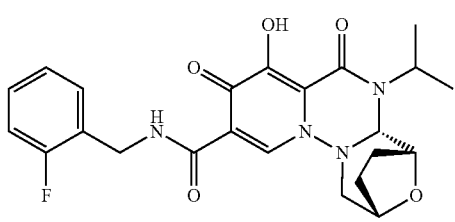 [SMILES: CC(C)N1C(=O)c2c(O)c(=O)c(C(=O)NCc3ccccc3F)cn2N2C[C@@H]3CC[C@@H](O3)[C@@H]12] |
| II-014 | 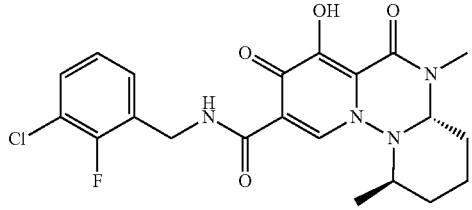 [SMILES: C[C@@H]1CCC[C@H]2N(C)C(=O)c3c(O)c(=O)c(C(=O)NCc4cccc(Cl)c4F)cn3N12] |
| II-015 | 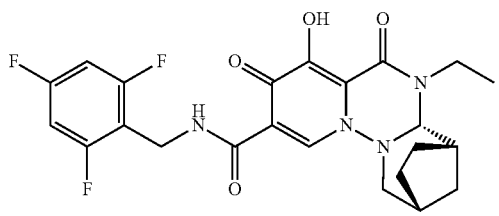 |
| II-016 | 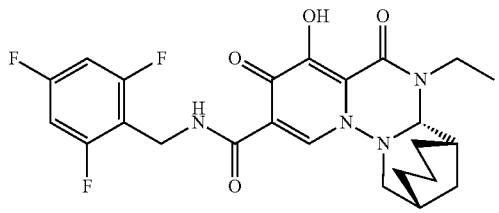 [SMILES: CCN1C(=O)c2c(O)c(=O)c(C(=O)NCc3c(F)cc(F)cc3F)cn2N2C[C@@H]3CCC[C@@H](C3)[C@@H]12] |
| II-017 | 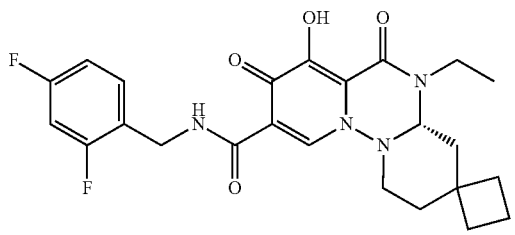 [SMILES: CCN1C(=O)c2c(O)c(=O)c(C(=O)NCc3ccc(F)cc3F)cn2N2CCC3(CCC3)C[C@@H]12] |
| II-018 | 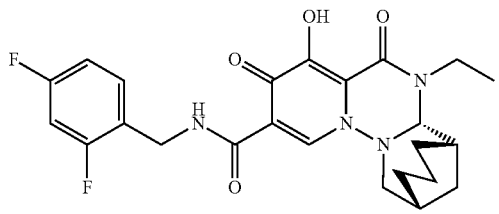 [SMILES: CCN1C(=O)c2c(O)c(=O)c(C(=O)NCc3ccc(F)cc3F)cn2N2C[C@@H]3CCC[C@@H](C3)[C@@H]12] |

TABLE 4-continued
| NO. | Structure |
|---|---|
| II-019 | 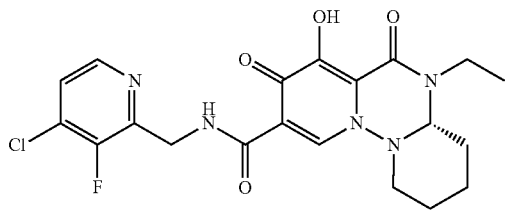 |
| II-020 | 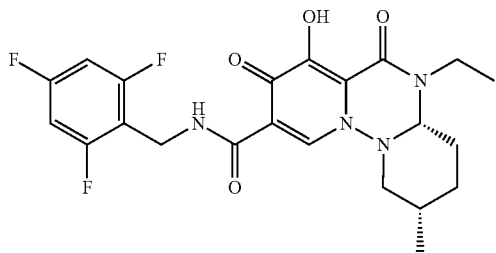 [SMILES: CCN1C(=O)c2c(O)c(=O)c(C(=O)NCc3c(F)cc(F)cc3F)cn2N2C[C@@H](C)CC[C@@H]12] |
TABLE 5
| NO. | Structure |
|---|---|
| II-021 | 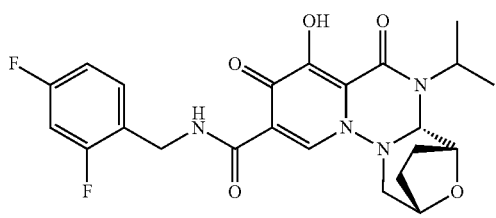 [SMILES: CC(C)N1C(=O)c2c(O)c(=O)c(C(=O)NCc3ccc(F)cc3F)cn2N2C[C@@H]3CC[C@@H](O3)[C@@H]12] |
| II-022 | 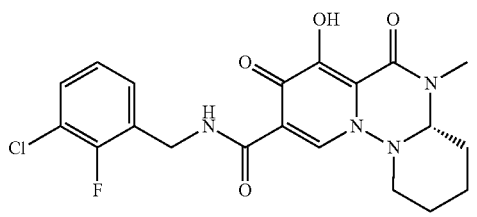 [SMILES: CN1C(=O)c2c(O)c(=O)c(C(=O)NCc3cccc(Cl)c3F)cn2N2CCCC[C@@H]12] |
| II-023 | 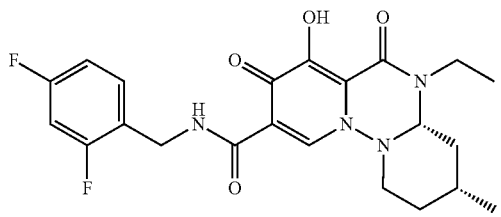 |
| II-024 | 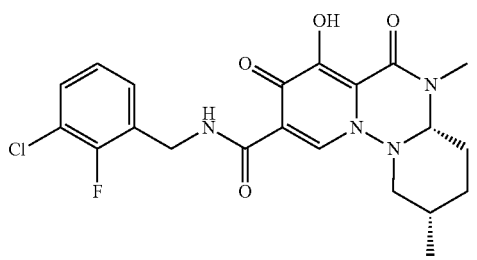 [SMILES: C[C@H]1CC[C@H]2N(C)C(=O)c3c(O)c(=O)c(C(=O)NCc4cccc(Cl)c4F)cn3N2C1] |

TABLE 5-continued

| NO. | Structure |
|---|---|
| II-025 | 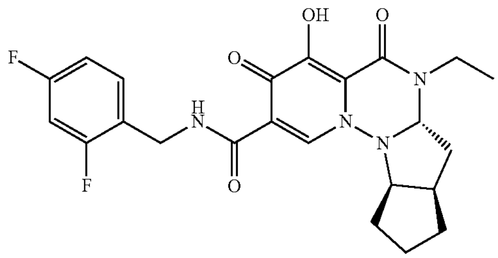 [SMILES: CCN1C(=O)c2c(O)c(=O)c(C(=O)NCc3ccc(F)cc3F)cn2N2[C@@H]3CCC[C@@H]3C[C@@H]12] |
| II-026 | 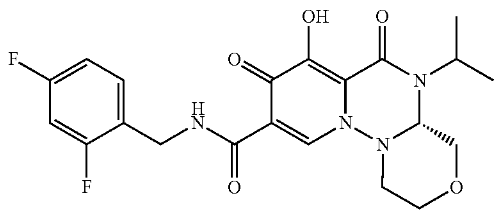 [SMILES: CC(C)N1C(=O)c2c(O)c(=O)c(C(=O)NCc3ccc(F)cc3F)cn2N2CCOC[C@@H]12] |
| II-027 | 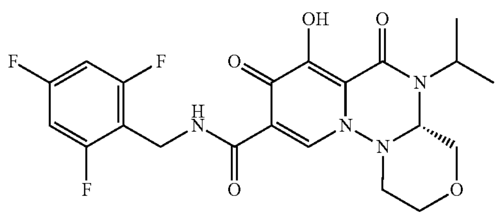 [SMILES: CC(C)N1C(=O)c2c(O)c(=O)c(C(=O)NCc3c(F)cc(F)cc3F)cn2N2CCOC[C@@H]12] |
| II-028 | 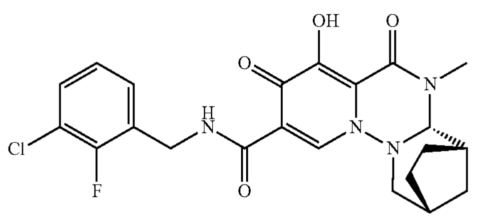 [SMILES: CN1C(=O)c2c(O)c(=O)c(C(=O)NCc3cccc(Cl)c3F)cn2N2C[C@@H]3CC[C@@H](C3)[C@@H]12] |
| II-029 | 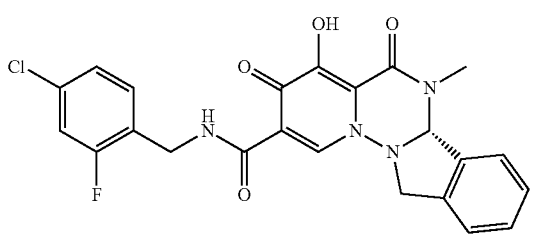 [SMILES: CN1C(=O)c2c(O)c(=O)c(C(=O)NCc3ccc(Cl)cc3F)cn2N2Cc3ccccc3[C@@H]12] |
| II-030 | 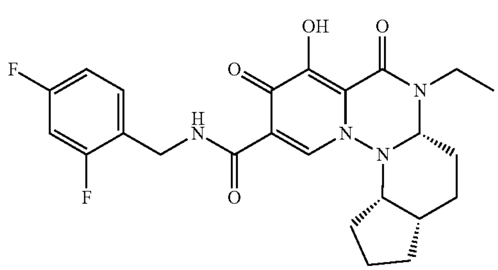 [SMILES: CCN1C(=O)c2c(O)c(=O)c(C(=O)NCc3ccc(F)cc3F)cn2N2[C@H]3CCC[C@H]3CC[C@@H]12] |

TABLE 5-continued
| NO. | Structure |
|---|---|
| II-031 | 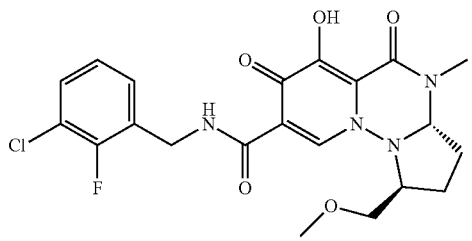 [SMILES: COC[C@@H]1CC[C@H]2N(C)C(=O)c3c(O)c(=O)c(C(=O)NCc4cccc(Cl)c4F)cn3N12] |
| II-032 | 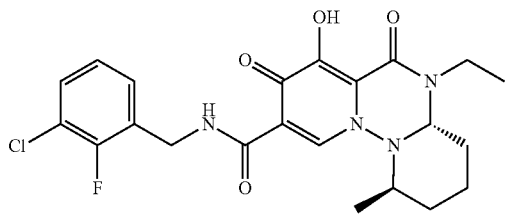 [SMILES: CCN1C(=O)c2c(O)c(=O)c(C(=O)NCc3cccc(Cl)c3F)cn2N2[C@H](C)CCC[C@@H]12] |
| II-033 | 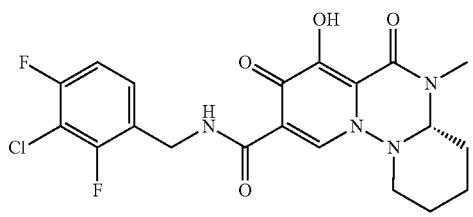 [SMILES: CN1C(=O)c2c(O)c(=O)c(C(=O)NCc3ccc(F)c(Cl)c3F)cn2N2CCCC[C@@H]12] |
| II-034 | 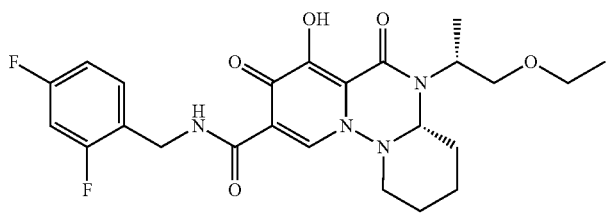 [SMILES: CCOC[C@@H](C)N1C(=O)c2c(O)c(=O)c(C(=O)NCc3ccc(F)cc3F)cn2N2CCCC[C@@H]12] |
| II-035 | 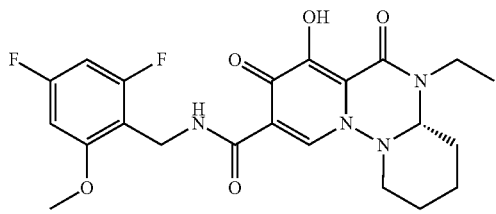 [SMILES: CCN1C(=O)c2c(O)c(=O)c(C(=O)NCc3c(F)cc(F)cc3OC)cn2N2CCCC[C@@H]12] |
| II-036 | 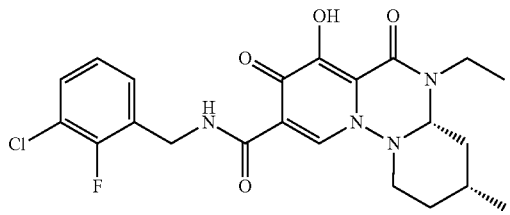 [SMILES: CCN1C(=O)c2c(O)c(=O)c(C(=O)NCc3cccc(Cl)c3F)cn2N2CC[C@@H](C)C[C@@H]12] |
| II-037 | 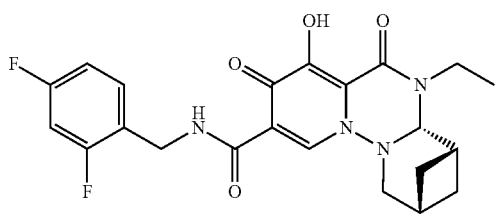 [SMILES: CCN1C(=O)c2c(O)c(=O)c(C(=O)NCc3ccc(F)cc3F)cn2N2C[C@H]3C[C@H](C3)[C@@H]12] |

TABLE 5-continued
| NO. | Structure |
|---|---|
| II-038 | 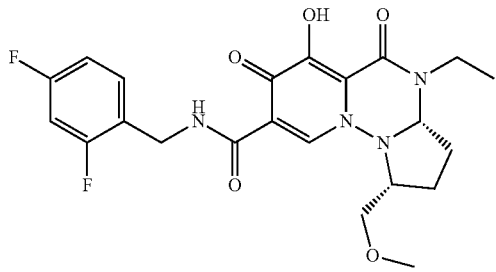 [SMILES: CCN1C(=O)c2c(O)c(=O)c(C(=O)NCc3ccc(F)cc3F)cn2N2[C@@H](COC)CC[C@@H]12] |
TABLE 6
| NO. | Structure |
|---|---|
| II-039 | 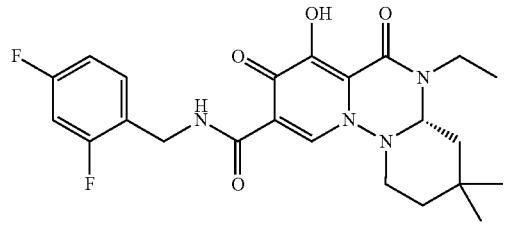 [SMILES: CCN1C(=O)c2c(O)c(=O)c(C(=O)NCc3ccc(F)cc3F)cn2N2CCC(C)(C)C[C@@H]12] |
| II-041 | 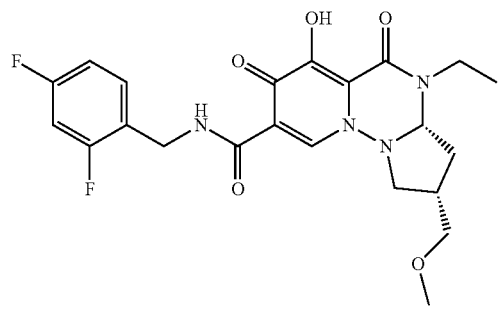 [SMILES: CCN1C(=O)c2c(O)c(=O)c(C(=O)NCc3ccc(F)cc3F)cn2N2C[C@@H](COC)C[C@@H]12] |
| II-042 | 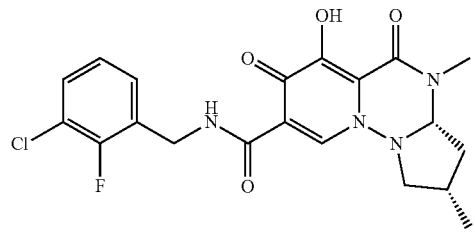 [SMILES: C[C@H]1C[C@H]2N(C)C(=O)c3c(O)c(=O)c(C(=O)NCc4cccc(Cl)c4F)cn3N2C1] |
| II-043 | 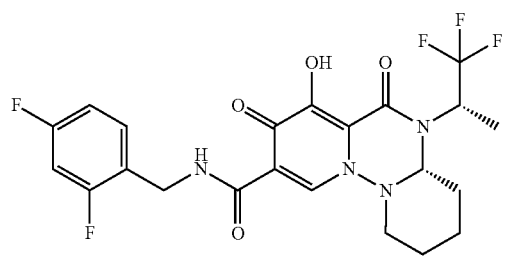 [SMILES: C[C@H](N1C(=O)c2c(O)c(=O)c(C(=O)NCc3ccc(F)cc3F)cn2N2CCCC[C@@H]12)C(F)(F)F] |

TABLE 6-continued

| NO. | Structure |
|---|---|
| II-044 | 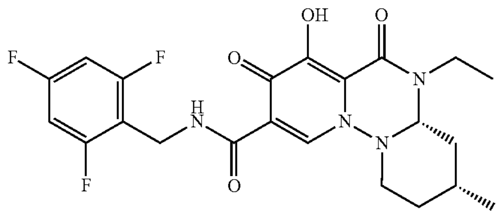 [SMILES: CCN1C(=O)c2c(O)c(=O)c(C(=O)NCc3c(F)cc(F)cc3F)cn2N2CC[C@@H](C)C[C@@H]12] |
| II-045 | 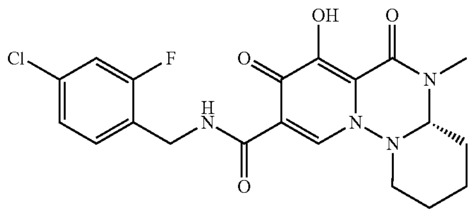 [SMILES: CN1C(=O)c2c(O)c(=O)c(C(=O)NCc3ccc(Cl)cc3F)cn2N2CCCC[C@@H]12] |
| II-046 | 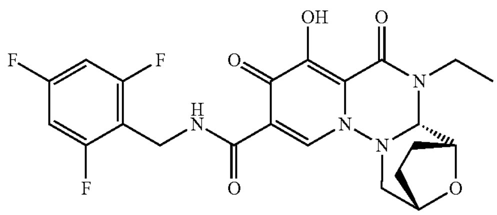 |
| II-047 | 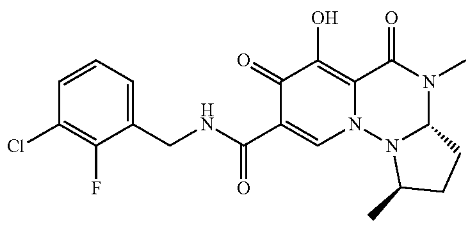 [SMILES: C[C@@H]1CC[C@H]2N(C)C(=O)c3c(O)c(=O)c(C(=O)NCc4cccc(Cl)c4F)cn3N12] |
| II-048 | 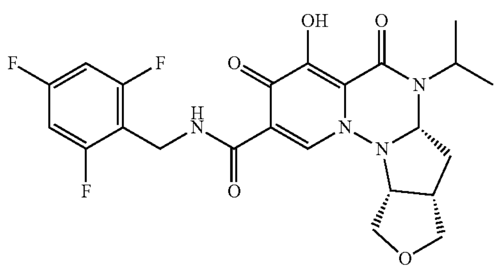 [SMILES: CC(C)N1C(=O)c2c(O)c(=O)c(C(=O)NCc3c(F)cc(F)cc3F)cn2N2[C@H]3COC[C@H]3C[C@@H]12] |
| II-049 | 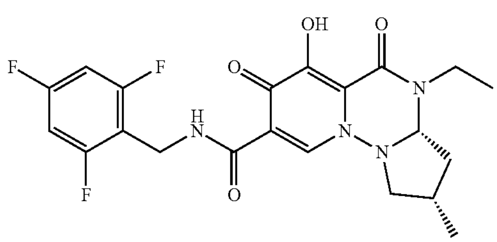 [SMILES: CCN1C(=O)c2c(O)c(=O)c(C(=O)NCc3c(F)cc(F)cc3F)cn2N2C[C@@H](C)C[C@@H]12] |
| II-050 | 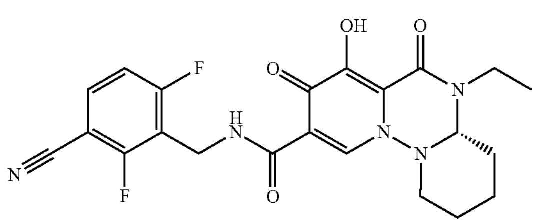 [SMILES: CCN1C(=O)c2c(O)c(=O)c(C(=O)NCc3c(F)ccc(C#N)c3F)cn2N2CCCC[C@@H]12] |

TABLE 6-continued

| NO. | Structure |
|---|---|
| II-051 | 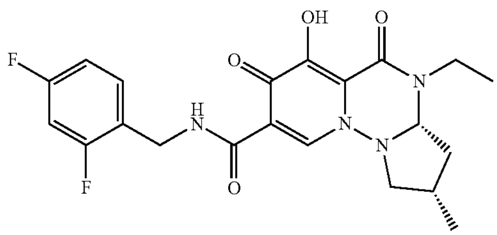 [SMILES: CCN1C(=O)c2c(O)c(=O)c(C(=O)NCc3ccc(F)cc3F)cn2N2C[C@@H](C)C[C@@H]12] |
| II-052 | 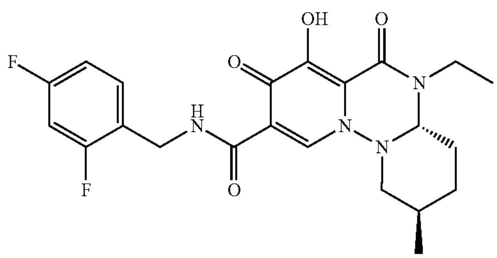 [SMILES: CCN1C(=O)c2c(O)c(=O)c(C(=O)NCc3ccc(F)cc3F)cn2N2C[C@H](C)CC[C@@H]12] |
| II-053 | 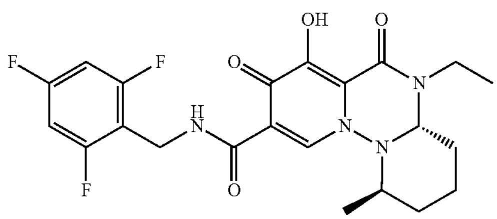 [SMILES: CCN1C(=O)c2c(O)c(=O)c(C(=O)NCc3c(F)cc(F)cc3F)cn2N2[C@H](C)CCC[C@@H]12] |
| II-054 | 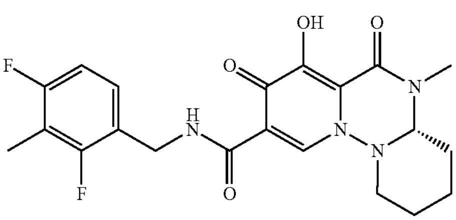 [SMILES: Cc1c(F)ccc(CNC(=O)c2cn3c(c(O)c2=O)C(=O)N(C)[C@@H]2CCCCN23)c1F] |
| II-055 | 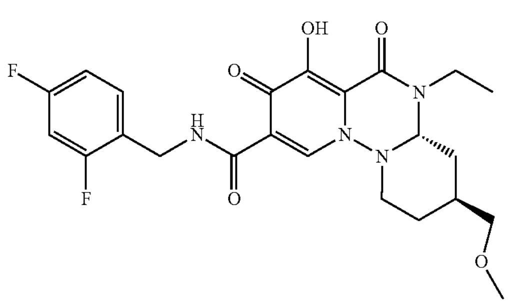 [SMILES: CCN1C(=O)c2c(O)c(=O)c(C(=O)NCc3ccc(F)cc3F)cn2N2CC[C@H](COC)C[C@@H]12] |

TABLE 7

| NO. | Structure |
|---|---|
| II-056 | 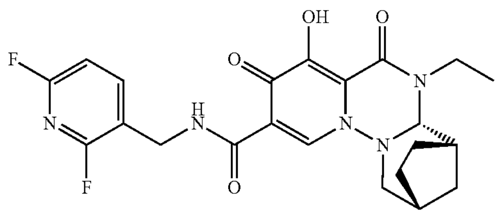 [SMILES: CCN1C(=O)c2c(O)c(=O)c(C(=O)NCc3ccc(F)nc3F)cn2N2C[C@@H]3CC[C@@H](C3)[C@@H]12] |
| II-057 | 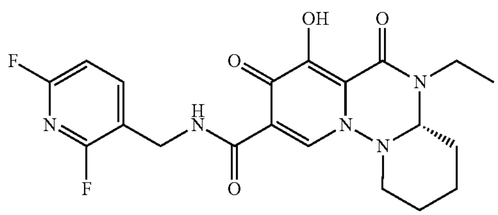 [SMILES: CCN1C(=O)c2c(O)c(=O)c(C(=O)NCc3ccc(F)nc3F)cn2N2CCCC[C@@H]12] |
| II-058 | 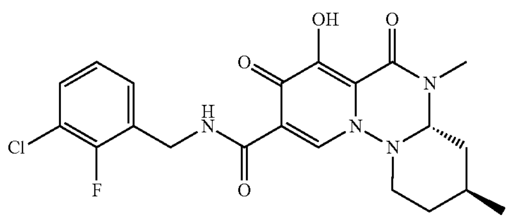 [SMILES: C[C@H]1CCN2[C@@H](C1)N(C)C(=O)c1c(O)c(=O)c(C(=O)NCc3cccc(Cl)c3F)cn12] |
| II-059 | 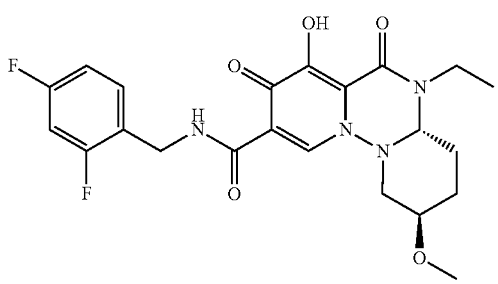 |
| II-060 | 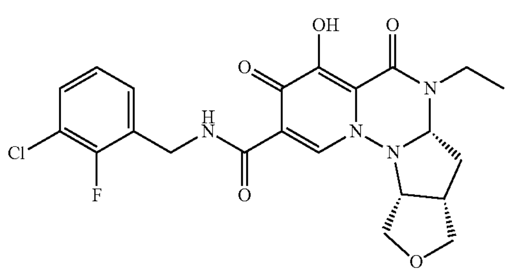 [SMILES: CCN1C(=O)c2c(O)c(=O)c(C(=O)NCc3cccc(Cl)c3F)cn2N2[C@H]3COC[C@H]3C[C@@H]12] |
| II-061 | 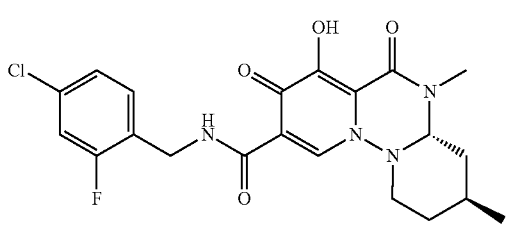 [SMILES: C[C@H]1CCN2[C@@H](C1)N(C)C(=O)c1c(O)c(=O)c(C(=O)NCc3ccc(Cl)cc3F)cn12] |

TABLE 7-continued
| NO. | Structure |
|---|---|
| II-062 | 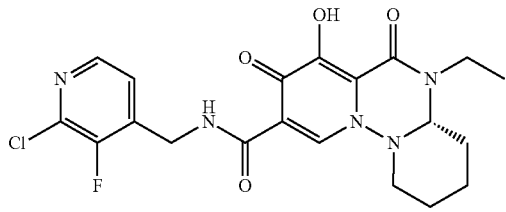 [SMILES: CCN1C(=O)c2c(O)c(=O)c(C(=O)NCc3ccnc(Cl)c3F)cn2N2CCCC[C@@H]12] |
| II-063 | 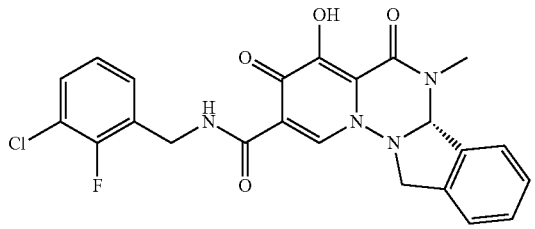 [SMILES: CN1C(=O)c2c(O)c(=O)c(C(=O)NCc3cccc(Cl)c3F)cn2N2Cc3ccccc3[C@@H]12] |
| II-064 | 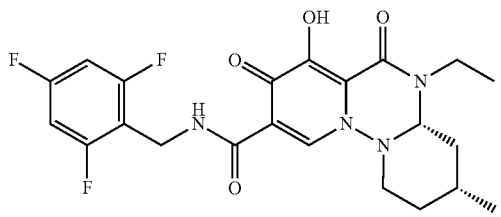 [SMILES: CCN1C(=O)c2c(O)c(=O)c(C(=O)NCc3c(F)cc(F)cc3F)cn2N2CC[C@@H](C)C[C@@H]12] |
| II-065 | 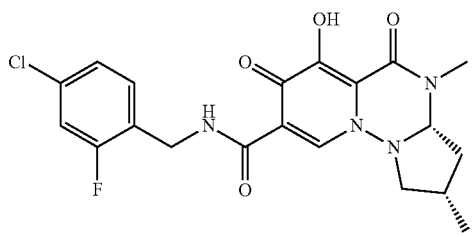 [SMILES: C[C@H]1C[C@H]2N(C)C(=O)c3c(O)c(=O)c(C(=O)NCc4ccc(Cl)cc4F)cn3N2C1] |
| II-066 | 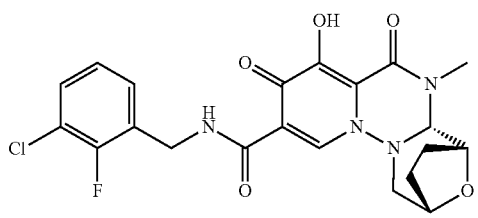 [SMILES: CN1C(=O)c2c(O)c(=O)c(C(=O)NCc3cccc(Cl)c3F)cn2N2C[C@@H]3CC[C@@H](O3)[C@@H]12] |
| II-067 | 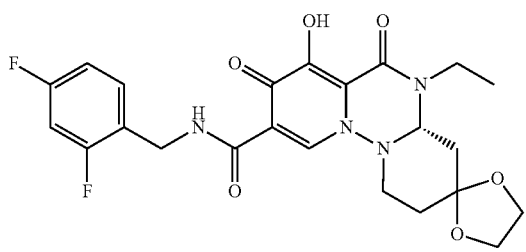 [SMILES: CCN1C(=O)c2c(O)c(=O)c(C(=O)NCc3ccc(F)cc3F)cn2N2CCC3(C[C@@H]12)OCCO3] |
| II-068 | 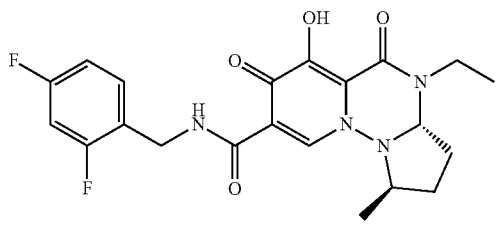 [SMILES: CCN1C(=O)c2c(O)c(=O)c(C(=O)NCc3ccc(F)cc3F)cn2N2[C@H](C)CC[C@@H]12] |

TABLE 7-continued
| NO. | Structure |
|---|---|
| II-069 | 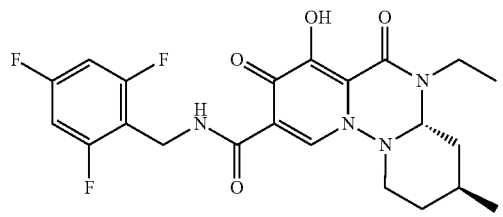 [SMILES: CCN1C(=O)c2c(O)c(=O)c(C(=O)NCc3c(F)cc(F)cc3F)cn2N2CC[C@H](C)C[C@@H]12] |
| II-070 | 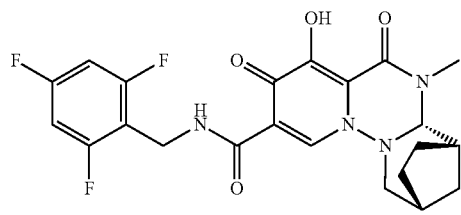 [SMILES: CN1C(=O)c2c(O)c(=O)c(C(=O)NCc3c(F)cc(F)cc3F)cn2N2C[C@@H]3CC[C@@H](C3)[C@@H]12] |
| II-071 | 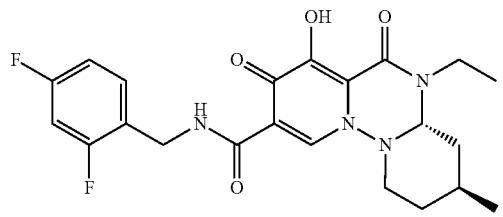 [SMILES: CCN1C(=O)c2c(O)c(=O)c(C(=O)NCc3ccc(F)cc3F)cn2N2CC[C@H](C)C[C@@H]12] |
| II-073 | 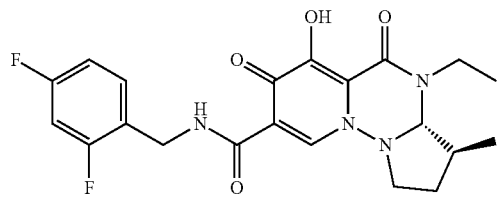 [SMILES: CCN1C(=O)c2c(O)c(=O)c(C(=O)NCc3ccc(F)cc3F)cn2N2CC[C@H](C)[C@@H]12] |
| II-074 | 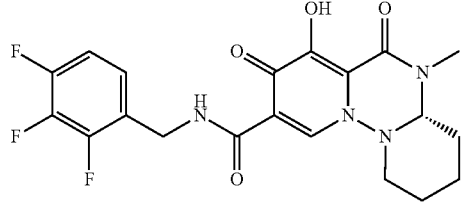 [SMILES: CN1C(=O)c2c(O)c(=O)c(C(=O)NCc3ccc(F)c(F)c3F)cn2N2CCCC[C@@H]12] |
TABLE 8
| NO. | Structure |
|---|---|
| II-075 | 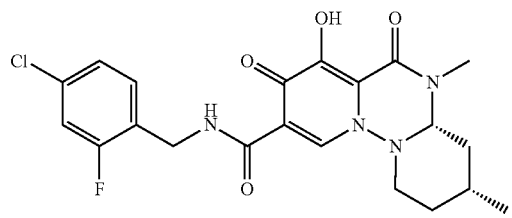 [SMILES: C[C@@H]1CCN2[C@@H](C1)N(C)C(=O)c1c(O)c(=O)c(C(=O)NCc3ccc(Cl)cc3F)cn12] |

TABLE 8-continued
| NO. | Structure |
|---|---|
| II-076 | 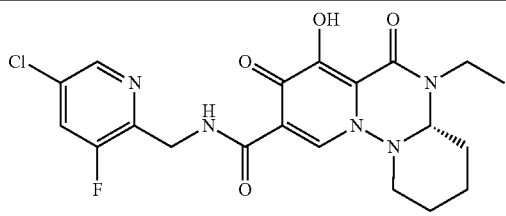 |
| II-077 | 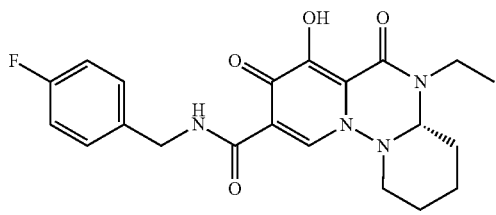 [SMILES: CCN1C(=O)c2c(O)c(=O)c(C(=O)NCc3ccc(F)cc3)cn2N2CCCC[C@@H]12] |
| II-078 | 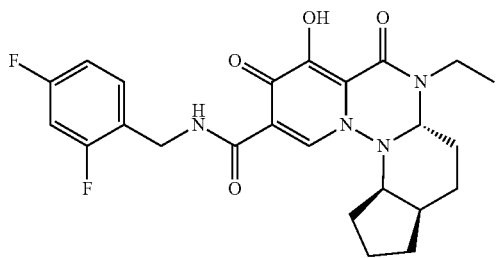 [SMILES: CCN1C(=O)c2c(O)c(=O)c(C(=O)NCc3ccc(F)cc3F)cn2N2[C@@H]3CCC[C@@H]3CC[C@@H]12] |
| II-079 | 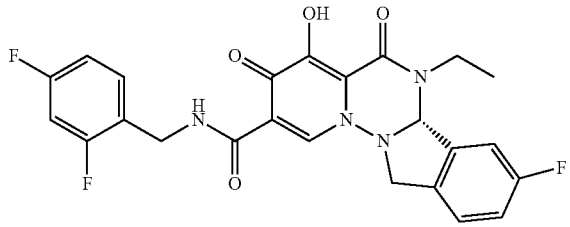 [SMILES: CCN1C(=O)c2c(O)c(=O)c(C(=O)NCc3ccc(F)cc3F)cn2N2Cc3ccc(F)cc3[C@@H]12] |
| II-080 | 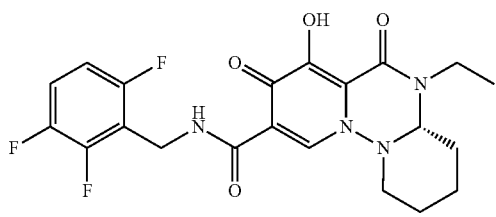 [SMILES: CCN1C(=O)c2c(O)c(=O)c(C(=O)NCc3c(F)ccc(F)c3F)cn2N2CCCC[C@@H]12] |
| II-081 | 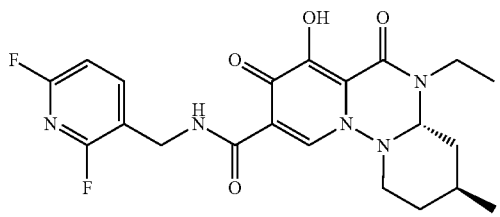 [SMILES: CCN1C(=O)c2c(O)c(=O)c(C(=O)NCc3ccc(F)nc3F)cn2N2CC[C@H](C)C[C@@H]12] |
| II-082 | 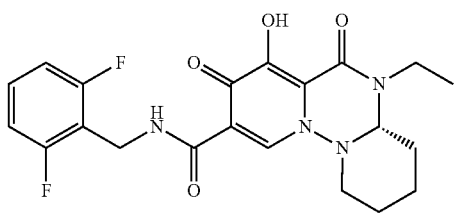 [SMILES: CCN1C(=O)c2c(O)c(=O)c(C(=O)NCc3c(F)cccc3F)cn2N2CCCC[C@@H]12] |

TABLE 8-continued

| NO. | Structure |
|---|---|
| II-083 | 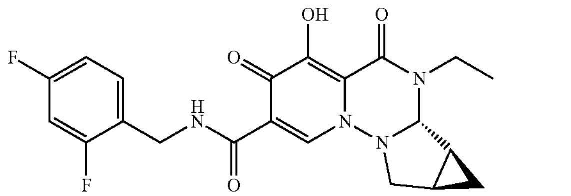 [SMILES: CCN1C(=O)c2c(O)c(=O)c(C(=O)NCc3ccc(F)cc3F)cn2N2C[C@@H]3C[C@@H]3[C@@H]12] |
| II-084 | 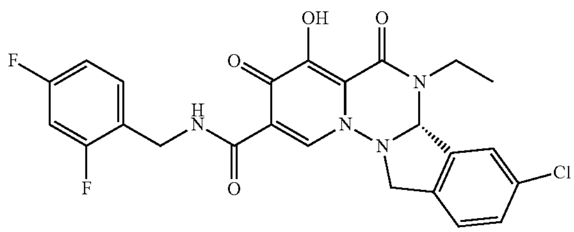 [SMILES: CCN1C(=O)c2c(O)c(=O)c(C(=O)NCc3ccc(F)cc3F)cn2N2Cc3ccc(Cl)cc3[C@@H]12] |
| II-085 | 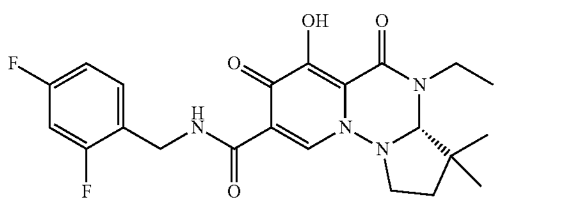 [SMILES: CCN1C(=O)c2c(O)c(=O)c(C(=O)NCc3ccc(F)cc3F)cn2N2CCC(C)(C)[C@@H]12] |
| II-086 | 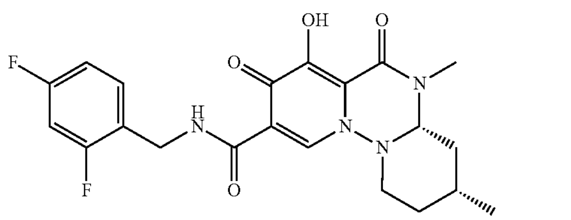 [SMILES: C[C@@H]1CCN2[C@@H](C1)N(C)C(=O)c1c(O)c(=O)c(C(=O)NCc3ccc(F)cc3F)cn12] |
| II-087 | 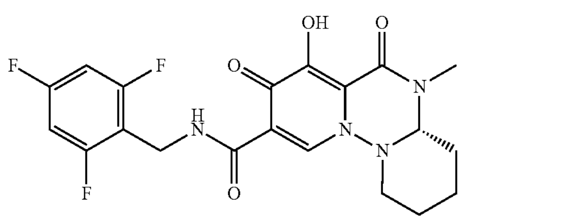 [SMILES: CN1C(=O)c2c(O)c(=O)c(C(=O)NCc3c(F)cc(F)cc3F)cn2N2CCCC[C@@H]12] |
| II-088 | 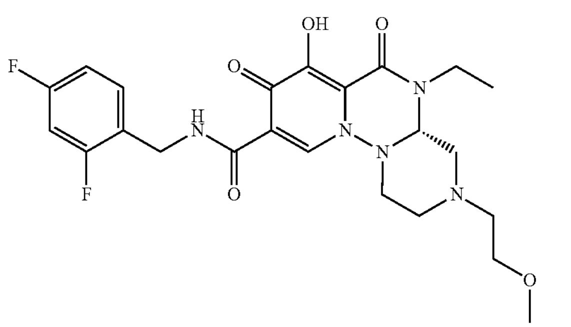 [SMILES: CCN1C(=O)c2c(O)c(=O)c(C(=O)NCc3ccc(F)cc3F)cn2N2CCN(CCOC)C[C@@H]12] |

TABLE 8-continued

| NO. | Structure |
|---|---|
| II-089 | 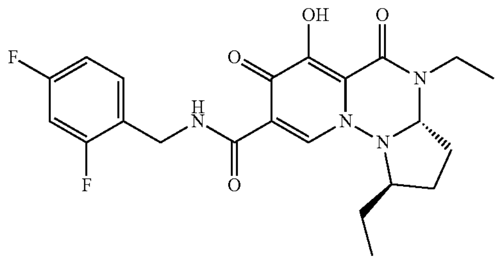 [SMILES: CC[C@@H]1CC[C@H]2N(CC)C(=O)c3c(O)c(=O)c(C(=O)NCc4ccc(F)cc4F)cn3N12] |
| II-090 | 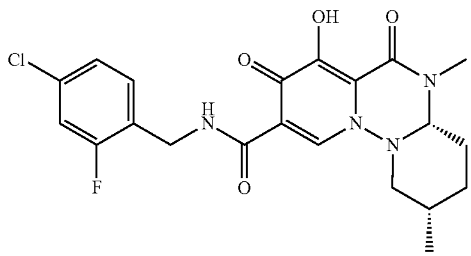 [SMILES: C[C@H]1CC[C@H]2N(C)C(=O)c3c(O)c(=O)c(C(=O)NCc4ccc(Cl)cc4F)cn3N2C1] |

TABLE 9

| NO. | Structure |
|---|---|
| II-091 | 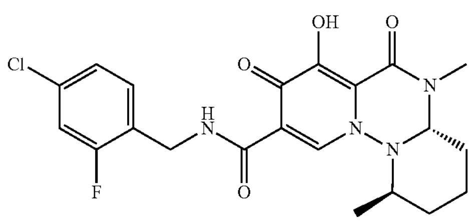 [SMILES: C[C@@H]1CCC[C@H]2N(C)C(=O)c3c(O)c(=O)c(C(=O)NCc4ccc(Cl)cc4F)cn3N12] |
| II-092 | 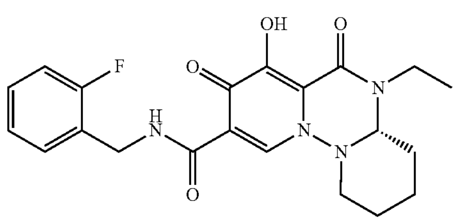 [SMILES: CCN1C(=O)c2c(O)c(=O)c(C(=O)NCc3ccccc3F)cn2N2CCCC[C@@H]12] |
| II-093 | 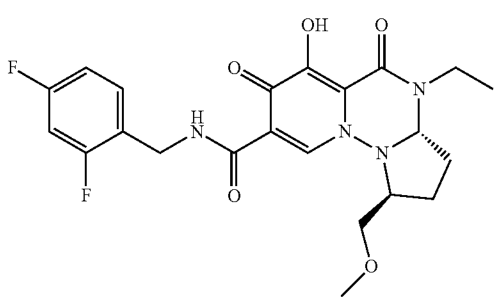 [SMILES: CCN1C(=O)c2c(O)c(=O)c(C(=O)NCc3ccc(F)cc3F)cn2N2[C@H](COC)CC[C@@H]12] |

TABLE 9-continued

| NO. | Structure |
|---|---|
| II-094 | 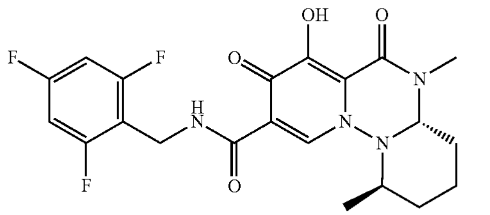 [SMILES: C[C@@H]1CCC[C@H]2N(C)C(=O)c3c(O)c(=O)c(C(=O)NCc4c(F)cc(F)cc4F)cn3N12] |
| II-095 | 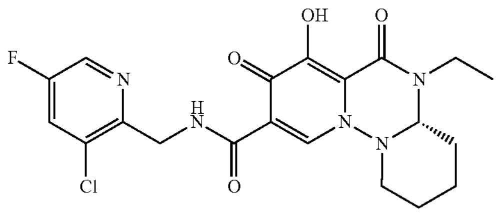 [SMILES: CCN1C(=O)c2c(O)c(=O)c(C(=O)NCc3ncc(F)cc3Cl)cn2N2CCCC[C@@H]12] |
| II-096 | 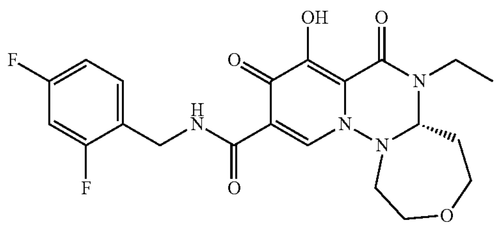 [SMILES: CCN1C(=O)c2c(O)c(=O)c(C(=O)NCc3ccc(F)cc3F)cn2N2CCOCC[C@@H]12] |
| II-097 | 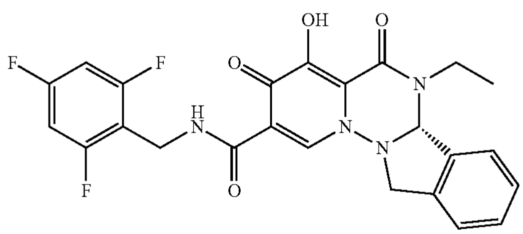 [SMILES: CCN1C(=O)c2c(O)c(=O)c(C(=O)NCc3c(F)cc(F)cc3F)cn2N2Cc3ccccc3[C@@H]12] |
| II-098 | 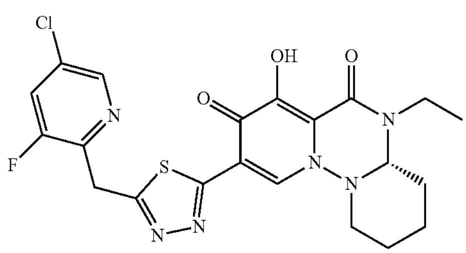 [SMILES: CCN1C(=O)c2c(O)c(=O)c(-c3nnc(Cc4ncc(Cl)cc4F)s3)cn2N2CCCC[C@@H]12] |
| II-099 | 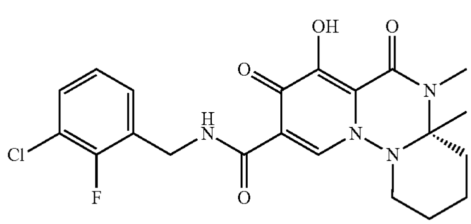 [SMILES: CN1C(=O)c2c(O)c(=O)c(C(=O)NCc3cccc(Cl)c3F)cn2N2CCCC[C@@]12C] |

TABLE 9-continued
| NO. | Structure |
|---|---|
| II-100 | 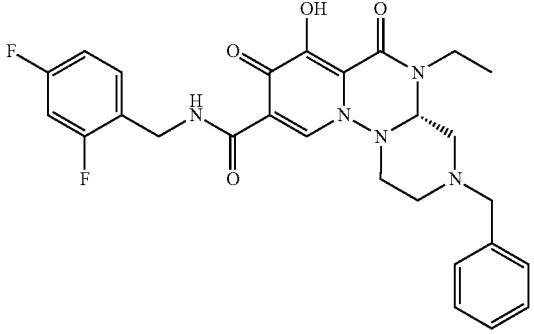 [SMILES: CCN1C(=O)c2c(O)c(=O)c(C(=O)NCc3ccc(F)cc3F)cn2N2CCN(Cc3ccccc3)C[C@@H]12] |
| II-101 | 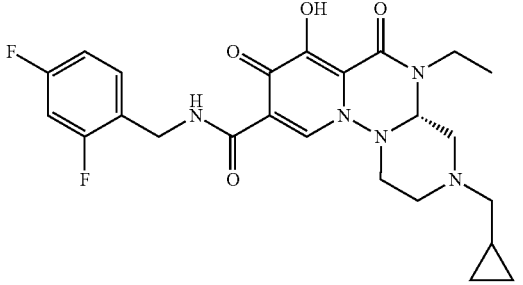 [SMILES: CCN1C(=O)c2c(O)c(=O)c(C(=O)NCc3ccc(F)cc3F)cn2N2CCN(CC3CC3)C[C@@H]12] |
| II-102 | 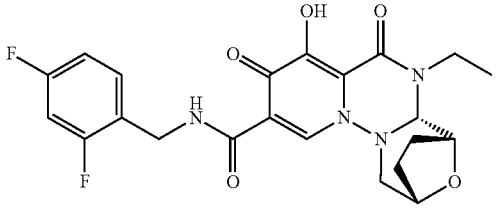 [SMILES: CCN1C(=O)c2c(O)c(=O)c(C(=O)NCc3ccc(F)cc3F)cn2N2C[C@@H]3CC[C@@H](O3)[C@@H]12] |
| II-103 | 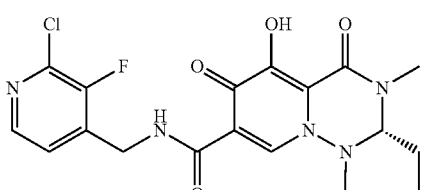 |
| II-104 | 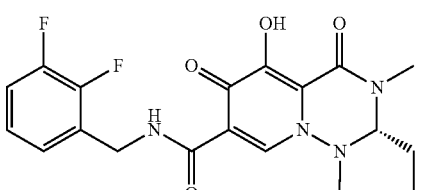 |
| II-105 | 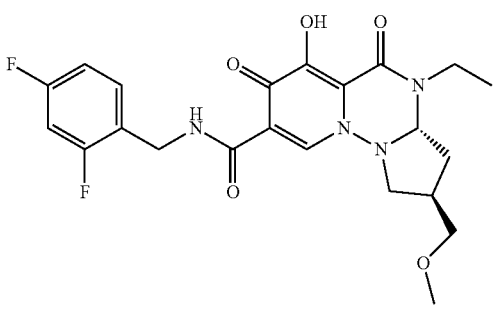 [SMILES: CCN1C(=O)c2c(O)c(=O)c(C(=O)NCc3ccc(F)cc3F)cn2N2C[C@H](COC)C[C@@H]12] |

TABLE 9-continued

| NO. | Structure |
|---|---|
| II-106 | (structure) |

TABLE 10

| NO. | Structure |
|---|---|
| II-107 | (structure) |
| II-108 | (structure) |
| II-109 | (structure) |
| II-110 | (structure) |
| II-111 | (structure) |

TABLE 10-continued
| NO. | Structure |
|---|---|
| II-112 | 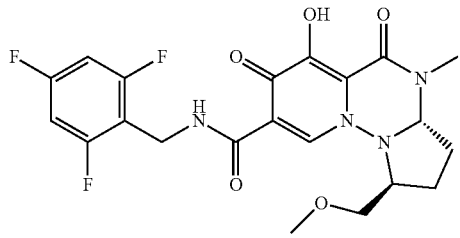 [SMILES: COC[C@@H]1CC[C@H]2N(C)C(=O)c3c(O)c(=O)c(C(=O)NCc4c(F)cc(F)cc4F)cn3N12] |
| II-113 | 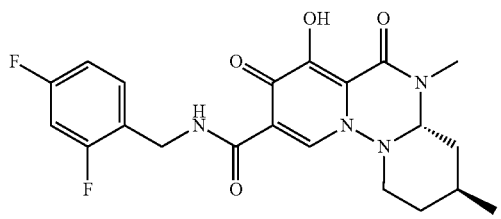 [SMILES: C[C@H]1CCN2[C@@H](C1)N(C)C(=O)c1c(O)c(=O)c(C(=O)NCc3ccc(F)cc3F)cn12] |
| II-114 | 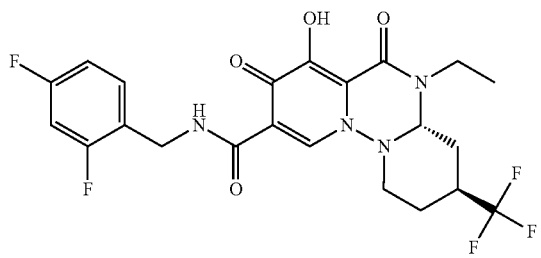 [SMILES: CCN1C(=O)c2c(O)c(=O)c(C(=O)NCc3ccc(F)cc3F)cn2N2CC[C@H](C(F)(F)F)C[C@@H]12] |
| II-115 | 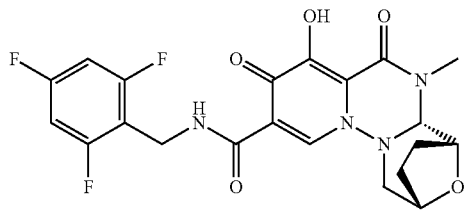 [SMILES: CN1C(=O)c2c(O)c(=O)c(C(=O)NCc3c(F)cc(F)cc3F)cn2N2C[C@@H]3CC[C@@H](O3)[C@@H]12] |
| II-116 | 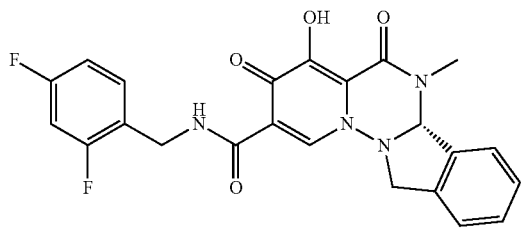 [SMILES: CN1C(=O)c2c(O)c(=O)c(C(=O)NCc3ccc(F)cc3F)cn2N2Cc3ccccc3[C@@H]12] |
| II-117 | 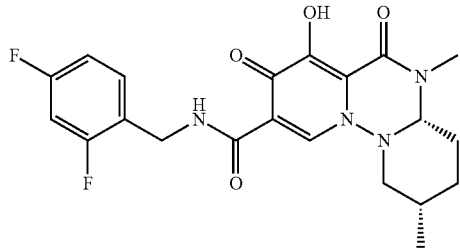 [SMILES: C[C@H]1CC[C@H]2N(C)C(=O)c3c(O)c(=O)c(C(=O)NCc4ccc(F)cc4F)cn3N2C1] |

TABLE 10-continued

| NO. | Structure |
|---|---|
| II-118 | 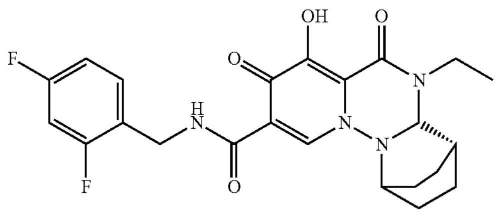 |
| II-119 | 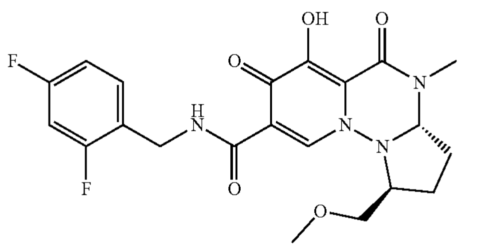 [SMILES: COC[C@@H]1CC[C@H]2N(C)C(=O)c3c(O)c(=O)c(C(=O)NCc4ccc(F)cc4F)cn3N12] |
| II-120 | 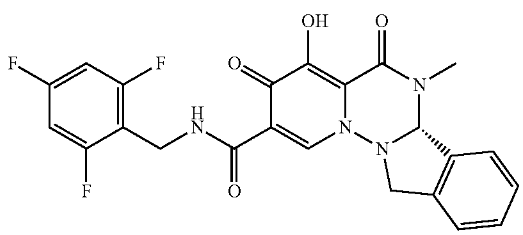 [SMILES: CN1C(=O)c2c(O)c(=O)c(C(=O)NCc3c(F)cc(F)cc3F)cn2N2Cc3ccccc3[C@@H]12] |
| II-121 | 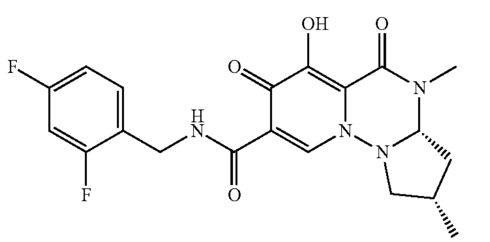 [SMILES: C[C@H]1C[C@H]2N(C)C(=O)c3c(O)c(=O)c(C(=O)NCc4ccc(F)cc4F)cn3N2C1] |
| II-122 | 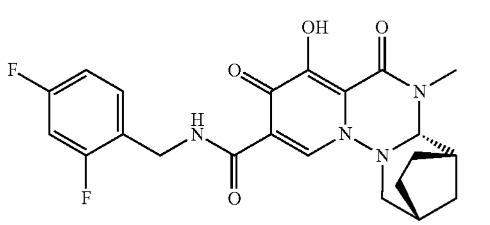 [SMILES: CN1C(=O)c2c(O)c(=O)c(C(=O)NCc3ccc(F)cc3F)cn2N2C[C@@H]3CC[C@@H](C3)[C@@H]12] |
| II-123 | 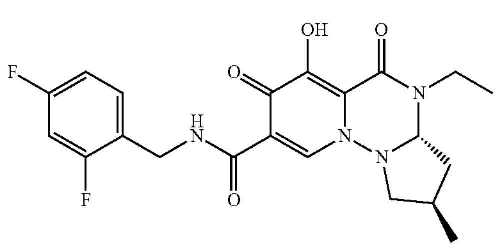 [SMILES: CCN1C(=O)c2c(O)c(=O)c(C(=O)NCc3ccc(F)cc3F)cn2N2C[C@H](C)C[C@@H]12] |

TABLE 10-continued

| NO. | Structure |
|---|---|
| II-124 | 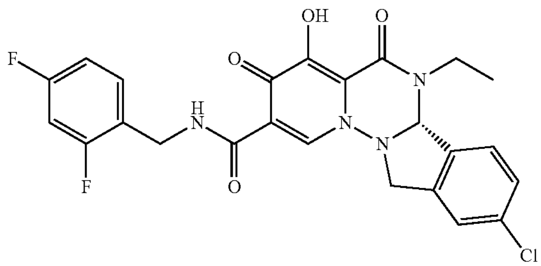 [SMILES: CCN1C(=O)c2c(O)c(=O)c(C(=O)NCc3ccc(F)cc3F)cn2N2Cc3cc(Cl)ccc3[C@@H]12] |

TABLE 11

| NO. | Structure |
|---|---|
| II-125 | 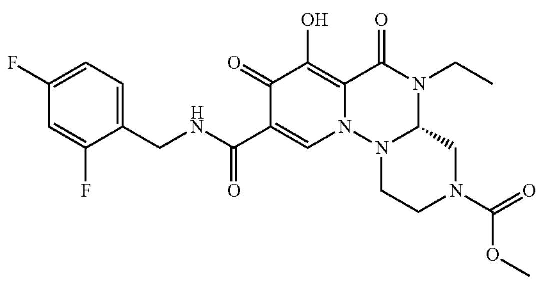 [SMILES: CCN1C(=O)c2c(O)c(=O)c(C(=O)NCc3ccc(F)cc3F)cn2N2CCN(C(=O)OC)C[C@@H]12] |
| II-126 | 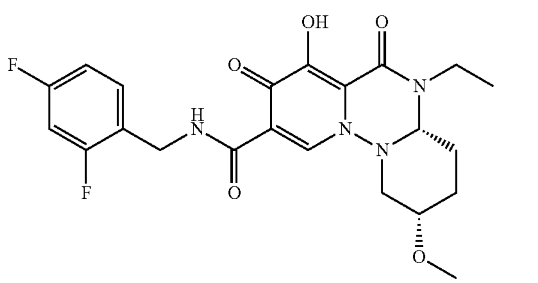 [SMILES: CCN1C(=O)c2c(O)c(=O)c(C(=O)NCc3ccc(F)cc3F)cn2N2C[C@@H](OC)CC[C@@H]12] |
| II-127 | 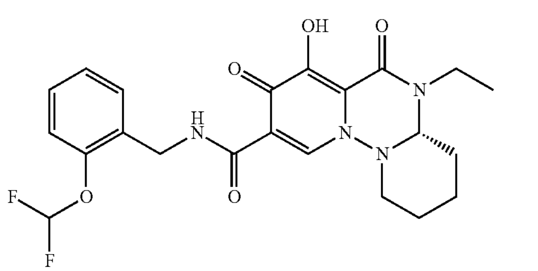 [SMILES: CCN1C(=O)c2c(O)c(=O)c(C(=O)NCc3ccccc3OC(F)F)cn2N2CCCC[C@@H]12] |
| II-128 | 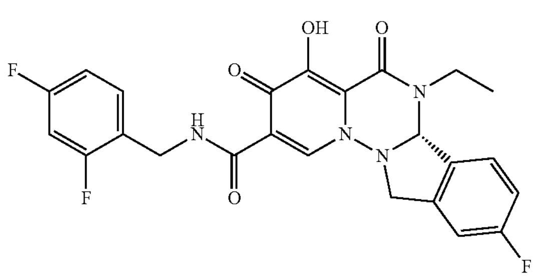 [SMILES: CCN1C(=O)c2c(O)c(=O)c(C(=O)NCc3ccc(F)cc3F)cn2N2Cc3cc(F)ccc3[C@@H]12] |

TABLE 11-continued
| NO. | Structure |
|---|---|
| II-129 | 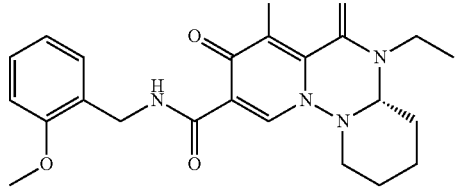 |
| II-130 | 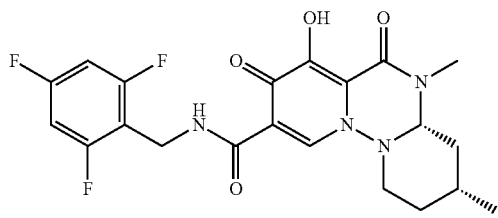 [SMILES: C[C@@H]1CCN2[C@@H](C1)N(C)C(=O)c1c(O)c(=O)c(C(=O)NCc3c(F)cc(F)cc3F)cn12] |
| II-131 | 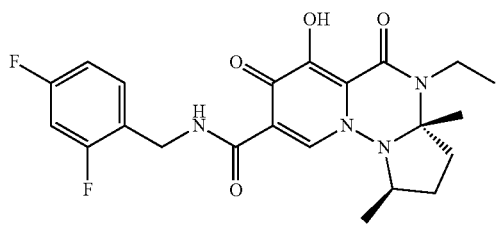 [SMILES: CCN1C(=O)c2c(O)c(=O)c(C(=O)NCc3ccc(F)cc3F)cn2N2[C@H](C)CC[C@@]12C] |
| II-132 | 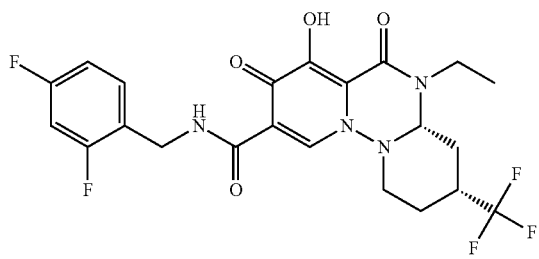 [SMILES: CCN1C(=O)c2c(O)c(=O)c(C(=O)NCc3ccc(F)cc3F)cn2N2CC[C@@H](C(F)(F)F)C[C@@H]12] |
| II-133 | 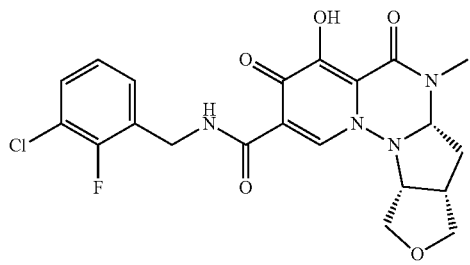 [SMILES: CN1C(=O)c2c(O)c(=O)c(C(=O)NCc3cccc(Cl)c3F)cn2N2[C@H]3COC[C@H]3C[C@@H]12] |
| II-134 | 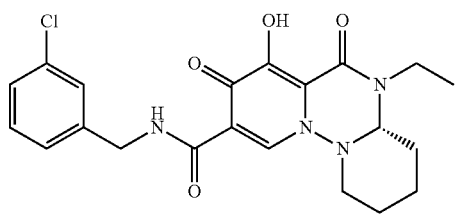 [SMILES: CCN1C(=O)c2c(O)c(=O)c(C(=O)NCc3cccc(Cl)c3)cn2N2CCCC[C@@H]12] |

TABLE 11-continued
| NO. | Structure |
|---|---|
| II-135 | 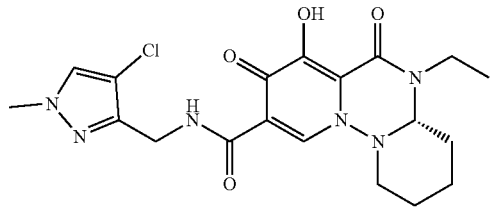 [SMILES: CCN1C(=O)c2c(O)c(=O)c(C(=O)NCc3nn(C)cc3Cl)cn2N2CCCC[C@@H]12] |
| II-136 | 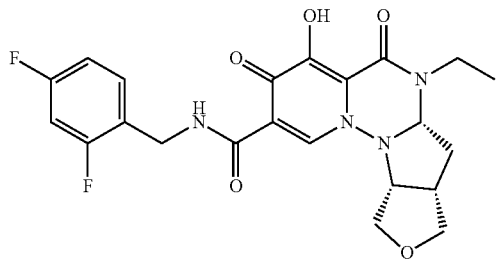 [SMILES: CCN1C(=O)c2c(O)c(=O)c(C(=O)NCc3ccc(F)cc3F)cn2N2[C@H]3COC[C@H]3C[C@@H]12] |
| II-137 | 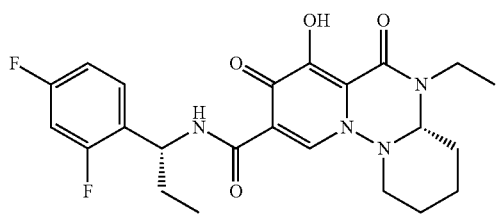 [SMILES: CC[C@@H](NC(=O)c1cn2c(c(O)c1=O)C(=O)N(CC)[C@@H]1CCCCN12)c1ccc(F)cc1F] |
| II-138 | 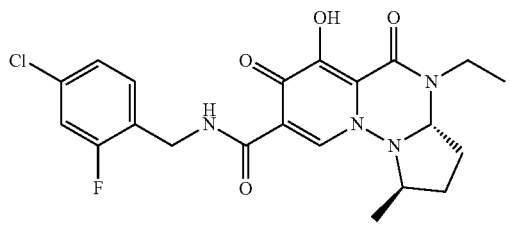 [SMILES: CCN1C(=O)c2c(O)c(=O)c(C(=O)NCc3ccc(Cl)cc3F)cn2N2[C@H](C)CC[C@@H]12] |
| II-139 | 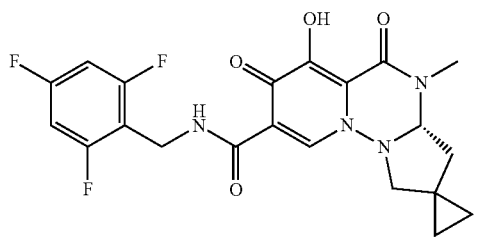 [SMILES: CN1C(=O)c2c(O)c(=O)c(C(=O)NCc3c(F)cc(F)cc3F)cn2N2CC3(CC3)C[C@@H]12] |
| II-140 | 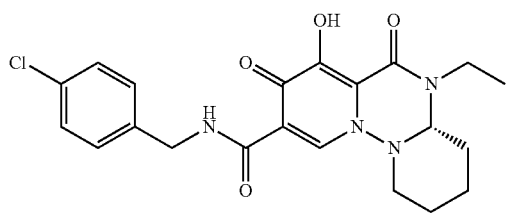 [SMILES: CCN1C(=O)c2c(O)c(=O)c(C(=O)NCc3ccc(Cl)cc3)cn2N2CCCC[C@@H]12] |

TABLE 12
| NO. | Structure |
| --- | --- |
| II-141 | 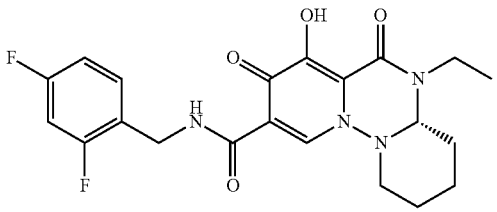 [SMILES: CCN1C(=O)c2c(O)c(=O)c(C(=O)NCc3ccc(F)cc3F)cn2N2CCCC[C@@H]12] |
| II-142 | 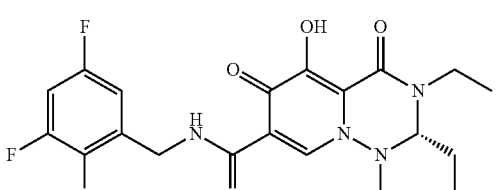 |
| II-143 | 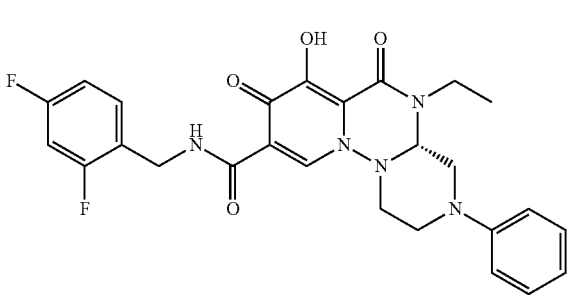 [SMILES: CCN1C(=O)c2c(O)c(=O)c(C(=O)NCc3ccc(F)cc3F)cn2N2CCN(c3ccccc3)C[C@@H]12] |
| II-144 | 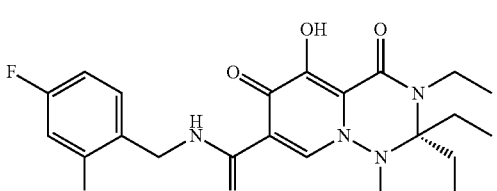 |
| II-145 | 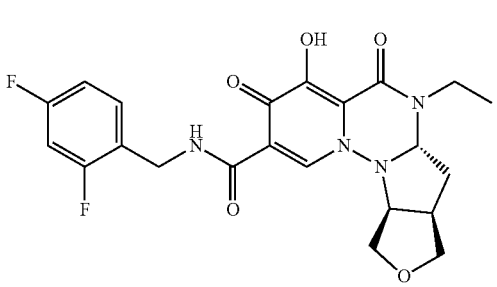 [SMILES: CCN1C(=O)c2c(O)c(=O)c(C(=O)NCc3ccc(F)cc3F)cn2N2[C@@H]3COC[C@@H]3C[C@@H]12] |
| II-146 | 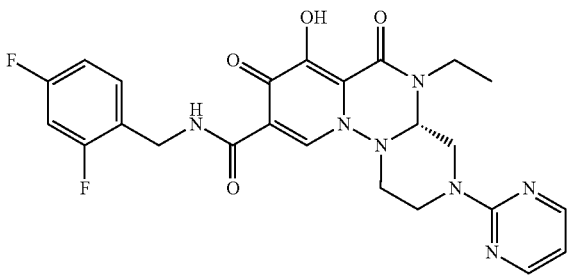 [SMILES: CCN1C(=O)c2c(O)c(=O)c(C(=O)NCc3ccc(F)cc3F)cn2N2CCN(c3ncccn3)C[C@@H]12] |

TABLE 12-continued
| NO. | Structure |
|---|---|
| II-147 | 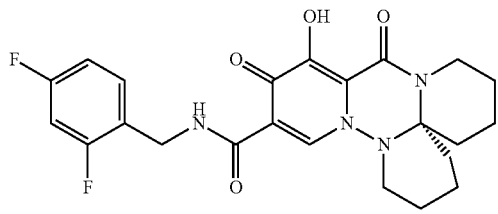 [SMILES: O=C(NCc1ccc(F)cc1F)c1cn2c(c(O)c1=O)C(=O)N1CCCC[C@]13CCCCN23] |
| II-148 | 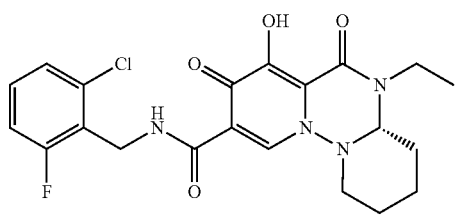 [SMILES: CCN1C(=O)c2c(O)c(=O)c(C(=O)NCc3c(F)cccc3Cl)cn2N2CCCC[C@@H]12] |
| II-149 | 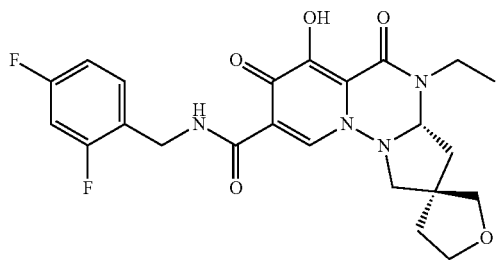 [SMILES: CCN1C(=O)c2c(O)c(=O)c(C(=O)NCc3ccc(F)cc3F)cn2N2C[C@@]3(CCOC3)C[C@@H]12] |
| II-150 | 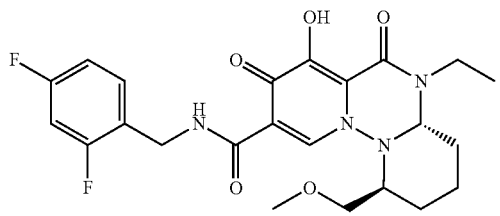 [SMILES: CCN1C(=O)c2c(O)c(=O)c(C(=O)NCc3ccc(F)cc3F)cn2N2[C@H](COC)CCC[C@@H]12] |
| II-151 | 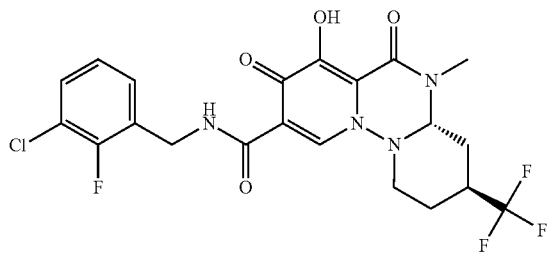 [SMILES: CN1C(=O)c2c(O)c(=O)c(C(=O)NCc3cccc(Cl)c3F)cn2N2CC[C@H](C(F)(F)F)C[C@@H]12] |
| II-152 | 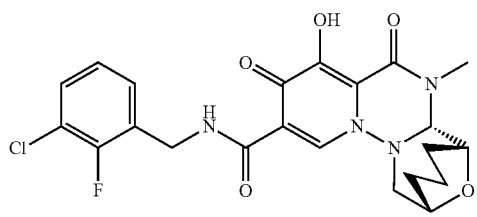 [SMILES: CN1C(=O)c2c(O)c(=O)c(C(=O)NCc3cccc(Cl)c3F)cn2N2C[C@@H]3CCC[C@@H](O3)[C@@H]12] |

TABLE 12-continued

| NO. | Structure |
|---|---|
| II-153 | 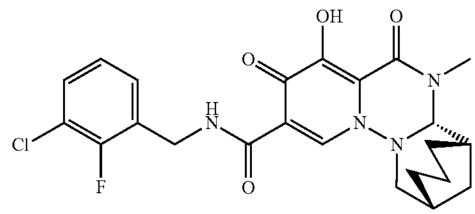 [SMILES: CN1C(=O)c2c(O)c(=O)c(C(=O)NCc3cccc(Cl)c3F)cn2N2C[C@@H]3CCC[C@@H](C3)[C@@H]12] |
| II-154 | 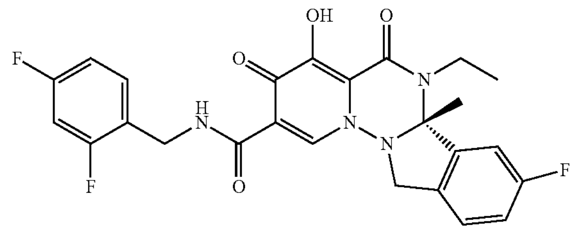 [SMILES: CCN1C(=O)c2c(O)c(=O)c(C(=O)NCc3ccc(F)cc3F)cn2N2Cc3ccc(F)cc3[C@@]12C] |
| II-155 | 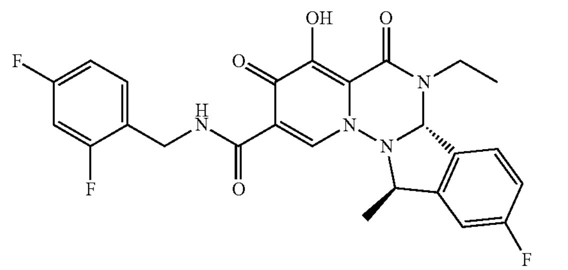 [SMILES: CCN1C(=O)c2c(O)c(=O)c(C(=O)NCc3ccc(F)cc3F)cn2N2[C@H](C)c3cc(F)ccc3[C@@H]12] |
| II-156 | 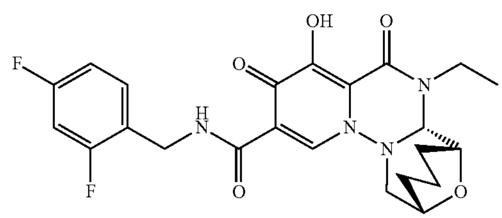 [SMILES: CCN1C(=O)c2c(O)c(=O)c(C(=O)NCc3ccc(F)cc3F)cn2N2C[C@@H]3CCC[C@@H](O3)[C@@H]12] |

TABLE 13

| NO. | Structure |
|---|---|
| II-157 | 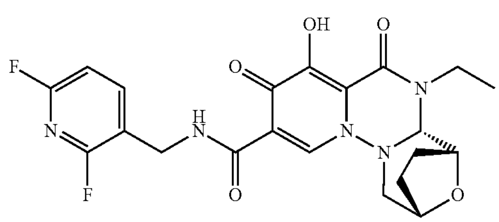 |
| II-158 | 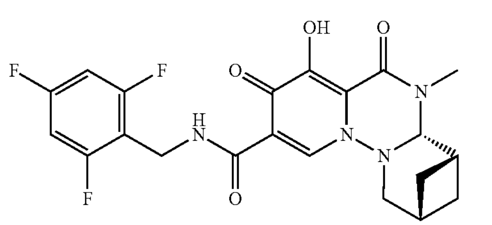 [SMILES: CN1C(=O)c2c(O)c(=O)c(C(=O)NCc3c(F)cc(F)cc3F)cn2N2C[C@H]3C[C@H](C3)[C@@H]12] |
| II-159 | |

Physical data on each compound are shown below.

TABLE 14

| No. | MS | Charge | No. | MS | Charge |
|---|---|---|---|---|---|
| I-001 | 435 | M + H | II-054 | 433 | M + H |
| I-002 | 433 | M + H | II-055 | 478 | M + H |
| I-003 | 467 | M + H | II-056 | 460 | M + H |
| I-004 | 469 | M + H | II-057 | 434 | M + H |
| I-005 | 453 | M + H | II-058 | 449 | M + H |
| I-006 | 447 | M + H | II-059 | 463 | M + H |
| I-007 | 467 | M + H | II-060 | 477 | M + H |

TABLE 14-continued

| No. | MS | Charge | No. | MS | Charge |
|---|---|---|---|---|---|
| I-008 | 433 | M + H | II-061 | 449 | M + H |
| I-009 | 534 | M + H | II-062 | 450 | M + H |
| I-010 | 434 | M − Cl | II-063 | 469 | M + H |
| I-011 | 451 | M + H | II-064 | 479 | M + H |
| I-012 | 447 | M + H | II-065 | 435 | M + H |
| I-013 | 448 | M − Cl | II-066 | 463 | M + H |
| I-014 | 493 | M + H | II-067 | 491 | M + H |
| I-015 | 419 | M + H | II-068 | 433 | M + H |
| I-016 | 463 | M + H | II-069 | 464 | M + H |
| I-017 | 459 | M + H | II-070 | 467 | M + H |
| I-018 | 467 | M + H | II-071 | 447 | M + H |
| I-019 | 449 | M + H | II-072 | 431 | M + H |
| I-020 | 461 | M + H | II-073 | 433 | M + H |
| I-021 | 447 | M + H | II-074 | 437 | M + H |
| I-022 | 489 | M + H | II-075 | 449 | M + H |
| I-023 | 489 | M + H | II-076 | 450 | M + H |
| I-024 | 477 | M + H | II-077 | 415 | M + H |
| I-025 | 451 | M + H | II-078 | 473 | M + H |
| I-026 | 473 | M + H | II-079 | 485 | M + H |
| I-027 | 481 | M + H | II-080 | 451 | M + H |
| I-028 | 459 | M + H | II-081 | 448 | M + H |
| I-029 | 447 | M + H | II-082 | 433 | M + H |
| I-030 | 447 | M + H | II-083 | 431 | M + H |
| I-031 | 445 | M + H | II-084 | 501 | M + H |
| I-032 | 447 | M + H | II-085 | 447 | M + H |
| I-033 | 466 | M + H | II-086 | 431 | M + H |
| I-034 | 449 | M + H | II-087 | 437 | M + H |
| I-035 | 449 | M + H | II-088 | 492 | M + H |
| I-036 | 451 | M + H | II-089 | 447 | M + H |
| I-037 | 451 | M + H | II-090 | 449 | M + H |
| I-038 | 449 | M + H | II-091 | 449 | M + H |
| I-039 | 477 | M + H | II-092 | 415 | M + H |
| I-040 | 477 | M + H | II-093 | 463 | M + H |
| I-041 | 501 | M + H | II-094 | 451 | M + H |
| I-042 | 433 | M + H | II-095 | 450 | M + H |
| I-043 | 531 | M + H | II-096 | 449 | M + H |
| I-044 | 463 | M + H | II-097 | 485 | M + H |
| I-045 | 451 | M + H | II-098 | 491 | M + H |
| I-046 | 469 | M + H | II-099 | 449 | M + H |
| I-047 | 465 | M + H | II-100 | 524 | M + H |
| I-048 | 467 | M + H | II-101 | 488 | M + H |
| I-049 | 483 | M + H | II-102 | 461 | M + H |
| I-050 | 447 | M + H | II-103 | 436 | M + H |
| I-051 | 495 | M + H | II-104 | 419 | M + H |
| I-052 | 523 | M + H | II-105 | 463 | M + H |
| I-053 | 487 | M + H | II-106 | 481 | M + H |
| II-001 | 479 | M + H | II-107 | 449 | M + H |
| II-002 | 507 | M + H | II-108 | 437 | M + H |
| II-003 | 475 | M + H | II-109 | 417 | M + H |
| II-004 | 459 | M + H | II-110 | 491 | M + H |
| II-005 | 493 | M + H | II-111 | 431 | M + H |
| II-006 | 493 | M + H | II-112 | 467 | M + H |
| II-007 | 451 | M + H | II-113 | 433 | M + H |
| II-008 | 449 | M + H | II-114 | 501 | M + H |
| II-009 | 459 | M + H | II-115 | 465 | M + H |
| II-010 | 477 | M + H | II-116 | 453 | M + H |
| II-011 | 495 | M + H | II-117 | 433 | M + H |
| II-012 | 463 | M + H | II-118 | 459 | M + H |
| II-013 | 457 | M + H | II-119 | 449 | M + H |
| II-014 | 449 | M + H | II-120 | 471 | M + H |
| II-015 | 477 | M + H | II-121 | 419 | M + H |
| II-016 | 491 | M + H | II-122 | 445 | M + H |
| II-017 | 473 | M + H | II-123 | 433 | M + H |
| II-018 | 473 | M + H | II-124 | 501 | M + H |
| II-019 | 450 | M + H | II-125 | 492 | M + H |
| II-020 | 465 | M + H | II-126 | 463 | M + H |
| II-021 | 475 | M + H | II-127 | 463 | M + H |
| II-022 | 435 | M + H | II-128 | 485 | M + H |
| II-023 | 447 | M + H | II-129 | 427 | M + H |
| II-024 | 449 | M + H | II-130 | 451 | M + H |
| II-025 | 459 | M + H | II-131 | 447 | M + H |
| II-026 | 449 | M + H | II-132 | 501 | M + H |
| II-027 | 467 | M + H | II-133 | 463 | M + H |
| II-028 | 461 | M + H | II-134 | 431 | M + H |
| II-029 | 469 | M + H | II-135 | 435 | M + H |
| II-030 | 473 | M + H | II-136 | 461 | M + H |
| II-031 | 465 | M + H | II-137 | 461 | M + H |
| II-032 | 463 | M + H | II-138 | 435 | M + H |
| II-033 | 453 | M + H | II-139 | 449 | M + H |
| II-034 | 491 | M + H | II-140 | 431 | M + H |
| II-035 | 463 | M + H | II-141 | 434 | M + H |
| II-036 | 449 | M + H | II-142 | 451 | M + H |
| II-037 | 445 | M + H | II-143 | 510 | M + H |
| II-038 | 463 | M + H | II-144 | 447 | M + H |
| II-039 | 461 | M + H | II-145 | 461 | M + H |
| II-040 | 447 | M + H | II-146 | 512 | M + H |
| II-041 | 463 | M + H | II-147 | 459 | M + H |
| II-042 | 435 | M + H | II-148 | 449 | M + H |
| II-043 | 501 | M + H | II-149 | 475 | M + H |
| II-044 | 465 | M + H | II-150 | 477 | M + H |
| II-045 | 435 | M + H | II-151 | 503 | M + H |
| II-046 | 479 | M + H | II-152 | 477 | M + H |
| II-047 | 435 | M + H | II-153 | 475 | M + H |
| II-048 | 493 | M + H | II-154 | 499 | M + H |
| II-049 | 451 | M + H | II-155 | 499 | M + H |
| II-050 | 458 | M + H | II-156 | 475 | M + H |
| II-051 | 433 | M + H | II-157 | 462 | M + H |
| II-052 | 447 | M + H | II-158 | 449 | M + H |
| II-053 | 465 | M + H | II-159 | 461 | M + H |

Biological test examples for the compound of the present invention are described below.

Any of the compound of the present invention has a marked inhibitory effect on virus integrase.

Specifically, in the evaluation methods described below, the compound of the present invention has EC50 of preferably 100 nM or less, more preferably 10 nM or less, further preferably 5 nM.

Test Example 1: Anti-HIV Activity

Serial dilutions of a test sample were prepared in a 96-well microplate (50 μL/well). 2.5×10 5 cells/mL of a MT-4 cell suspension was dispensed at 100 μL/well to the plate containing the test sample. Then, an HIV virus solution was dispensed at 50 μL/well. The plate was mixed with a plate mixer and cultured for 4 days in a $CO_2$ incubator. An MTT (3-(4,5-dimethylthiazol-2-yl)-2,5-diphenyltetrazolium bromide) solution was dispensed at 30 μL/well. The plate was reacted for 1 hour in a $CO_2$ incubator. 150 μL of the supernatant was removed from each well so as not to take up the cells. 150 μL of a cell lysis solution was added to each well and well mixed with a plate mixer until the cells were completely lysed. The absorbance of the mixed plate was measured at two wavelengths of 560 nm and 690 nm with a microplate reader. A 50% HIV inhibitory concentration (EC50) was determined from a concentration-dependent curve using the following 4 parameter logistic curve fitting model.

$$y = A + ((B-A)/(1+(C/x)^D))$$

A=minimum rate of inhibition (negative control, 0%)
B=maximum rate of inhibition (positive control, 100%)
C=compound concentration at an inflection point
1)=slope coefficient
x=compound concentration
y=rate of inhibition (%)

(Results)

TABLE 15

| NO. | EC50 nM | NO. | EC50 nM |
|---|---|---|---|
| I-001 | 0.52 | II-054 | 0.34 |
| I-002 | 0.63 | II-055 | 0.58 |

TABLE 15-continued

| NO. | EC50 nM | NO. | EC50 nM |
|---|---|---|---|
| I-003 | 1.40 | II-056 | 0.83 |
| I-004 | 0.56 | II-057 | 1.70 |
| I-005 | 1.30 | II-058 | 0.79 |
| I-006 | 0.76 | II-059 | 0.66 |
| I-007 | 4.00 | II-060 | 0.27 |
| I-008 | 2.00 | II-061 | 3.40 |
| I-009 | 1.20 | II-062 | 3.20 |
| I-010 | 1.90 | II-063 | 3.60 |
| I-011 | 2.20 | II-064 | 1.20 |
| I-012 | 4.00 | II-065 | 4.90 |
| I-013 | 5.60 | II-066 | 0.17 |
| I-014 | 10.00 | II-067 | 0.62 |
| I-015 | 3.60 | II-068 | 0.61 |
| I-016 | 1.40 | II-069 | 0.90 |
| I-017 | 6.10 | II-070 | 0.58 |
| I-018 | 2.10 | II-071 | 0.74 |
| I-019 | 1.80 | II-072 | 0.83 |
| I-020 | 1.30 | II-073 | 0.25 |
| I-021 | 1.10 | II-074 | 0.71 |
| I-022 | 1.10 | II-075 | 6.30 |
| I-023 | 0.62 | II-076 | 3.30 |
| I-024 | 2.90 | II-077 | 1.10 |
| I-025 | 1.90 | II-078 | 1.10 |
| I-026 | 3.50 | II-079 | 0.66 |
| I-027 | 0.89 | II-080 | 0.58 |
| I-028 | 1.90 | II-081 | 3.10 |
| I-029 | 12.00 | II-082 | 0.74 |
| I-030 | 36.00 | II-083 | 0.95 |
| I-031 | 0.69 | II-084 | 1.80 |
| I-032 | 1.20 | II-085 | 1.30 |
| I-033 | 2.50 | II-086 | 1.00 |
| I-034 | 1.30 | II-087 | 1.40 |
| I-035 | 3.20 | II-088 | 3.10 |
| I-036 | 1.40 | II-089 | 0.94 |
| I-037 | 2.00 | II-090 | 3.20 |
| I-038 | 0.72 | II-091 | 4.10 |
| I-039 | 4.40 | II-092 | 0.33 |
| I-040 | 0.70 | II-093 | 0.32 |
| I-041 | 0.66 | II-094 | 0.57 |
| I-042 | 0.72 | II-095 | 1.90 |
| I-043 | 3.50 | II-096 | 0.68 |
| I-044 | 1.20 | II-097 | 1.00 |
| I-045 | 0.73 | II-098 | 4.00 |
| I-046 | 0.43 | II-099 | 0.33 |
| I-047 | 1.50 | II-100 | 3.00 |
| I-048 | 1.20 | II-101 | 1.60 |
| I-049 | 2.30 | II-102 | 0.61 |
| I-050 | 0.62 | II-103 | 3.70 |
| I-051 | 0.72 | II-104 | 0.69 |
| I-052 | 5.50 | II-105 | 0.58 |
| I-053 | 0.94 | II-106 | 0.22 |
| II-001 | 1.00 | II-107 | 2.30 |
| II-002 | 0.77 | II-108 | 0.61 |
| II-003 | 6.20 | II-109 | 2.40 |
| II-004 | 0.92 | II-110 | 2.10 |
| II-005 | 0.62 | II-111 | 0.56 |
| II-006 | 0.58 | II-112 | 0.70 |
| II-007 | 0.62 | II-113 | 0.72 |
| II-008 | 1.50 | II-114 | 1.50 |
| II-009 | 2.60 | II-115 | 0.87 |
| II-010 | 1.00 | II-116 | 0.68 |
| II-011 | 0.49 | II-117 | 2.00 |
| II-012 | 3.60 | II-118 | 2.20 |
| II-013 | 0.40 | II-119 | 0.54 |
| II-014 | 0.55 | II-120 | 0.22 |
| II-015 | 0.95 | II-121 | 0.71 |
| II-016 | 0.65 | II-122 | 0.61 |
| II-017 | 1.60 | II-123 | 1.60 |
| II-018 | 2.90 | II-124 | 2.60 |
| II-019 | 0.23 | II-125 | 1.30 |
| II-020 | 1.50 | II-126 | 0.45 |
| II-021 | 0.72 | II-127 | 3.60 |
| II-022 | 0.74 | II-128 | 0.72 |
| II-023 | 0.46 | II-129 | 1.90 |
| II-024 | 1.40 | II-130 | 0.13 |
| II-025 | 1.10 | II-131 | 0.49 |
| II-026 | 0.18 | II-132 | 0.51 |
| II-027 | 0.39 | II-133 | 0.43 |
| II-028 | 1.40 | II-134 | 3.00 |
| II-029 | 3.80 | II-135 | 18.00 |
| II-030 | 0.86 | II-136 | 0.65 |
| II-031 | 0.34 | II-137 | 33.00 |
| II-032 | 1.50 | II-138 | 2.10 |
| II-033 | 0.22 | II-139 | 0.62 |
| II-034 | 0.73 | II-140 | 3.60 |
| II-035 | 1.30 | II-141 | 0.65 |
| II-036 | 3.80 | II-142 | 0.74 |
| II-037 | 0.64 | II-143 | 3.20 |
| II-038 | 2.00 | II-144 | 1.60 |
| II-039 | 2.90 | II-145 | 0.68 |
| II-040 | 2.60 | II-146 | 1.60 |
| II-041 | 0.66 | II-147 | 0.66 |
| II-042 | 3.20 | II-148 | 0.50 |
| II-043 | 1.40 | II-149 | 1.20 |
| II-044 | 0.84 | II-150 | 0.55 |
| II-045 | 2.00 | II-151 | 1.60 |
| II-046 | 0.19 | II-152 | 0.70 |
| II-047 | 0.57 | II-153 | 0.74 |
| II-048 | 0.55 | II-154 | 0.67 |
| II-049 | 0.77 | II-155 | 1.20 |
| II-050 | 2.80 | II-156 | 0.33 |
| II-051 | 0.74 | II-157 | 2.20 |
| II-052 | 0.62 | II-158 | 0.27 |
| II-053 | 1.40 | II-159 | 0.56 |

The test results showed that the compound of the present invention has high anti-HIV activity, thus it has been revealed that the compound of the present invention is useful as an HIV drug.

Test Example 2: Resistance Evaluation Test

Serial dilutions of a test sample were prepared in a 96-well microplate (50 μL/well). 2.5×10 5 cells/mL of a HeLa-CD4 cell suspension was dispensed at 100 μL/well to the plate containing the test sample. Then, an HIV virus solution (wild strain and mutant strain) was dispensed at 50 μL/well. The plate was mixed with a plate mixer and cultured for 3 days in a $CO_2$ incubator. The culture supernatant in each well was removed by suction. A cell lysis buffer in a reporter assay kit was dispensed at 100 μL/well, and the plate was frozen in a freezer (−80° C.). The plate frozen in a freezer was thawed at room temperature, then mixed with a plate mixer, and centrifuged at 1,200 rpm for 5 minutes. The supernatant of each well was dispensed at 20 μL/well to a 96-well microplate (BLACK). A chemiluminescent reagent in the reporter assay kit was dispensed at 100 μL/well and reacted at room temperature for approximately 1 hour. Then, luminescence intensity was measured using MicroBeta TRILUX. A 50% HIV inhibitory concentration (EC50) was determined from a concentration-dependent curve using the following 4 parameter logistic curve fitting model.

$$y=A+((B-A)/(1+(C/x)^D))$$

A=minimum rate of inhibition (negative control, 0%)
B=maximum rate of inhibition (positive control, 100%)
C=compound concentration at an inflection point
D=slope coefficient
x=compound concentration
y=rate of inhibition (%)

The degree of resistance (fold change (FC)) of each mutant strain was calculated according to the following expression.
FC=EC50 of mutant strain/EC50 of wild strain (Results)

FC for the mutant strain 1 (E138K/G140S/Q148H/N155H) and FC for the mutant strain 2 (E92Q/E138T/G140S/Q148H) are shown in the table.

TABLE 16

| NO. | mutant strain 1 | mutant strain 2 |
|---|---|---|
| I-002 | 24 | 22 |
| I-006 | 24 | 16 |
| I-011 | 13 | 10 |
| I-015 | 51 | 18 |
| II-004 | 3.1 | 4.2 |
| II-005 | 3.1 | 7.4 |
| II-009 | 4.6 | 7.7 |
| II-013 | 5.6 | 6.4 |
| II-015 | 5.7 | 7.3 |
| II-018 | 6.1 | 8.7 |
| II-020 | 6.4 | 8.9 |
| II-021 | 6.6 | 9 |
| II-022 | 6.8 | 7.7 |
| II-023 | 7 | 4.2 |
| II-024 | 7.3 | 7 |
| II-026 | 8.1 | 14 |
| II-028 | 9.9 | 15 |
| II-031 | 10 | 6.9 |
| II-040 | 15 | 16 |
| II-041 | 15 | 28 |
| II-042 | 15 | 7.9 |
| II-046 | 17 | 28 |
| II-048 | 17 | 34 |
| II-049 | 18 | 17 |
| II-051 | 19 | 21 |
| II-060 | 22 | 16 |
| II-066 | 25 | 15 |
| II-071 | 27 | 22 |
| II-077 | 32 | 36 |
| II-087 | 38 | 14 |
| II-090 | 38 | 25 |
| II-093 | 39 | 38 |
| II-099 | 44 | 26 |
| II-102 | 47 | 45 |
| II-104 | 48 | 17 |
| II-105 | 48 | 62 |
| II-106 | 49 | 25 |
| II-108 | 50 | 27 |
| II-112 | 53 | 24 |
| II-133 | 76 | 17 |
| II-136 | 78 | 110 |
| II-153 | 18 | 10 |
| II-156 | 26 | 16 |
| II-157 | 36 | 25 |

FC for the mutant strain 3 (E92Q/E1:38K/G140S/Q148H)
Compound 1-15: 7.7
FC for the mutant strain (T97A/E138T/G140S/Q148H)
Compound I-15: 10

From the above test results, it has been revealed that the compound of the present invention has a high resistance barrier and is less likely to generate HIV resistant viruses.

Test Example 3: CYP Inhibition Test

The degrees at which the amounts of respective metabolites produced were inhibited by the compound of the present invention were evaluated in commercially available pooled human liver microsomes by using the O-decthylation of 7-ethoxyresorufin (CYP1A2), the methyl-hydroxylation of tolbutamide (CYP2C9), 4'-hydroxylation of mephenytoin (CYP2C19), the 0-demethylation of dextromethorphan (CYP2D6), and the hydroxylation of terfenadine (CYP3A4), which are the typical substrate metabolism reactions of five human major CYP molecular species (CYP1A2, CYP2C9, CYP2C19, CYP2D6, and CYP3A4), as indexes.

The reaction conditions were as follows: substrate, 0.5 µmol/L ethoxyresorufin (CYP1A2), 100 µmol/L tolbutamide (CYP2C9), 50 µmol/L S-mephenytoin (CYP2C19), 5 µmol/L dextromethorphan (CYP2D6), 1 µmol/L terfenadine (CYP3A4); reaction time, 15 minutes; reaction temperature, 37° C.; enzyme, pooled human liver microsome 0.2 mg protein/mL; concentration of the compound of the present invention, 1, 5, 10, 20 µmol/L (four points).

Each five kinds of substrates, human liver microsomes, or the compound of the present invention in 50 mmol/L Hepes buffer were added to a 96-well plate at the composition as described above, and NADPH, as a coenzyme, was added to initiate metabolism reactions. After the incubation at 37° C. for 15 minutes, a methanol/acetonitrile=1/1 (V/V) solution was added to stop the reaction. After centrifugation at 3000 rpm for 15 minutes, resorufin (CYP1A2 metabolite) in the centrifugation supernatant was quantified using a fluorescence multilabel counter or LC/MS/MS, and tolbutamide hydroxide (CYP2C9 metabolite), mephenytoin 4'-hydroxide (CYP2C19 metabolite), dextrorphan (CYP2D6 metabolite), and terfenadine alcohol (CYP3A4 metabolite) in the centrifugation supernatants were quantified by LC/MS/MS.

Only a solvent DMSO, which was used for dissolving the compound, was added to the reaction solution instead of the compound of the present invention, and the mixture was used as a control (100%). Remaining activity (%) was calculated, and $IC_{50}$ was calculated by inverse estimation based on a logistic model using the concentrations and the rates of suppression.

Test Example 4: CYP3A4 (MDZ) MBI Test

This test as to the inhibition of CYP3A4 by the compound of the present invention is to evaluate mechanism based inhibition (MBI) ability from enhancement in inhibitory effect, caused by a metabolism reaction, of the compound of the present invention. CYP3A4 inhibition was evaluated using pooled human liver microsomes by 1-hydroxylation reaction of midazolam (MDZ) as a marker reaction.

The reaction conditions were as follows: substrate, 10 µmol/L MDZ; pre-reaction time, 0 or 30 minutes; substrate metabolic reaction time, 2 minutes; reaction temperature, 37° C.; protein content of pooled human liver microsomes, at pre-reaction 0.5 mg/mL, at reaction 0.05 mg/mL (at 10-fold dilution); concentrations of the compound of the present invention at pre-reaction, 1, 5, 10, 20 µmol/L (four points) or 0.83, 5, 10, 20 µmol/L (four points).

Pooled human liver microsomes and a solution of the compound of the present invention in K-Pi buffer (pH 7.4) as a pre-reaction solution were added to a 96-well plate at the composition of the pre-reaction. A part of the pre-reaction solution was transferred to another 96-well plate, and 1/10 diluted by K-Pi buffer containing a substrate. NADPH as a coenzyme was added to initiate a reaction as a marker reaction (No pre-reaction: Preincubation 0 min). After a predetermined time of the reaction, a solution of methanol/acetonitrile=1/1 (V/V) was added to stop the reaction. In addition, NADPH was added to a remaining pre-reaction solution to initiate a pre-reaction (Pre-reaction was performed: Preincubation 30 min). After a predetermined time of the pre-reaction, a part was transferred to another plate, and 1/10 diluted by K-Pi buffer containing a substrate to initiate a reaction as a marker reaction. After a predetermined time of the reaction, a solution of methanol/acetonitrile=1/1 (V/V) was added to stop the reaction. After the plate in which each marker reaction was performed was centrifuged at 3000 rpm for 15 minutes, 1-hydroxymidazolam in the supernatant was quantified by LC/MS/MS.

The sample obtained by adding only DMSO that is a solvent dissolving a compound instead of the compound of the present invention to a reaction mixture is adopted as a control (100%). Remaining activity (%) is calculated at each concentration of the compound of the present invention compared to the control, and IC value is calculated by reverse-presumption by a logistic model using a concentration and an inhibition rate. A shifted IC value is calculated from IC of Preincubation 0 min/IC of Preincubation 30 min. Shifted IC of 1.5 or more is graded as positive (+), and shifted IC of 1.0 or less is graded as negative (−).
(Result)
Compound I-15: (−)
Compound II-066: (−)

Test Example 5: BA Test

Materials and Methods for Experiments to Evaluate Oral Absorption
(1) Animals used: rats were used.
(2) Rearing conditions: the rats were allowed to freely take solid feed and sterilized tap water.
(3) Dose and grouping setting: a predetermined dose was orally administered and intravenously administered. Groups were set as follows (dose was changed on a compound basis):
 Oral administration: 2 to 60 μmol/kg or 1 to 30 mg/kg (n=2 to 3)
 Intravenous administration: 1 to 30 μmol/kg or 0.5 to 10 mg/kg (n=2 to 3)
(4) Preparation of dosing solution: the test sample was administered as a solution or a suspension for the oral administration. Intravenous administration was performed after solubilization.
(5) Routes of administration: Oral administration was performed mandatory into the stomach by oral sonde. Intravenous administration was performed from caudal vein by syringes with needle.
(6) Evaluation item: blood was collected over time, and the concentration of the compound of the present invention in plasma was measured using LC/MS/MS.
(7) Statistical analysis: an area under concentration in plasma-time curve (AUC) was calculated as to change in the concentration of the compound of the present invention in plasma by the moment analysis method, and the bioavailability (BA) of the compound of the present invention was calculated from the dose ratio and AUC ratio between the oral administration group and the intravenous administration group.

Test Example 6: Clearance Evaluation Test

Experimental Material and Method
(1) Animals used: rats were used.
(2) Rearing conditions: the rats were allowed to freely take solid feed and sterilized tap water.
(3) Dose and grouping setting: a predetermined dose was intravenously administered. Groups were set as follows:
 Intravenous administration: 1 μmol/kg (n=2)
(4) Preparation of dosing solution: the test sample was solubilized using a solvent of dimethyl sulfoxide/propylene glycol=1/1 and administered.
(5) Administration method: the test sample was administered to the tail vein through a syringe with an injection needle.

(6) Evaluation item: blood was collected over time, and the concentration of the compound of the present invention in plasma was measured using LC/MS/MS.
(7) Statistical analysis: total body clearance (CLtot) and elimination half-life (t1/2) were calculated as to change in the concentration of the compound of the present invention in plasma by the moment analysis method.
Compound 1-15: 0.111 mL/min/kg, 12.3 hr
Compound 11-028: 0.102 mL/min/kg, 26.7 hr
The results showed that the compound of the present invention has small clearance and long half-life, thus it has been revealed that the compound of the present invention is useful as a long-acting integrase inhibitor.

Test Example 7 (Metabolic Stability Test)

Commercially available pooled human liver microsomes were reacted with the compound of the present invention for a certain time. A residual rate was calculated by the comparison between the reacted sample and an unreacted sample to evaluate the degree at which the compound of the present invention is metabolized in the liver.

A reaction was performed (oxidative reaction) at 37° C. for 0 minutes or 30 minutes in the presence of 1 mmol/L NADPH in 0.2 mL of a buffer (50 mmol/L Tris-HCl pH 7.4, 150 mmol/L potassium chloride, 10 mmol/L magnesium chloride) containing 0.5 mg protein/mL of human liver microsomes. After the reaction, 50 μL of the reaction solution was added to 100 μL of a solution of methanol/acetonitrile=1/1 (v/v) and mixed, and the mixture was centrifuged at 3000 rpm for 15 minutes. The compound of the present invention in the centrifugation supernatant was quantified by LC/MS/MS or solid-phase extraction (SPE)/MS. The amount of the compound of the present invention remaining after the reaction was calculated with the amount of the compound at 0 minutes of the reaction defined as 100%.
(Results) The residual rate of the compound at a concentration of 0.5 μmol/L is shown in the following table.

TABLE 17

| NO. | residual rate | NO. | residual rate | NO. | residual rate |
|---|---|---|---|---|---|
| I-002 | 103 | II-028 | 74.2 | II-099 | 88.6 |
| I-006 | 92.5 | II-031 | 86 | II-102 | 101 |
| I-011 | 88 | II-040 | 88.3 | II-104 | 96.9 |
| I-015 | 103 | II-041 | 94.3 | II-105 | 84.3 |
| II-004 | 81.6 | II-042 | 97.4 | II-106 | 96.1 |
| II-005 | 80.2 | II-046 | 88.4 | II-108 | 97.2 |
| II-009 | 80.8 | II-048 | 73.3 | II-112 | 90 |
| II-013 | 87 | II-049 | 83.2 | II-133 | 101 |
| II-015 | 74.3 | II-051 | 96 | II-136 | 77.2 |
| II-018 | 77.6 | II-060 | 61.6 | II-153 | 75.4 |
| II-020 | 90.7 | II-066 | 97.7 | II-156 | 98.6 |
| II-021 | 89.1 | II-071 | 104 | II-157 | 105 |
| II-022 | 101 | II-077 | 100 | | |
| II-023 | 82.9 | II-087 | 105 | | |
| II-024 | 84.1 | II-090 | 95.7 | | |
| II-026 | 87.5 | II-093 | 97.5 | | |

Test Example 8: Fluctuation Ames Test

Mutagenicity of the compound of the present invention was evaluated. 20 μL of freezing-stored rat typhoid *bacillus* (*Salmonella typhimurium* TA98 strain, TA100 strain) was inoculated on 10 mL of a liquid nutrient medium (2.5% Oxoid nutrient broth No. 2), and this was pre-cultured with shaking at 37° C. for 10 hours. For the TA98 strain, 7.70 to 8.00 mL of the bacterial solution was centrifuged (2000×g, 10 minutes) to remove the culture medium. The bacteria were suspended in a Micro F buffer ($K_2HPO_4$: 3.5 g/L, $KH_2PO_4$: 1 g/L, $(NH_4)_2SO_4$: 1 g/L, trisodium citrate dihydrate: 0.25 g/L, and $MgSO_4 \cdot 7H_2O$: 0.1 g/L) with the same volume as that of the bacterial solution used for centrifugation. The suspension was added to 120 mL of Exposure medium (Micro F buffer containing biotin: 8 μg/mL, histidine: 0.2 μg/mL, and glucose: 8 mg/mL). For the TA100 strain, 3.10 to 3.42 mL of the bacterial solution was added to 120 to 130 mL of the Exposure medium to prepare a test bacterial solution. Each 12 μL of DMSO solution of the compound of the present invention (several stage dilution from the maximum dose 50 mg/mL at 2 to 3 fold ratio), DMSO as a negative control, and 50 μg/mL of 4-nitroquinoline-1-oxide DMSO solution for the TA98 strain, 0.25 μg/mL of 2-(2-furyl)-3-(5-nitro-2-furyl)acrylamide DMSO solution for the TA100 strain under a non-metabolism activating condition, 40 μg/mL of 2-aminoanthracene DMSO solution for the TA98 strain, 20 μg/mL of 2-aminoanthracene DMSO solution for the TA100 strain under a metabolism activating condition as a positive control, and 588 μL of the test bacterial solution (a mixed solution of 498 μl of the test bacterial solution and 90 μL of S9 mix under the metabolism activating condition) were mixed, and this was cultured with shaking at 37° C. for 90 minutes. 460 μL of the bacterial solution exposed to the compound of the present invention was mixed with 2300 μL of Indicator medium (Micro F buffer containing 8 μg/mL biotin, 0.2 μg/mL histidine, 8 mg/mL glucose, 37.5 μg/mL bromocresol purple), each 50 μL was dispensed to microplate 48 wells/dose, and this was subjected to stationary culturing at 37° C. for 3 days. Since a well containing a bacterium which has obtained the growth ability by mutation of an amino acid (histidine) synthesizing enzyme gene turns from purple to yellow due to a pH change, the bacterium growth well which has turned to yellow in 48 wells per dose was counted, and was assessed by comparing with a negative control group. (−) means that mutagenicity is negative and (+) means that mutagenicity is positive.

Test Example 9: hERG Test

For the purpose of assessing risk of the QT interval prolongation of the electrocardiogram of the compound of the present invention, effects of the compound of the present invention on delayed rectifier $K^+$ current ($I_{Kr}$), which plays an important role in the ventricular repolarization process, was studied using CHO cells expressing human ether-a-go-go related gene (hERG) channel.

After a cell is retained at a membrane potential of −80 mV by whole cell patch clamp method using an automated patch clamp system (QPatch; Sophion Bioscience A/S) and gave a leak potential of −50 mV, $I_{Kr}$ induced by depolarization stimulation at +20 mV for 2 seconds and, further, repolarization stimulation at −50 mV for 2 seconds, was recorded. A solution of 0.1% dimethylsulfoxide in an extracellular solution (NaCl: 145 mmol/L, KCl: 4 mmol/L, $CaCl_2$: 2 mmol/L, $MgCl_2$: 1 mmol/L, glucose: 10 mmol/L, HEPES (4-(2-hydroxyethyl)-1-piperazineethanesulfonic acid): 10 mmol/L, pH=7.4) is used as a vehicle. The vehicle and a solution of the compound of the present invention dissolved at an objective concentration in the extracellular solution are respectively applied to the cell for 7 minutes or more at room temperature. From the obtained $I_{Kr}$, an absolute value of the maximum tail current was measured based on the current value at the resting membrane potential using analysis software (QPatch Assay software; Sophion Bioscience A/S). The maximum tail current after the application of the compound of the present invention with respect to the maximum tail current after the application of the vehicle was further calculated as the rate of inhibition to evaluate the influence of the compound of the present invention on $I_{Kr}$.

Test Example 10: Solubility Test

The solubility of the compound of the present invention was determined under conditions of 1% DMSO addition. A 10 mmol/L solution of the compound was prepared with DMSO. 2 μL of the solution of the compound of the present invention was respectively added to 198 μL of JP-1 fluid or JP-2 fluid. After shaking at room temperature for 1 hour, the mixed solutions were filtered by suction. The filtrates were diluted 10- or 100-fold with methanol/water=1/1 (V/V) or acetonitrile/methanol/water=1/1/2 (V/V/V), and concentrations in the filtrates were measured by the absolute calibration curve method using LC/MS or solid-phase extraction (SPE)/MS.

The composition of the JP-1 fluid is as follows.
Water is added to 2.0 g of sodium chloride and 7.0 mL of hydrochloric acid to reach 1000 mL.
The composition of the JP-2 fluid is as follows.
1 volume of water is added to 1 volume of the solution in which 3.40 g of potassium dihydrogen phosphate and 3.55 g of anhydrous disodium hydrogen phosphate are dissolved in water to reach 1000 mL.

Test Example 11: Powder Solubility Test

An appropriate amount of the compound of the present invention was placed in appropriate containers, and 200 μL of JP-1 fluid (water is added to 2.0 g of sodium chloride and 7.0 mL of hydrochloric acid to reach 1000 mL), JP-2 fluid (1 volume of water is added to 1 volume of the solution in which 3.40 g of potassium dihydrogen phosphate and 3.55 g of anhydrous disodium hydrogen phosphate are dissolved in water to reach 1000 mL), or 20 mmol/L sodium taurocholate (TCA) in JP-2 fluid (JP-2 fluid is added to 1.08 g of TCA to reach 100 mL) was added to each container. When the compound was completely dissolved, appropriate amount of the compound of the present invention was added. After shaken for 1 hour at 37° C., the mixture was filtered, and 100 μL of methanol was added to 100 μL of each filtrate (double dilution). The dilution rate was changed as necessary. The absence of air bubbles and deposits were confirmed, and the containers were hermetically sealed and shaken. The compound of the present invention was quantified by the absolute calibration curve method using HPLC.

Test Example 12: Ames Test

The compound of the present invention is evaluated for its mutagenicity by the Ames test with *Salmonella typhimurium* TA98, TA100, TA1535 and TA1537 strains and an *Escherichia coli* WP2uvrA strain as test bacterial strains. 0.1 mL of a DMSO solution of the compound of the present invention is mixed with 0.5 mL of S9 mix under metabolic activation conditions or 0.5 mL of a phosphate buffer solution and 0.1 mL of each test bacterial solution under non-metabolic activation conditions, and the mixture is overlaid on a minimum glucose agar plate together with 2 mL of soft agar for overlay containing histidine and biotin, or tryptophan. At the same time, similar tests are also conducted as to a negative control substance (DMSO) and a positive control substance (2-(2-furyl)-3-(5-nitro-2-furyl)acrylamide, sodium azide, 9-aminoacridine, or 2-aminoanthracene). After culture at 37° C. for 48 hours, revertant colonies that have appeared are counted and evaluated by comparison with the negative control group. When the number of revertant colonies increases in a concentration-dependent manner and becomes twice or more the number of colonies of the negative control group, positivity (+) is determined.

Test Example 13: Nav Test

For the purpose of assessing risk of a rhythmogenesis of the compound of the present invention, effects of the compound of the present invention on Na$^+$ current ($I_{Na}$), which plays an important role in the depolarization process of myocardium, was studied using HEK cells expressing Voltage gated sodium channel (Nav 1.5 channel) encoded by SCN5A gene.

A cell is retained at a membrane potential of −100 mV by the whole cell patch clamp method using an automated patch clamp system (QPatch; Sophion Bioscience A/S), then $I_{Na}$ induced by depolarization stimulation at −10 mV for 20 milliseconds, was recorded. A solution of 0.3% dimethylsulfoxide in an extracellular solution (NaCl: 145 mmol/L, KCl: 4 mmol/L, CaCl$_2$: 2 mmol/L, MgCl$_2$: 1 mmol/L, glucose: 10 mmol/L, HEPES (4-(2-hydroxyethyl)-1-piperazineethanesulfonic, acid): 10 mmol/L, TEA (tetraethylammonium hydroxide): 10 mmol/L, pH=7.4) was used as a vehicle. The vehicle and a solution of the compound of the present invention dissolved at an objective concentration in the extracellular solution were respectively applied to the cell for 5 minutes or more at room temperature. From the obtained $I_{Na}$, an absolute value of the maximum peak current was measured based on the current value at the resting membrane potential using analysis software (QPatch Assay software; Sophion Bioscience A/S). The maximum peak current at the time of the application of the compound of the present invention with respect to the maximum peak current at the time of the application of the vehicle was further calculated to evaluate the influence of the compound of the present invention on $I_{Na}$.
(Result)
Compound I-2: 101%
Compound I-15: 92.1%
Compound II-31: 79%

From the above results in which no apparent current increase was observed, it has been revealed that the compound of the present invention has low concerns of arrhythmia due to an increase in Na current.

Test Example 14: Anti-HIV Activity Evaluation Test Using Peripheral Blood Mononuclear Cells (PBMC) of Healthy Humans Serial dilutions of a test sample were prepared in a 96-well microplate (50 µL/well). 1.0×10$^5$/well of PBMC stimulated with Phytohemagglutinin (PHA) and an HIV viral solution were mixed in the required number of wells and the mixture was reacted at 37° C. for 1 hour. After the reaction, the cell suspension was centrifuged and the supernatant was discarded, and the infected cells were dispersed in the culture medium in the required number of wells at 150 µL/well. The obtained medium was dispensed at 150 µL/well to a 96-well microplate containing the test sample. The plate was mixed with a plate mixer and cultured for 4 days in a CO$_2$ incubator. The reverse transcriptase activity in the culture medium was measured. A 90% HIV inhibitory concentration (EC90) was determined from a concentration-dependent curve using the following 4 parameter logistic curve fitting model.

$$y=A+((B-A)/(1+(C/x)^D))$$

A=minimum rate of inhibition (negative control, 0%)
B=maximum rate of inhibition (positive control, 100%)
C=compound concentration at an inflection point
D=slope coefficient
x=compound concentration
y=rate of inhibition (%)
(Results)
Compound II-31: 0.73 nM
Compound II-51: 3.3 nM Test Example 15: Anti-HIV Activity Evaluation Test in the Presence of Human Serum Protein Serial dilutions of a test sample were prepared in a 96-well microplate (50 µL/well). A human serum protein solution (50% human serum protein concentration) was dispensed at 100 µL/well into a 96-well microplate containing the test sample, and allowed to be left still at room temperature for 1 hour. For the plate of serum absence, the culture medium was dispensed at 100 µL/well. 3.0×10$^5$/well of MT-4 cells and 3 µL/well of an HIV viral solution were mixed in an amount of the required number of wells, and the mixture was reacted at 37° C. for 1 hour. After the reaction, the cell suspension was centrifuged and the supernatant was discarded, and the infected cells were dispersed in the culture medium in an amount of the required number of wells at 50 µL/well, and dispensed at 50 µL/well to a 96-well microplate containing the test sample and human serum protein (final concentration of the human serum protein: 25%). The plate was mixed with a plate mixer and cultured for 4 days in a CO$_2$ incubator. An MTT (3-(4,5-dimethyl-thiazol-2-yl-2,5-diphenyltetrazolium bromide) solution was dispensed at 30 µL/well. The plate was reacted for 1 hour in a CO$_2$ incubator. 150 µL of the supernatant was removed from each well so as not to take up the cells. 150 µL of a cell lysis solution was added to each well and well mixed with a plate mixer until the cells were completely lysed. The absorbance of the mixed plate was measured at two wavelengths of 560 nm and 690 nm using a microplate reader. A 50% HIV inhibitory concentration (EC50) was determined from a concentration-dependent curve using the following 4 parameter logistic curve fitting model.

$$y=A+((B-A)/(1+(C/x)^D))$$

A=minimum rate of inhibition (negative control, 0%)
B=maximum rate of inhibition (positive control, 100%)
C=compound concentration at an inflection point
D=slope coefficient
x=compound concentration
y=rate of inhibition (%)

Potency whift (PS) was also calculated based on the expression below. Note that PS is a 100% extrapolation value of human serum protein concentration.

PS=4×(EC50 in the presence of 25% human serum protein/EC50 in the absence of human serum protein)

(Result)
PS in the presence of human serum protein is shown in the table (100% extrapolation value).
Compound II-31: 364
Compound II-51: 236

Preparation Example

The compound of the present invention can be administered as a pharmaceutical composition through any conventional route, particularly, enterally, for example, orally, for example, in the form of a tablet or a capsule, or parenterally, for example, in the form of an injection or a suspension, or topically, for example, in the form of a lotion, a gel, an ointment or a cream, or in a transnasal form or a suppository form. A pharmaceutical composition comprising the compound of the present invention in a free form or in a pharmaceutically acceptable salt together form with at least one pharmaceutically acceptable carrier or diluent can be produced by a mixing, granulation or coating method according to a conventional method. For example, an oral composition can be prepared as a tablet, a granule, or a capsule containing an excipient, a disintegrant, a binder, a lubricant, or the like and the active ingredient or the like. Also, an injectable composition can be prepared as a solution or a suspension and may be sterilized. The injectable composition may also contain a preservative, a stabilizer, a buffering agent, or the like.

INDUSTRIAL APPLICABILITY

The compound of the present invention has integrase inhibitory activity and/or cell growth inhibitory activity against a virus, particularly, HIV. Accordingly, the compound of the present invention is useful in the prevention or treatment of various diseases, virus infections (e.g., AIDS) and the like involving integrase.

The invention claimed is:

1. A method for treating an preventing HIV infection, comprising administering a compound or a pharmaceutically acceptable salt thereof, wherein the compound is selected from the group consisting of

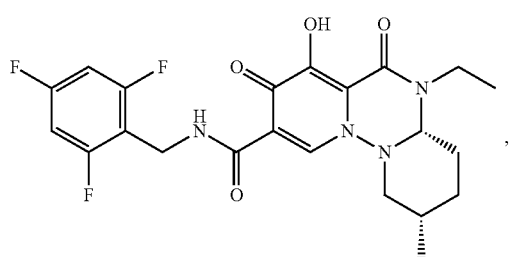
II-20

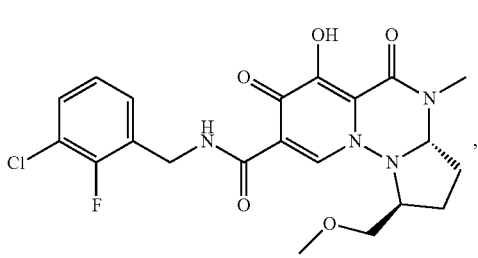
II-31

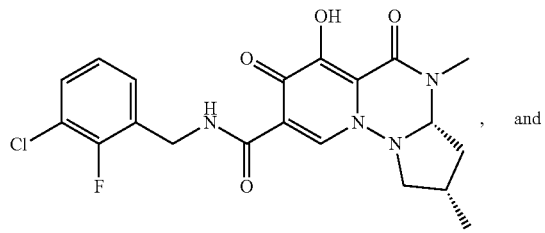
II-42

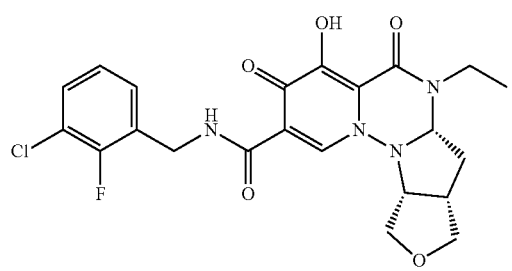
II-60

, and

2. The method of treating HIV infection according to claim 1, wherein the compound is:

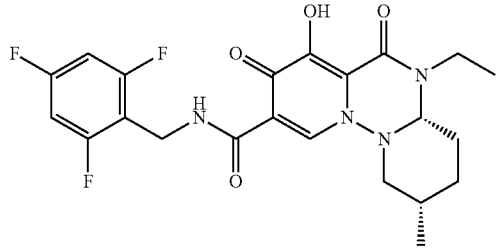
II-20

3. The method of treating HIV infection according to claim 1, wherein the compound is:

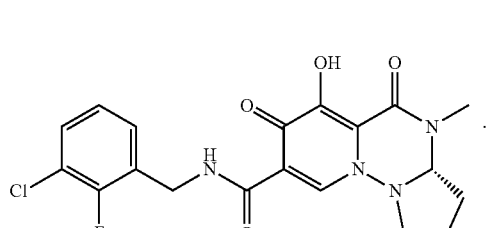
II-31

4. The method of treating HIV infection according to claim 1, wherein the compound is:

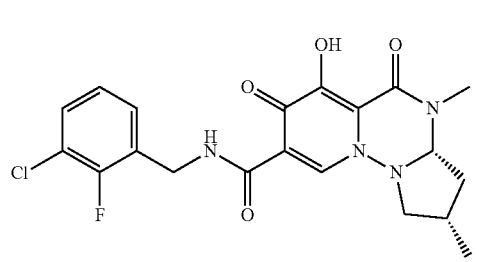
II-42

5. The method of treating HIV infection according to claim 1, wherein the compound is:

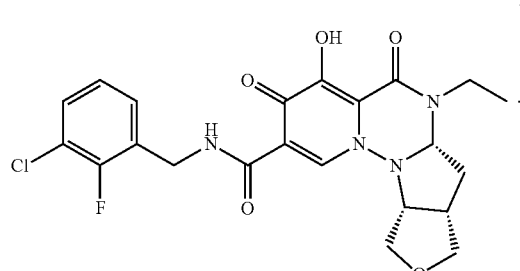
II-60

6. A method of treating HIV infection, comprising administering a compound selected from the group consisting of:

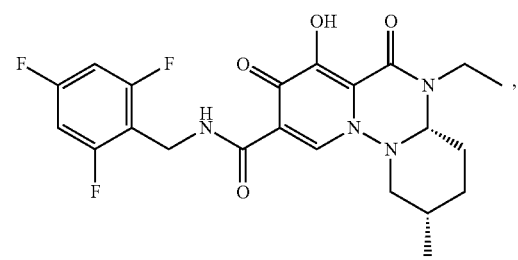
II-20

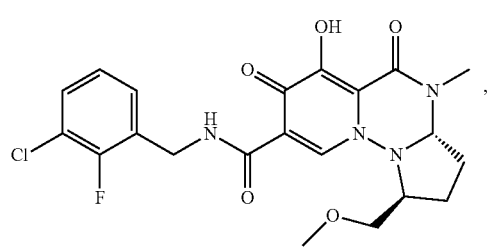
II-31

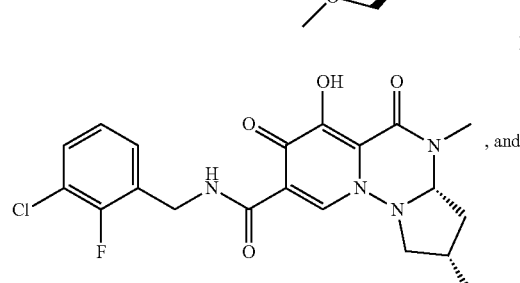
II-42
, and

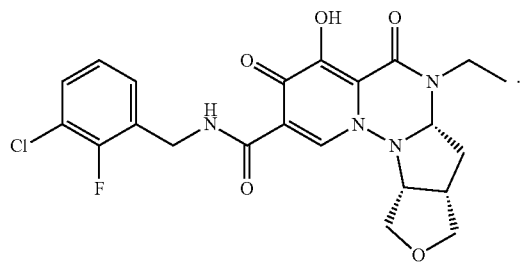
II-60

7. The method of treating HIV infection according to claim 6, wherein the compound is:

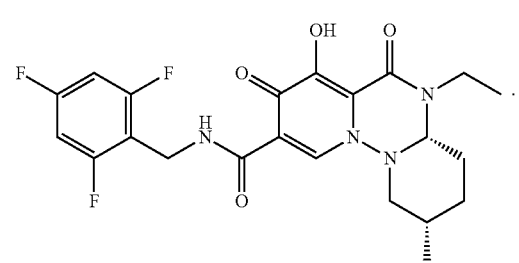
II-20

8. The method of treating HIV infection according to claim 6, wherein the compound is:

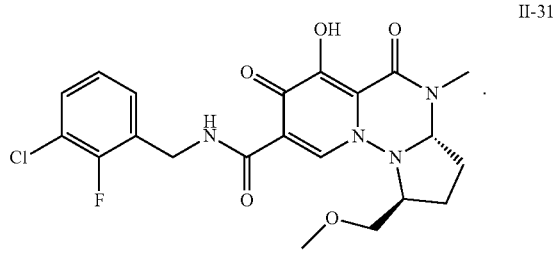 [SMILES: COC[C@@H]1CC[C@H]2N(C)C(=O)c3c(O)c(=O)c(C(=O)NCc4cccc(Cl)c4F)cn3N12]
II-31

9. The method of treating HIV infection according to claim 6, wherein the compound is:

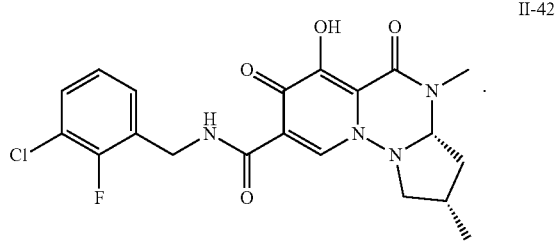 [SMILES: C[C@H]1C[C@H]2N(C)C(=O)c3c(O)c(=O)c(C(=O)NCc4cccc(Cl)c4F)cn3N2C1]
II-42

10. The method of treating HIV infection according to claim 6, wherein the compound is:
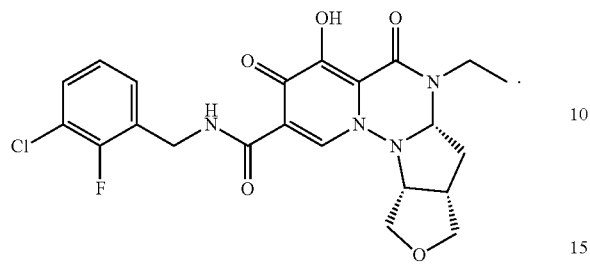
II-60

UNITED STATES PATENT AND TRADEMARK OFFICE
CERTIFICATE OF CORRECTION

PATENT NO. : 12,139,489 B2
APPLICATION NO. : 18/124827
DATED : November 12, 2024
INVENTOR(S) : Yoshiyuki Taoda et al.

Page 1 of 1

It is certified that error appears in the above-identified patent and that said Letters Patent is hereby corrected as shown below:

In the Claims

Column 129, Line 40, delete "an preventing"

Signed and Sealed this
Twentieth Day of May, 2025

Coke Morgan Stewart
*Acting Director of the United States Patent and Trademark Office*